US005670497A

United States Patent [19]
Bold et al.

[11] Patent Number: 5,670,497
[45] Date of Patent: Sep. 23, 1997

[54] CYCLIC HYDRAZINE COMPOUNDS

[75] Inventors: Guido Bold, Gipf-Oberfrick, Switzerland; Shripad S. Bhagwat, Libertyville, Ill.; Alexander Fässler, Oberwil, Switzerland; Marc Lang, Mulhouse, France

[73] Assignee: Ciba-Geigy Corporation, Tarrytown, N.Y.

[21] Appl. No.: 581,508

[22] PCT Filed: Jul. 7, 1994

[86] PCT No.: PCT/EP94/02235

§ 371 Date: Jan. 11, 1996

§ 102(e) Date: Jan. 11, 1996

[87] PCT Pub. No.: WO95/02582

PCT Pub. Date: Jan. 26, 1995

[30] Foreign Application Priority Data

Jul. 14, 1993 [CH] Switzerland .......... 02 114/93
Nov. 5, 1993 [CH] Switzerland .......... 03 333/93

[51] Int. Cl.$^6$ .............. A01N 43/00; A61K 31/33

[52] U.S. Cl. .......... 514/183; 540/488; 540/489; 540/492

[58] Field of Search .......... 540/488, 489, 540/492; 514/183

[56] References Cited

FOREIGN PATENT DOCUMENTS

| 2230979 | 1/1974 | Germany . |
| 9209297 | 6/1992 | WIPO . |
| 9307128 | 4/1993 | WIPO . |

OTHER PUBLICATIONS

Thornber, C.W., Chem. Soc. Reviews 18, 563–5 (1979).
Derwent abstract 04191v/03 (Corresp. to DE–2230–979).

Primary Examiner—Matthew V. Grumbling
Assistant Examiner—Michael Bucknum
Attorney, Agent, or Firm—Marla J. Mathias

[57] ABSTRACT

This invention relates to substituted cyclic carbonyls and derivatives thereof useful as retroviral protease inhibitors to pharmaceutical compositions comprising such compounds, and to methods of using these compounds for treating vital infection.

17 Claims, No Drawings

CYCLIC HYDRAZINE COMPOUNDS

This is a 371 of PCT/EP 94/02235, filed Jul. 7, 1994.

The invention relates to derivatives of cyclic hydrazines and salts thereof, to processes for the preparation of those compounds and salts thereof, to pharmaceutical compositions comprising those compounds or salts thereof, and to the use of those compounds or salts thereof in the therapeutic or diagnostic treatment of the human or animal body or in the preparation of pharmaceutical compositions.

According to WHO estimates, more than 12 million people are at present infected with HIV-1 or HIV-2.

Hitherto, the treatment of retroviral diseases, such as AIDS, has involved principally the use of inhibitors of reverse transcriptase, an enzyme active in the conversion of retroviral RNA into DNA, such as 3+-azido-3'-deoxythymidine (AZT) or dideoxyinosine (DDI), and also trisodium phosphonoformate, ammonium 21 -tungsto-9-antimonate, 1-β-D-ribofuran-oxyl-1,2,4-triazole-3-carboxamides and dideoxycytidine as well as adriamycin. Attempts have also been made to introduce into the body, for example in the form of a recombinant molecule or molecule fragment, the T4-cell receptor which is present in certain cells of the defence system of the human body and which is responsible for the anchoring and introduction of infectious virus particles into those cells and thus for their infection. The desired result is that binding sites for the virus would be titrated out and the virions would therefore no longer be able to bind to the cells. Compounds, such as polymannoacetate, that prevent the penetration of the virus through the cell membrane by other methods, are also used.

In addition, reports have been made of first clinical trials with an inhibitor of HIV-protease, N-tert-butyl-decahydro-2-[2(R)-hydroxy-4-phenyl-3(S)-[[N-2-quinolylcarbonyl-L-asparaginyl]amino]butyl]-(4aS,8aS)-isoquinoline-3(S)-carboxamide (Ro 31-8959) (for example G. J. Muirhead et at., Brit. J. Clin. Pharmacol. 34, 170P–171P (1992)).

In the AIDS viruses, HIV-1 and HIV-2, and other retroviruses, the proteolytic maturation, for example of the core proteins of the virus, is brought about by an aspartate protease, such as HIV-protease. Without that proteolytic maturation, it is not possible for infectious virus particles to be formed. Owing to the central role played by the mentioned aspartate protease, such as HIV-1- and HIV-2-protease, in virus maturation, and on the basis of experimental results, for example using infected cell cultures, it is assumed that effective inhibition of the maturation step effected by that protease in vivo will suppress the assembly of mature virions. Corresponding inhibitors can accordingly be used therapeutically.

The aim of the present invention is to provide a novel class of compounds having favourable pharmacological properties.

The compounds according to the invention are compounds having the formula I

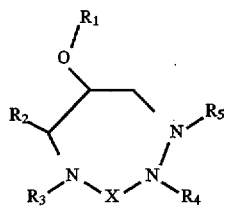
(I)

wherein $R_1$ is hydrogen or acyl, $R_2$, $R_3$, $R_4$ and $R_5$ are each independently of the others unsubstituted or substituted alkyl or alkenyl, and X together with the two bonds shown in the formula forms a bivalent radical selected from the group consisting of
—(C=O)—, —(C=S)—, —(S=O)—, —(S(=O)$_2$)—, —(P=O)—,

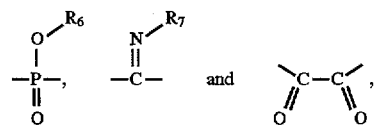

$R_6$ being unsubstituted or substituted alkyl and $R_7$ being hydrogen, unsubstituted or substituted alkyl, hydroxy, amino, alkyloxy, cyano or aryloxy, and salts thereof.

The carbon atoms carrying the radical $R_1$—O— and the radical $R_2$ in compounds of formula I may, because they are centres of asymmetry, be in the (R)-, (S)- or (R,S)-configuration, as may any other asymmetrical carbon atoms present in the substituents. Accordingly, the compounds of formula I may be in the form of mixtures of isomers or pure isomers, especially in the form of mixtures of diastereoisomers, mixtures of enantiomers, such as racemates, or pure enantiomers. Preferred are the compounds of formula I wherein the carbon atoms substituted by $R_1$—O— and by $R_2$ both have the (S)-configuration or both have the (R)-configuration, and any other asymmetrical carbon atoms present are either in the (R)- or (S)-configuration or in the (R,S)-configuration, i.e. compounds of formula Ia falling under formula I

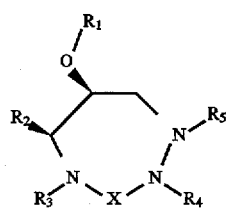
(Ia)

or of formula Ib falling under formula I

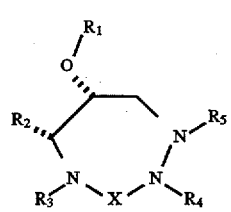
(Ib)

wherein the radicals are as defined for compounds of formula I. Other isomers are possible, for example when double bonds are present, for example olefinic double bonds and C=N double bonds. The present invention relates also to all stable isomers of compounds of formula I. Stable compounds are to be understood as being those compounds which are sufficiently stable to allow isolation from a reaction mixture with a usable degree of purity and to allow the formulation of a pharmaceutical composition.

Within the scope of the present Application, the general terms used hereinbefore and hereinafter have preferably the following meanings unless otherwise indicated:

The term "lower" denotes a radical having up to and including a maximum of 7, especially up to and including a maximum of 4, carbon atoms, more especially having up to 2 carbon atoms. In the case of lower alkenyl or lower alkynyl from 2 to 7, preferably from 2 to 4, carbon atoms are present and in the case of lower alkenoyl or lower alkynoyl from 3 to 7, preferably 3 or 4, carbon atoms are present. Depending on the number of carbon atoms, lower alkyl, lower alkanoyl, lower alkenyl and lower alkenoyl may be unbranched or branched.

Wherever compounds of formula I are concerned, the corresponding compounds of formula Ia or of formula Ib can always be used as preferred compounds.

Wherever compounds, salts, etc. in the plural are concerned, the singular can always be used also.

Acyl $R_1$ is preferably an acyl radical that has up to 25, preferably up to 19, carbon atoms and that is bonded via its carbonyl group to the bonding oxygen atom, and is especially the acyl radical of an unsubstituted or substituted alkanoic, alkenoic or alkynoic acid; or of an unsubstituted or substituted amino acid; or is also an aminocarbonyl group, an N-substituted aminocarbonyl group or an acyl radical of a semiester of carbonic acid bonded via its carbonyl group to the bonding oxygen atom.

A preferred acyl group $R_1$ of a carboxylic acid is, for example, unsubstituted $C_1-C_{20}$-alkanoyl, $C_3-C_{20}$alkenoyl or $C_3-C_{20}$alkynoyl, or substituted $C_1-C_{20}$alkanoyl, $C_3-C_{20}$-alkenoyl or $C_3-C_{20}$alkynoyl, especially lower alkanoyl, such as formyl, acetyl, propionyl, butyryl, methylpropionyl, pentenoyl, pivaloyl, valeroyl or heptanoyl, octanoyl, nonanoyl, decanoyl, undecanoyl, dodecanoyl, palmitoyl, lower alkenoyl, lower alkynoyl, or substituted lower alkanoyl wherein the substituents are selected, for example, from one or more radicals, preferably from up to three radicals, especially from one or two radicals selected from the group consisting of hydroxy, lower alkoxy, lower alkoxy-lower alkoxy, lower alkoxy-lower alkoxy-lower alkoxy, phenyl-lower alkoxy, naphthyl-lower alkoxy, phenyloxy-lower alkoxy, wherein the phenyl radical may be unsubstituted or mono- to tri-substituted, for example, by halogen, such as fluorine, chlorine or bromine, phenoxy, naphthyloxy, lower alkanoyloxy, phenyl-lower alkanoyloxy, such as benzoyloxy or phenylacetyloxy, halogen, such as fluorine, chlorine, bromine or iodine, especially fluorine or chlorine, carboxy, lower alkoxycarbonyl, such as tert-butoxycarbonyl or methoxycarbonyl, phenyl-lower alkoxycarbonyl, such as benzyloxycarbonyl, carbamoyl, lower alkylcarbamoyl, hydroxy-lower alkylcarbamoyl, di-lower alkylcarbamoyl, bis(hydroxy-lower alkyl) carbamoyl, cyano, oxo, $C_3-C_8$cycloalkyl, such as cyclopropyl, cyclobutyl, cyclopentyl or cyclohexyl, phenyl, naphthyl, $C_6-C_{12}$bicycloalkyl, such as decahydronaphth-2-yl, $C_9-C_{14}$-tricycloalkyl, such as 1- or 2-adamantyl, $C_4-C_8$cycloalkenyl, such as 1-cyclohexenyl or 1,4-cyclohexadienyl, heterocyclyl, which is preferably a saturated, partially saturated or unsaturated single ring containing from 3 to 7, preferably from 5 to 7, ring atoms and up to four hetero atoms selected from nitrogen, sulfur and oxygen, preferably 1 or 2 of the mentioned hetero atoms; wherein the ring is either present as such or may be up to twice, preferably once, benzo-fused, cyclopenta-, cyclohexa- or cyclohepta-fused; and may be unsubstituted or substituted, especially by lower alkyl, mono-, di- or tri-phenyl-lower alkyl wherein phenyl is unsubstituted or substituted, for example, by lower alkoxy, such as methoxy, for example triphenylmethyl, which is preferably bonded to a nitrogen atom, lower alkanoyl, hydroxy, lower alkoxy, phenyl-lower alkoxy, such as benzyloxy, phenyl-lower alkoxycarbonyl, such as benzyloxycarbonyl, hydroxy-lower alkyl, such as hydroxymethyl, halogen, cyano and/or by trifluoromethyl, for example pyrrolyl, 2,5-dihydropyrrolyl, furyl, thienyl, tetrahydrofuryl, cyclohepta[b]pyrrolyl, pyrrolidinyl, imidazolyl, imidazolidinyl, pyrazolinyl, pyrazolidinyl, triazolyl, such as 1,2,3-, 1,2,4- or 1,3,4-triazolyl, tetrazolyl, such as 1- or 2-tetrazolyl, tetrahydro-oxazolyl, tetrahydro-isoxazolyl, tetrahydro-thiazolyl, tetrahydro-isothiazolyl, indolyl, isoindolyl, quinolyl, isoquinolyl, benzimidazolyl, benzofuranyl, pyridyl, pyrimidinyl, pyrazinyl, piperidinyl, piperazin-1-yl, morpholino, thiomorpholino, S,S-dioxothiomorpholino, 1,2-dihydro- or 1,2,3,4-tetrahydro-quinolyl, or 1,2-dihydro- or 1,2,3,4-tetrahydro-isoquinolyl, the mentioned radicals being unsubstituted or substituted as indicated above, especially by lower alkyl, for example in 4-lower alkyl-piperazin-1-yl, such as 4-methyl- or 4-ethyl-piperazin-1-yl, by lower alkanoyl, for example in 4-lower alkanoyl-piperazin-1-yl, such as 4-acetyl-piperazin-1-yl, or by hydroxy-lower alkyl, for example in 5-hydroxymethylfuran-2-ylcarbonyl, and aryl, preferably $C_6-C_{14}$aryl, for example phenyl, naphthyl, such as 1- or 2-naphthyl, or fluorenyl, such as fluoren-9-yl, aryl being unsubstituted or mono- or poly-substituted, preferably mono-substituted, for example by lower alkyl, for example methyl, halo-lower alkyl, such as chloro- or bromo-methyl or trifluoromethyl, halogen, for example fluorine or chlorine, hydroxy, lower alkoxy, such as methoxy, lower alkanoyloxy, carboxy, lower alkyloxycarbonyl, phenyl-lower alkoxycarbonyl, carbamoyl, mono- or di-lower alkylcarbamoyl, mono- or di-hydroxy-lower alkylcarbamoyl, heterocyclyl-lower alkyl wherein heterocyclyl is as defined above as a substituent of lower alkanoyl $R_1$, especially heterocyclylmethyl wherein heterocyclyl is bonded via a ring nitrogen atom, for example piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl or thiomorpholinomethyl, cyano and/or by nitro, especially phenyl substituted by one of the mentioned radicals in the p-position: for example lower alkanoyl, such as formyl, acetyl, propionyl, butyryl, methylpropionyl, n-pentanoyl, pivaloyl, valeroyl or heptanoyl, such as n-heptanoyl, hydroxy-lower alkanoyl, for example β-hydroxypropionyl, lower alkoxy-lower alkanoyl, for example lower alkoxyacetyl or lower alkoxypropionyl, such as methoxyacetyl or 3-methoxypropionyl, (lower alkoxy-lower alkoxy)-lower alkanoyl, such as (2-methoxyethoxy)acetyl, ((lower alkoxy-lower alkoxy)-lower alkoxy)-lower alkanoyl, such as (2-(2-methoxyethoxy)ethoxy)acetyl, phenyl-lower alkoxy-lower alkanoyl, such as benzyloxyacetyl, phenyloxy-lower alkoxy-lower alkanoyl, wherein phenyl is unsubstituted or mono- to tri-substituted by halogen, such as fluorine, chlorine or bromine, for example (4-chlorophenyloxy-methoxy)-acetoxy, lower alkanoyloxy-lower alkanoyl, for example lower alkanoyloxyacetyl or lower alkanoyloxypropionyl, such as acetoxyacetyl or 3-acetoxypropionyl, halo-lower alkanoyl, for example α-haloacetyl, such as α-chloro-, α-bromo-, α-iodo-, α,α,α-trifluoro- or α,α,α-trichloro-acetyl, or halopropionyl, such as β-chloro- or β-bromo-propionyl, carboxy-lower alkanoyl, for example carboxy-acetyl or 3-carboxypropionyl, lower alkoxycarbonyl-lower alkanoyl, for example lower alkoxycarbonylacetyl or lower alkoxycarbonylpropionyl, such as methoxycarbonylacetyl, β-methoxycarbonylpropionyl, ethoxycarbonylacetyl, β-ethoxycarbonylpropionyl, tert-butoxycarbonylacetyl or β-tert-butoxycarbonylpropionyl, lower alkanoyl substituted by one of each of the radicals lower alkoxy and phenyl, such as α-methoxy-α-phenyl-acetyloxy, for example in the (R)- or the (S)-configuration, carbamoyl-lower alkanoyl, for example carbamoylacetyl or β-carbamoylpropionyl, lower alkylcarbamoyl-lower alkanoyl, di-lower alkylcarbamoyl-lower alkanoyl, hydroxy-carboxy-lower alkanoyl, hydroxy-lower alkoxycarbonyl-lower alkanoyl, dihydroxy-carboxy-lower alkanoyl, dihydroxy-lower alkoxycarbonyl-lower alkanoyl, heterocyclyl-lower alkanoyl, for example pyrrolylcarbonyl, such as 2- or 3-pyrrolylcarbonyl, furylcarbonyl, for example 2-furylcarbonyl, 5-hydroxymethyl-furan-2-ylcarbonyl, thienylcarbonyl, for example 2-thienylcarbonyl, pyrrolidinylcarbonyl, such as prolyl, N-phenyl-lower alkoxycarbonylpyrrolidinyl, such as N-benzyloxycarbonylprolyl, imidazolylcarbonyl, such as 4-imidazolylcarbonyl, imidazolylacetyl, such as 4-imidazolylacetyl, imidazolylpropionyl, such as 3-(4-imidazolyl)propionyl, 3-(1-triphenylmethyl-imidazol-4-yl) propionyl, 1-pyrazolylacetyl, pyridylcarbonyl, for example 2-, 3- or 4-pyridylcarbonyl, pyridylacetyl, such as 2-pyridylacetyl, pyridylpropionyl, such as 3-(pyridin-2-yl)-propionyl, indolylcarbonyl, for example 2-, 3- or 5-indolylcarbonyl, 1-methyl-, 5-methyl-, 5-methoxy-, 5-benzyloxy-, 5-chloro- or 4,5-dimethyl-indolyl-2-carbonyl, quinolylcarbonyl, such as quinolin-2-ylcarbonyl, isoquinolylcarbonyl, such as isoquinolin-3-ylcarbonyl, pyrrolidinylcarbonyl, such as pyrrolidinyl-3-carbonyl, piperidinylcarbonyl, for example 2-, 3- or 4-piperidinylcarbonyl, pyrazinylcarbonyl, such as pyrazin-2-ylcarbonyl, morpholinocarbonyl, thiomorpholinocarbonyl, morpholinoacetyl, thiomorpholinoacetyl, or 4-lower alkyl-1-piperazinoacetyl, such as 4-methyl-piperazinoacetyl, lower alkenoyl, for example acryloyl, vinylacetyl, crotonoyl or 3- or 4-pentenoyl, lower alkynoyl, for example propioloyl or 2- or 3-butynoyl, $C_3-C_8$ cycloalkylcarbonyl or $C_3-C_8$ cycloalkylacetyl, for example cyclopropyl-, cyclobutyl-, cyclopentyl- or cyclohexyl-carbonyl, cyclopropylacetyl, cyclopentylacetyl or cyclohexylacetyl, phenyl-lower alkanoyl, for example benzoyl, phenylacetyl or 3-phenylpropionyl, wherein phenyl is unsubstituted or mono- or poly-substituted by lower alkyl, for example methyl, halo-lower alkyl, such as chloro- or bromo-methyl, halogen, for example fluorine or chlorine, hydroxy, lower alkoxy, for example methoxy, piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholino-lower alkyl, such as morpholinomethyl, thiomorpholinomethyl, cyano and/or by nitro, for example 4-chloromethyl-, 4-bromomethyl-, 4-fluoro-, 4-chloro-, 4-methoxy-, 4-morpholinomethyl-, 4-thiomorpholinomethyl-, 4-cyano- or 4-nitro-benzoyl, or lower alkylphenylacetyl, such as 4-methylphenylacetyl.

Preferred acyl $R_1$ of an acyl radical of a semiester of carbonic acid bonded via its carbonyl group to the bonding oxygen atom is, for example, unsubstituted or substituted alkyloxycarbonyl, especially unsubstituted or substituted lower alkoxycarbonyl, for example methoxy-, ethoxy- or tert-lower alkoxy-carbonyl, such as tert-butoxycarbonyl, 2-halo-lower alkoxycarbonyl, for example 2-chloro-, 2-bromo-, 2-iodo- or 2,2,2-trichloroethoxycarbonyl; aryl-lower alkoxycarbonyl, for example arylmethoxy-carbonyl, wherein aryl has preferably from 6 to 14 carbon atoms, is unsubstituted or mono- or poly-substituted, preferably mono-substituted, for example by a substituent selected from lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkyloxycarbonyl, phenyl-lower alkoxycarbonyl, carbamoyl, mono- or di-lower alkylcarbamoyl, mono- or di-hydroxy-lower alkylcarbamoyl, halo-lower alkyl, such as trifluoromethyl, heterocyclyl-lower alkyl wherein heterocyclyl is as defined above as a substituent of lower alkanoyl $R_1$, especially heterocyclylmethyl wherein heterocyclyl is bonded via a ring nitrogen atom, for example piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl or thiomorpholinomethyl, cyano and nitro, and is especially phenyl, 1- or 2-naphthyl, fluorenyl, or phenyl mono- or poly-substituted by a substituent selected from lower alkyl, for example methyl or tert-butyl, lower alkoxy, for example methoxy, ethoxy or tert-butoxy, hydroxy, halogen, for example fluorine, chlorine or bromine, and nitro, for example phenyl-lower alkoxycarbonyl, such as benzyloxycarbonyl, 4-methoxybenzyloxycarbonyl, 4-nitrobenzyloxycarbonyl, diphenyl-lower alkoxycarbonyl, such as diphenylmethoxycarbonyl, di-(4-methoxyphenyl)-methoxycarbonyl, trityloxycarbonyl or fluorenyl-lower alkoxycarbonyl, such as 9-fluorenylmethoxycarbonyl; or also heterocyclyl-lower alkoxycarbonyl wherein heterocyclyl is as defined above as a substituent of lower alkanoyl $R_1$, for example furan-2-ylmethoxycarbonyl or pyridin-2-, -3- or -4-ylmethoxycarbonyl. The definitions failing under the definition of acyl groups $R_1$ of a semiester of carbonic acid may preferably be omitted from any of the definitions of compounds of formula I mentioned hereinbefore and hereinafter.

A preferred N-substituted aminocarbonyl group as acyl $R_1$ carries at the nitrogen atom 1 or 2 substituents selected independently of one another from unsubstituted or substituted lower alkyl, wherein the substituents of lower alkyl are selected from those mentioned above for substituted lower alkanoyl $R_1$ and may be present in the number defined there, preferably substituents selected from hydroxy, lower alkoxy, lower alkanoyloxy, phenyl-lower alkanoyloxy, such as benzoyloxy or phenylacetyloxy, halogen, such as fluorine, chlorine, bromine or iodine, especially fluorine or chlorine, carboxy, lower alkoxycarbonyl, phenyl-lower alkoxycarbonyl, such as benzyloxycarbonyl, cyano, oxo and phenyl or naphthyl each of which is unsubstituted or mono- or poly-substituted, preferably mono-substituted, for example by a substituent selected from lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkyloxycarbonyl, phenyl-lower alkoxycarbonyl, halo-lower alkyl, such as trifluoromethyl, cyano and nitro, especially phenyl substituted in the p-position by one of the mentioned radicals; especially selected from unsubstituted lower alkyl, such as methyl or ethyl; and aryl that preferably has from 6 to 14 carbon atoms and is unsubstituted or mono- or poly-substituted, preferably mono-substituted, for example by a substituent selected from lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkyloxycarbonyl, phenyl-lower alkoxycarbonyl, halo-lower alkyl, such as trifluoromethyl, cyano and nitro, the nitrogen atom of the carbamoyl group carrying not more than one aryl radical; in particular an acyl group $R_1$ of an N-substituted carbamic acid is mono- or di-lower alkylaminocarbonyl, such as N-methyl-, N-ethyl-, N,N-dimethyl- or N,N-diethyl-aminocarbonyl, or phenyl-lower alkylaminocarbonyl wherein phenyl is unsubstituted or substituted by one or more substituents selected from lower alkyl, for example methyl, halo-lower alkyl, such as chloro- or bromo-methyl or trifluoromethyl, halogen, for example fluorine or chlorine, hydroxy, lower alkoxy, such as methoxy, carboxy and cyano, preferably by up to three of those substituents selected independently of one another, especially by one of those substituents, for example in the p-position, such as in N-benzyl-, N-(4-fluorobenzyl)-, N-(4-chlorobenzyl)-, N-(4-trifluoromethylbenzyl)- or N-(4-cyanobenzyl)-aminocarbonyl; special preference is given to aminocarbonyl substituted at the nitrogen atom by only one radical, for example N-lower alkylaminocarbonyl, such as N-methyl- or N-ethyl-aminocarbonyl, or phenyl-lower-alkylaminocarbonyl wherein phenyl is unsubstituted or substituted by one or more substituents selected from lower alkyl, such as methyl, halo-lower alkyl, such as chloro- or bromomethyl or trifluoromethyl, halogen, such as fluorine or chlorine, hydroxy, lower alkoxy, such as methoxy, carboxy and cyano, preferably by up to three of those substituents selected independently of one another, especially by one of those substituents, for example in the p-position, such as in N-benzyl-, N-(4-fluorobenzyl)-, N-(4-chlorobenzyl)-, N-(4-trifluoromethylbenzyl)- or N-(4-cyanobenzyl)-aminocarbonyl. The definitions falling under the definition of acyl groups $R_1$ of an N-substituted carbamic acid, and the radical aminocarbonyl $R_1$ may preferably be omitted from any of the definitions of compounds of formula I mentioned hereinbefore and hereinafter.

An unsubstituted or substituted amino acid bonded via its carbonyl group to the bonding oxygen atom, as acyl $R_1$, is preferably formed by the amino acid residues (aminoacyl), bonded via the carbonyl of their carboxy group to the oxygen atom that binds $R_1$ (instead of the hydroxy group in the carboxy group of the amino acid concerned), of an α-, β-, γ-oder δ-amino acid, especially of a natural α-amino acid having the L-configuration, such as normally occurs in proteins, or of an epimer of such an amino acid, i.e. having the unnatural D-configuration, or a mixture of the D,L-isomers thereof, of a homologue of such an amino acid, for example wherein the amino acid side chain has been lengthened or shortened by one or two methylene groups, wherein the amino group is in the β-, γ-, or δ-position and/or wherein a methyl group has been replaced by hydrogen, of a substituted aromatic amino acid wherein the aromatic radical has from 6 to 14 carbon atoms, for example of a substituted phenylalanine or phenylglycine wherein the phenyl substituent is selected from lower alkyl, for example methyl, hydroxy, lower alkoxy, for example methoxy, phenyl-lower alkoxy, for example benzyloxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert-butoxycarbonylamino, arylmethoxycarbonylamino wherein aryl has preferably from 6 to 14 carbon atoms, for example benzyloxycarbonylamino or 9-fluorenylmethoxycarbonylamino, halogen, for example fluorine, chlorine, bromine or iodine, carboxy and nitro and occurs one or more times, of a benzo-fused phenylalanine or phenylglycine, such as α-naphthylalanine, or of a hydrogenated phenylalanine or phenylglycine, such as cyclohexylalanine or cyclohexylglycine. The amino acid residue prolyl (from proline, (H-Pro-OH)) already mentioned as acyl group of a carboxylic acid, and the derivatives thereof mentioned there, also belong to the mentioned amino acid residues but, in order to avoid overlapping definitions, they are not included here in the definition of amino acid residues if they are defined elsewhere.

Those amino acid residues may be substituted at free amino or hydroxy functions by one of the radicals defined above in the definition of $R_1$ as acyl radical of an unsubstituted or substituted alkanoic, alkenoic or alkynoic acid; as an aminocarbonyl group, an N-substituted aminocarbonyl group or as an acyl radical of a semiester of carbonic acid bonded via its carbonyl group to the bonding oxygen atom, or by unsubstituted or substituted lower alkyl, as defined below for $R_6$.

Special preference is given to the residue, bonded via the carbonyl of its carboxy group to the bonding oxygen atom and obtainable by removing the OH group in the carboxy group (—COOH), of an amino acid selected from glycine (H-Gly-OH), alanine (H-Ala-OH), 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid, valine (H-Val-OH), norvaline (α-aminovaleric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), trans-3- and trans-4-hydroxyproline, phenylalanine (H-Phe-OH), tyrosine (H-Tyr-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), aspartic acid (H-Asp-OH), asparagine (H-Asn-OH), aminomalonic acid, aminomalonic acid monoamide, glutamic acid (H-Glu-OH), glutamine (H-Gln-OH), histidine, (H-His-OH), arginine (H-Arg-OH), lysine (H-Lys-OH), δ-hydroxylysine, ornithine (α,δ-diaminovaleric acid), 3-aminopropanoic acid, α,γ-diaminobutyric acid and α,β-diaminopropionic acid, especially preferably the residue of an aliphatic amino acid selected from alanine, valine, norvaline, leucine, 3-aminopropionic acid, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid and isoleucine, or of an amino acid selected from glycine, asparagine, glutamine, methionine, lysine, histidine and phenylalanine, wherein (except in cases where there is no asymmetrical carbon atom, for example in the case of glycine) each of the mentioned amino acids may be in the D-, L- or (D,L)-form, preferably in the L-form, and an amino group is unsubstituted or mono- or di-N-alkylated, for example by lower alkyl, such as methyl, n-propyl or n-butyl, imidazolyl-lower alkyl, such as imidazolyl-4-methyl, pyridyl-lower alkyl, such as 2-, 3- or 4-pyridylmethyl, and/or by phenyl-lower alkyl, such as benzyl, and/or N-acylated, for example by unsubstituted or substituted lower alkanoyl, such as defined above for lower alkanoyloxy $R_1$, especially by acetyl, propionyl or pivaloyl, aryl-lower alkanoyl, for example phenyl-lower alkanoyl, such as benzoyl or phenylacetyl, by lower alkoxycarbonyl, such as tert-butoxycarbonyl, or by aryl-lower alkoxycarbonyl, for example phenyl-lower alkoxycarbonyl, such as benzyloxycarbonyl.

Of the last-mentioned radicals, preference is given to acyl groups $R_1$ of an unsubstituted or substituted amino acid selected from aminoacetyl (glycyl), N-lower alkylaminoacetyl, N,N-di-lower alkylaminoacetyl, N-lower alkyl-N-phenyl-lower alkylaminoacetyl, N-lower alkyl-N-lower alkoxycarbonylaminoacetyl and N-pheny-lower alkoxycarbonyl-N-lower alkylaminoacetyl, for example N-methylaminoacetyl, N,N-dimethylaminoacetyl, N-methyl-N-(n-butyl)aminoacetyl, 4-(N,N-dimethylamino) butyryl or N-methyl-N-benzylaminoacetyl, N-imidazolylmethyl-N-lower alkylaminoacetyl, such as N-(imidazol-4-yl-methyl)-N-methylaminoacetyl, N-methyl-N-[(2-, 3- or 4-)pyridylmethyl]-aminoacetyl, such as N-methyl-N-3-pyridylmethylaminoacetyl, N-methyl-N-tert-butoxycarbonylaminoacetyl, N-benzyloxycarbonyl-N-lower alkylaminoacetyl, such as N-benzyloxycarbonyl-N-methylaminoacetyl, histidyl, glutamyl and asparagyl, wherein the amino acid residues (except in cases where there is no asymmetrical carbon atom, for example in the case of Gly) are preferably in the (L)-form or also in the (D)- or (D,L)-form.

In all definitions of compounds of formula I $R_1$ is preferably hydrogen.

Unsubstituted or substituted alkyl, for example for the radicals $R_2$, $R_3$, $R_4$, $R_5$, $R_6$ and/or $R_7$, means an alkyl radical having from 1 to 20, preferably up to 10, carbon atoms, is branched or unbranched and is, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl or n-decyl. Lower alkyl is preferably, for example, methyl, ethyl, n-propyl, isopropyl, n-butyl, isobutyl, sec-butyl, tert-butyl, n-pentyl, iso-pentyl, neopentyl, tert-pentyl, n-hexyl, isohexyl or n-heptyl that is unsubstituted or substituted.

As substituents of substituted lower alkyl, preferably up to four, especially (except in the case of halogen which may be present as substituent up to three times) up to two of the substituents mentioned below, especially one substituent, areas present (except in the case of halogen which may be present as substituent up to three times, the substituents being selected especially from cycloalkyl that has preferably from 3 to 7 carbon atoms, especially in cycloalkyl-lower alkyl wherein lower alkyl is as defined above, for example cycloalkylmethyl, for example having a total of from 4 to 8 carbon atoms, such as cyclopropyl-, cyclobutyl-, cyclopentyl- or cyclohexyl-lower alkyl, such as -methyl or -2-ethyl, cycloalkenyl that has preferably from 3 to 7 carbon atoms, especially in cycloalkenyl-lower alkyl, such as cycloalkenylmethyl, for example having from 4 to 8 carbon atoms, such as 1-cyclohexenylmethyl, 1,4-cyclohexadienylmethyl or 1-cyclohexenyl-1- or -2-ethyl or 1,4-cyclohexadienyl-1- or -2-ethyl, bicycloalkyl that contains preferably from 5 to 10 carbon atoms, especially in bicycloalkyl-lower alkyl, for example bicycloalkylmethyl, for example having from 8 to 11 carbon atoms, such as decahydronaphthyl-2-methyl, bicyclohexyl-, bicycloheptyl-, bicyclooctyl-, bicyclononyl- or bicyclodecyl-2-ethyl or -3-propyl, bicycloalkenyl preferably having from 8 to 12 carbon atoms, especially in bicycloalkenylmethyl, such as 5-norbornen-2-ylmethyl or bicyclo[2.2.2]octen-2-ylmethyl, tricycloalkyl wherein tricycloalkyl contains, for example, from 8 to 10 carbon atoms, especially in tricycloalkyl-lower alkyl, for example tricycloalkylmethyl, for example having from 8 to 11 carbon atoms, such as 12 or 2-adamantylmethyl, aryl that has preferably from 6 to 14 ring carbon atoms such as in phenyl, indenyl, indanyl, naphthyl, anthryl, phenanthryl, acenaphthyl or fluorenyl, and may be unsubstituted or substituted, especially by one or more, especially by up to three, more especially one, of the radicals lower alkyl, for example methyl, ethyl or propyl, halo-lower alkyl, for example trifluoromethyl, phenyl, 1- or 2-naphthyl, hydroxy, lower alkoxy, for example methoxy, phenyl-lower alkoxy, such as benzyloxy, wherein the phenyl radical may itself be unsubstituted or substituted, for example by halogen, such as chlorine or fluorine, hydroxy or by lower alkoxy, such as methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, such as tert-butoxycarbonyl, phenyl-, naphthyl- or fluorenyl-lower alkoxycarbonyl, such as benzyloxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or cyano, especially in aryl-lower alkyl wherein phenyl is present once or also up to three times, for example in diphenyl-, dibenzyl- or triphenyl-lower alkyl, such as di-phenyl-, dibenzyl- or triphenyl-ethyl, and wherein lower alkyl may be unsubstituted or substituted, for example by carboxy, lower alkoxycarbonyl, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxy-carbonyl, aryl-lower alkoxycarbonyl wherein aryl has from 6 to 12 carbon atoms, for example benzyloxycarbonyl, carbamoyl, carbamoyl substituted at the nitrogen atom by one or two radicals selected from lower alkyl, such as methyl, ethyl, propyl, iso-propyl, n-butyl, isobutyl, sec-butyl or tert-butyl, for example in N-methylcarbamoyl, N-(n-butyl)carbamoyl or N,N-dimethylcarbamoyl, from carboxy-lower alkyl or lower alkoxycarbonyl-lower alkyl, for example in the form of carboxymethylcarbamoyl (glycinylcarbonyl) or in the form of tert-butoxycarbonylmethylcarbamoyl, from di-lower alkylamino-lower alkyl, for example 2-dimethylaminoethyl, from hydroxy-lower alkyl, for example hydroxymethyl or hydroxyethyl, and from di-lower alkoxy-lower alkyl, for example 2-(2,2-dimethoxyethyl), and/or by cyano, and is unbranched or branched, especially selected from phenyl-lower alkyl, such as benzyl, 2-phenylethyl or 3-phenylpropyl, wherein the phenyl ring may be unsubstituted or mono- or poly-substituted, for example by lower alkyl, for example methyl, phenyl, halogen, for example fluorine or chlorine, hydroxy, lower alkoxy, for example methoxy, phenyl-lower alkoxy, such as benzyloxy, and/or by nitro, such as 4-chloro-, 4-methoxy- or 4-nitro-benzyl, naphthylmethyl, such as α- or β-naphthylmethyl, indenylmethyl, such as 1-, 2- or 3-indenylmethyl, indanylmethyl, such as 1- or 2-indanylmethyl, phenanthrenylmethyl, such as 9-phenanthrenylmethyl, α-naphthylethyl, β-naphthylethyl, lower alkylphenylethyl, such as 4-methylphenyl-2-ethyl, lower alkoxyphenylethyl, such as 4-methoxyphenyl-2-ethyl, 3-(p-hydroxyphenyl)-propyl, 2,2-diphenylethyl, 2,2-di-(4-methoxyphenyl)-ethyl, 2,2,2-triphenylethyl, 2,2-dibenzylethyl, or 3-α- or 3-β-naphthylpropyl, and phenyl-lower alkyl wherein the lower alkyl radical is substituted by carbamoyl, for example 2-carbamoyl-3-phenylpropyl, such as 2(R,S)-carbamoyl-3-phenylpropyl, 3-α-naphthyl-2-carbamoylpropyl, 3-phenyl- or 3-α-naphthyl-2-tert-butylcarbamoyl-propyl, 3-phenyl- or 3-α-naphthyl-2-(2-dimethylaminoethyl)carbamoyl-propyl, 3-α-naphthyl-2-(carboxy- or tert-butoxycarbonyl) methylcarbamoyl-propyl, 3-phenyl- or 3-α-naphthyl-2-(3-hydroxy-2-propyl)carbamoyl-propyl, 3-phenyl- or 3-α-naphthyl-2-(2,2-dimethoxyethyl)-carbamoylpropyl, and 3-phenyl- or 3-α-naphthyl-2-(5-amino-5-carboxypentyl)-carbamoylpropyl, especially phenyl-lower alkyl, such as phenylethyl, or phenyl-lower alkyl wherein the lower alkyl radical is substituted by carbamoyl, such as 2(R,S)-carbamoyl-3-phenylpropyl, heterocyclyl, which is preferably a single or double ring system having from 3 to 10 ring atoms, is bonded via a carbon atom or, especially, a nitrogen atom, and contains up to three further hetero atoms selected from oxygen, nitrogen, sulfur and sulfur linked to 1 or oxygen atoms, wherein the mentioned ring system may additionally be fused with 1 or 2 phenyl or naphthyl radicals, wherein naphthyl may also be fused on via two sides, or may be fused with 1 or 2 cycloalkyl radicals, wherein cycloalkyl has preferably from 5 to 7 ring atoms; and may be unsaturated or also partially or completely saturated, for example thienyl, furyl, pyrrolyl, imidazolyl, pyrazolyl, oxazolyl, thiazolyl, tetrazolyl, pyridyl, pyrazinyl, pyrimidinyl, pyridazinyl, indolyl, benzimidazolyl, quinolyl, isoquinolyl, 3,1-benzofuranyl, cyclohexa[b]pyrrolyl, cyclohexa[b]pyridyl, cyclohexa[b]pyrazinyl, cyclohexa[b]pyrimidinyl, pyrrolidinyl, pyrrolinyl, imidazolidyl, piperidyl, piperazinyl, morpholinyl, thiomorpholinyl, S,S-dioxo-thiomorpholinyl, indolinyl, isoindolinyl, 4,5,6,7-tetrahydroindolyl, 1,2,3,4-tetrahydroquinolyl or 1,2,3,4-tetrahydroisoquinolyl, wherein heterocyclyl, for example one of the last-mentioned radicals, is unsubstituted or mono- to tri-substituted, preferably mono-substituted, by radicals selected independently of one another from lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, lower alkanoyloxy-lower alkyl, for example acetyloxymethyl, phenyl- or naphthyl-lower alkanoyloxy-lower alkyl, for example benzoyloxy-, phenylacetyloxy- or 1- or 2-naphthoyloxy-methyl, -2-ethyl or -2-(2,2-dimethylethyl), lower alkoxycarbonyloxy-lower alkyl, for example tert-butoxycarbonyloxy-lower alkyl, phenyl-lower alkoxycarbonyloxy-lower alkyl, for example 2-benzyloxycarbonyloxyethyl, amino-lower alkyl, for example aminomethyl, hydroxy, lower alkoxy, for example methoxy or ethoxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxy-ethylcarbamoyl, nitro, oxo and cyano; especially in heteroeyclyl-lower alkyl wherein lower alkyl is unsubstituted or substituted independently from aryl-lower alkyl by one of the substituents defined above under aryl-lower alkyl; wherein heterocyclyl-lower alkyl is selected especially from pyrrolylmethyl, for example 2- or 3-pyrrolylmethyl, thienylmethyl, such as 2-thienylmethyl, furylmethyl, such as 2-furylmethyl, indolylmethyl, such as 2-, 3- or 5-indolylmethyl, 4,5,6,7-tetrahydroindolyl-2-methyl, quinolyl-lower alkyl, for example quinolylmethyl, such as 2-, 3- or 4-quinolylmethyl, isoquinolylmethyl, such as 1-, 3- or 4-isoquinolylmethyl, piperidyl-lower alkyl, such as piperidylmethyl, for example piperidinomethyl or 2-, 3- or 4-piperidylmethyl, piperazinyl-lower alkyl, such as piperazinomethyl, for example piperazin-1-yl-methyl, morpholinyl-lower alkyl, for example morpholino-lower alkyl, such as morpholinomethyl, thiomorpholinyl-lower alkyl, for example thiomorpholino-lower alkyl, such as thiomorpholinomethyl, S,S-dioxothiomorpholinylmethyl, such as S,S-dioxothiomorpholinomethyl, 1,2,3,4-tetrahydroquinolylmethyl, such as 1,2,3,4-tetrahydroquinolyl-2-, -3- or 4-methyl, 1,2,3,4-tetrahydroisoquinolylmethyl, such as 1,2,3,4-tetrahydroisoquinolyl-1-, -3- or 4-methyl, tetrazolyl-lower alkyl, such as 3-(tetrazol-1-yl)-propyl, and pyridyl-lower alkyl, for example pyridylmethyl, such as 2-, 3- or 4-pyridylmethyl, or pyridylethyl, such as 2-, 3- or 4-pyridylethyl, more especially selected from morpholinomethyl, thiomorpholinomethyl, quinolin-2-yl-methyl, 3-(tetrazol-1-yl)-propyl, 2-pyridylmethyl and 2- or 3-pyridylethyl, hydroxy, especially in hydroxy-lower alkyl, such as 3-hydroxypropyl or 2-hydroxy-3-methylpentyl, hydroxy-lower alkoxy, especially in hydroxy-lower alkoxy-lower alkyl, such as 3-hydroxy-n-propoxymethyl, lower alkoxy, especially in lower alkoxy-lower alkyl, for example lower alkoxyethyl or lower alkoxypropyl, such as 2-methoxyethyl, 2-ethoxyethyl or 3-methoxypropyl, lower alkoxy-lower alkoxy, especially in lower alkoxy-lower alkoxy-lower alkyl, such as 2-(2-methoxy-ethoxy) ethyl or 2-methoxymethoxy-3-methyl-pentyl, lower alkoxy-lower alkoxy-lower alkoxy, especially in lower alkoxy-lower alkoxy-lower alkoxy-lower alkyl, such as in 2-[2-(2-methoxy-ethoxy)-ethoxy]-ethyl, lower alkanoyloxy, especially in lower alkanoyloxy-lower alkyl, wherein lower alkanoyloxy is, for example, acetoxy, propionyloxy, butyroxy, isobutyroxy or pivaloyloxy, such as 2-acetoxyethyl or 3-acetoxypropyl, amino, for example in amino-lower alkyl, such as 5-aminopentyl, lower alkanoylamino, especially in lower alkanoylamino-lower alkyl, such as 5-pivaloylamino-pentanoyl, lower alkoxycarbonylamino, especially in lower alkoxycarbonylamino-lower alkyl, such as 5-(tert-butoxycarbonylamino)-pentyl, phenyl-lower alkoxycarbonylamino, especially in phenyl-lower alkoxycarbonylamino-lower alkyl, such as 5-benzyloxycarbonylaminopentyl or 6-benzyloxycarbonylaminohexyl, amino substituted at the amino nitrogen atom by heterocyclyl-lower alkanoyl wherein heterocyclyl is as defined above as substituent of substituted lower alkyl, independently of the radicals mentioned there, especially amino substituted at the amino nitrogen atom by N-morpholino- or N-thiomorpholino-carbonyl, especially in heterocyclyl-lower alkanoylamino-lower alkyl, for example N-morpholino- or N-thiomorpholino-carbonylamino-lower alkyl, such as N-morpholino- or N-thiomorpholino-carbonylamino-methyl or -2-ethyl, preferably up to three halogen atoms, especially in halo-lower alkyl that contains up to 3 halogen atoms, for example 2-haloethyl, such as 2-fluoro-, 2-chloro-, 2-bromo-, 2-iodo-, 2,2,2-trifluoro- or 2,2,2-trichloro-ethyl, or halopropyl, such as 3-chloro- or 3-bromopropyl, carboxy, especially in carboxy-lower alkyl, for example 2-carboxyethyl or β-carboxypropyl, lower alkoxycarbonyl, especially in lower alkoxycarbonyl-lower alkyl, for example lower alkoxycarbonylethyl or lower alkoxycarbonylpropyl, such as 2-methoxycarbonylethyl, 3-methoxycarbonylpropyl, 2-ethoxycarbonylethyl, 3-ethoxycarbonylpropyl or 3-tert-butoxycarbonylpropyl, sulfonyl, especially in sulfonyl-lower alkyl, such as 3-sulfonylpropyl, carbamoyl, especially in carbamoyl-lower alkyl, such as 2-carbamoylethyl or 3-carbamoylpropyl, lower alkylcarbamoyl, especially in lower alkylcarbamoyl-lower alkyl, for example lower alkylcarbamoylethyl or methylcarbamoyl-lower alkyl, such as 2-methylcarbamoylethyl, di-lower alkylcarbamoyl, especially in di-lower alkylcarbamoyl-lower alkyl, for example di-lower alkylcarbamoylethyl or dimethylcarbamoyl-lower alkyl, such as 2-dimethylcarbamoylethyl, carbamoyl substituted at the nitrogen atom by a radical selected from ethylene, trimethylene, tetramethylene and pentamethylene wherein a carbon atom may have been replaced by nitrogen, oxygen, sulfur or sulfur mono- or di-substituted by oxygen, especially in correspondingly N-substituted carbamoyl-lower alkyl, it also being possible for the radical so formed to be completely or partially unsaturated, for example in the form of piperidino-, pyrazin-1-yl-, piperazin-1-yl-, pyrimidin-1-yl-, pyridazin-1-yl-, morpholino-, thiomorpholino- or S,S-dioxothiomorpholino-carbonyl-lower alkyl, such as in 2-morpholinocarbonyl-ethyl, 3-(morpholinocarbonyl)-propyl or 3-(morpholinocarbonyl)-2-isobutyl-propyl, N-heterocyclyl-lower alkyl-carbamoyl or N-lower alkyl-N-heterocyclyl-lower alkyl-carbamoyl, especially in N-heterocyclyl-lower alkyl-carbamoyl-lower alkyl or N-lower alkyl-N-heterocyclyl-lower alkylcarbamoyl-lower alkyl, wherein heterocyclyl is selected preferably from pyrrolyl, furyl, thienyl, imidazolyl, pyrazolyl, oxazolyl, thiazolyl, pyridyl, pyrazinyl, pyrimidinyl, indolyl, quinolyl and isoquinolyl, each of which may be completely or partially saturated, and from morpholinyl and thiomorpholinyl, such as 2-(N-methyl-2-(N-2-pyridylmethyl)-carbamoyl)ethyl, 2-(N-morpholino-lower alkyl-carbamoyl)-lower alkyl, such as 2(R,S)-(N-(2-morpholinoethyl)-carbamoyl-3-methylbutyl, or 2-(N-(pyridyl-lower alkyl)-carbamoyl)-lower alkyl, such as (2(R, S)-(N-(2-pyridylmethyl)-carbamoyl)-3-methyl)-butyl, oxo that is not in the 1-position of the alkyl radical, especially in 2-oxo-lower alkyl, such as 2-acetylethyl or 2-propionylethyl, and cyano, especially in cyano-lower alkyl, such as 2-cyanoethyl, 2- or 3-cyanopropyl or 2-, 3- or 4-cyanobutyl.

Especially preferably, unsubstituted or substituted alkyl $R_1$, $R_2$, $R_3$, $R_4$, $R_5$, $R_6$ and $R_7$ are selected independently of one another from lower alkyl, for example methyl, ethyl, propyl, isopropyl, n-butyl, isobutyl or tert-butyl, cycloalkyl-lower alkyl wherein cycloalkyl has, for example, from 3 to 7 carbon atoms, such as cyclopropyl, cyclobutyl, cyclopentyl, cyclohexyl or cycloheptyl, cycloalkyl being unsubstituted or mono- to tri-substituted by lower alkyl, such as isopropyl, halo-lower alkyl, such as trifluoromethyl, hydroxy, lower alkoxy, amino, mono- or di-lower alkylamino, halogen, such as fluorine, chlorine or bromine, nitro and/or by cyano, and being bonded, preferably terminally, to lower alkyl, especially methyl, ethyl, n-propyl, iso-propyl, n-butyl, isobutyl or tert-butyl, for example cyclopropyl-, cyclobutyl-, cyclopentyl-, cyclohexyl- or cycloheptyl-lower alkyl, such as -methyl or -ethyl, especially preferably cyclopropyl-lower alkyl, such as cyclopropylmethyl, or cyclohexyl-lower alkyl, such as cyclohexylmethyl, and aryl-lower alkyl wherein aryl is, for example, defined independently in the same way as aryl as a substituent of lower alkyl $R_1$, $R_2$, $R_3$, $R_4$, $R_5$, $R_6$ and $R_7$ that is unsubstituted or substituted as defined there, for example phenyl-lower alkyl, such as benzyl, 2-phenylethyl, 3-phenylpropyl, naphthyl-lower alkyl, such as 1- or 2-naphthylmethyl, fluorophenyl-lower alkyl, such as 4-fluorobenzyl, cyanophenyl-lower alkyl, such as 4-cyanobenzyl, lower alkoxyphenyl-lower alkyl, for example 4-lower alkoxybenzyl, such as 4-methoxy- or 4-isobutoxy-benzyl, 4-trifluoro-, 4-hydroxy- or 4-phenyl-lower alkoxy-, such as 4-benzyloxy- or 4-hydroxy-phenylmethyl, especially preferably 4-fluorobenzyl, 4-cyanobenzyl, 4-methoxybenzyl or phenyl-lower alkyl, especially as last defined. $R_7$ can also be cyano.

Especially preferred as unsubstituted alkyl $R_6$ and $R_7$ is unsubstituted lower alkyl, such as methyl, ethyl, propyl, isopropyl, n-butyl, isobutyl or tert-butyl.

Alkenyl $R_2$, $R_3$, $R_4$ and/or $R_7$ is especially alkenyl that has from 3 to 10 carbon atoms and is bonded via a carbon atom without a double bond, especially lower alkenyl, such as allyl.

Alkyloxy $R_7$ has preferably up to 10 carbon atoms and is especially lower alkoxy, such as methoxy or ethoxy.

Aryloxy contains preferably an aryl radical as defined above as substituent of substituted alkyl $R_2$, especially a phenyl or naphthyl radical that is substituted as indicated there or is unsubstituted, for example fluoro-, lower alkoxy-, such as methoxy- or isobutoxy-, or cyano-phenyl or phenyl.

Salts of compounds of formula I are especially (when basic groups are present in compounds of formula I) acid addition salts, salts with bases (when acidic groups are present in compounds of formula I) or, when several salt-forming groups are present, may also be mixed salts or internal salts.

Salts are especially the pharmaceutically acceptable non-toxic salts of compounds of formula I.

Such salts are formed, for example, from compounds of formula I having an acidic group, for example having a carboxy or sulfo group or having a phosphoryl group substituted by one or two hydroxy groups, and are, for example, the salts thereof with suitable bases, such as non-toxic metal salts derived from metals of groups Ia, Ib, IIa and IIb of the Periodic Table of Elements, especially suitable alkali metal salts, for example lithium, sodium or potassium salts, or alkaline earth metal salts, for example magnesium or calcium salts, and also zinc salts or ammonium salts, as well as those salts which are formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl)-amines, such as mono-, bis- or tris-(2-hydroxyethyl)-amine, 2-hydroxy-tert-butylamine or tris (hydroxymethyl)methylamine, N,N-di-lower alkyl-N-(hydroxy-lower alkyl)-amines, such as N,N-dimethyl-N-(2-hydroxyethyl)-amine or tris(2-hydroxyethyl)amine, N-methyl-D-glucamine or quaternary ammonium salts, such as tetrabutylammonium salts. The compounds of formula I having a basic group, for example an amino group, can form acid addition salts, for example with inorganic acids, for example a hydrohalic acid, such as hydrochloric acid, sulfuric acid or phosphoric acid, or with organic carboxylic, sulfonic, sulfo or phospho acids or N-substituted sulfamic acids, such as, for example, acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and also with amino acids, such as, for example, the α-amino acids mentioned hereinbefore, especially glutamic acid and aspartic acid, and with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (with the formation of cyclamates) or with other acidic organic compounds, such as ascorbic acid. Compounds of formula I having acidic and basic groups can also form internal salts.

For the purposes of isolation and purification it is also possible to use pharmaceutically unacceptable salts, for example perchlorates or picrates. Only the pharmaceutically acceptable salts, which are non-toxic when used correctly, can be used therapeutically and are therefore preferred.

The compounds of formula I have valuable pharmacological properties. They exhibit anti-retroviral activity, especially against the HIV-1 and HIV-2 viruses which are regarded as being pathogens of AIDS. The compounds of formula I wherein $R_1$ has the mentioned meanings with the exception of hydrogen, are, in warm-blooded animals, i.e. in the human or animal organism, convened into compounds of formula I wherein $R_1$ is hydrogen, for example by endogenous esterases or non-peptide-specific peptidases. The last-mentioned compounds of formula I are inhibitors of retroviral aspartate proteases, especially inhibitors of the aspartate protease of HIV-1 or HIV-2, and are accordingly suitable for the treatment of retroviral diseases, such as AIDS or its precursors (for example ARDS).

As a rule, compounds of formula I wherein $R_1$ has the mentioned meanings with the exception of hydrogen have especially advantageous pharmacodynamic properties, for example a higher bioavailability (especially when administered orally) than, and a kind of pharmacodynamics different from, that of compounds of formula I wherein $R_1$ is hydrogen.

The inhibitory action of compounds of formula I wherein $R_1$ is hydrogen on the proteolytic activity of HIV-1-protease can be demonstrated, for example, analogously to the method described by A. D. Richards et al., J. Biol. Chem. 265(14), 7733–7736 (1990). The inhibition of the action of HIV-1-protease (prepared in accordance with S. Billich et al., J. Biol. Chem. 263(34), 17905–17908 (1990)) is measured in the presence of the icosapeptide RRSN-QVSQNYPIVQNIQGRR (an artificial substrate of HIV-1 protease, prepared by peptide synthesis in accordance with known processes, cf. J. Schneider et al., Cell 54, 363–368 (1988)), which contains as substrate analogue one of the cleavage sites of the gag-precursor protein (natural substrate of HIV-1 protease). That substrate and its cleavage products are analysed by high pressure liquid chromatography (HPLC).

The active ingredient to be tested is dissolved in dimethyl sulfoxide. The enzymatic test is carried out by adding suitable dilutions of the inhibitor in 20 mM β-morpholinoethanesulfonic acid (MES)-buffer pH 6.0 to the test mixture, which comprises the above-mentioned icosapeptide (122 μM) in 20 mM MES buffer pH 6.0. 100 μl are used per test batch. The reaction is started by adding 10 μl of HIV-1-protease solution and is stopped after one hour's incubation at 37° C. by adding 10 μl of 0.3M $HClO_4$. After centrifugation of the sample at 10 000×g for 5 minutes, 20 μl of the resulting supernatant are applied to a 125×4.6 mm ®Nucleosil C18-5μ HPLC column (reversed-phase material supplied by Macherey & Nagel, Düren, FRG, based on silica gel covered with $C_{18}$-alkyl chains). The uncleaved icosapeptide and also its cleavage products are eluted from the column using the following gradient: 100% eluant 1–>50% eluant 1+50% eluant 2 (eluant 1:10% acetonitrile, 90% $H_2O$, 0.1% trifluoroacetic acid (TFA); eluant 2:75% acetonitrile, 25% $H_2O$, 0.08% TFA) for 15 minutes, throughflow rate 1 ml/minute. The quantification of the eluted peptide fragments is effected by measuring the peak height of the cleavage product at 215 nm.

The compounds exhibit inhibitory activity in the range of from $10^{-5}$ to $10^{-9}$M. $IC_{50}$ values ($IC_{50}$=the concentration that reduces the activity of HIV-1-protease by 50% in comparison with a control without an inhibitor) of approximately $5 \times 10^{-5}$ to $10^{-9}$M are preferably obtained.

In a further test it can be demonstrated that compounds of formula I wherein $R_1$ is hydrogen protect cells that will normally be infected by HIV from such an infection or at least retard such an infection. In that test, the human T-cell leukaemia cell line MT-2 (Science 229, 563 (1985)), which is extremely sensitive to the cytopathogenic effect of HIV because it is a continuous producer of HTLV-1 (a virus causing leukaemia), is used. The MT-2 cells are caused to grow in RPMI 1640 medium (Gibco, Scotland; RPMI comprises a mixture of amino acids without glutamine) supplemented with 10% heat-inactivated foetal calf serum, glutamine and standard antibiotics. In all cases the cells are free of mycoplasmas. The virus HIV-1 (strain LAV) is grown in A 3.01 cells (NIH, Bethesda, USA), a cell line used for growing HIV-1 and derived from the CEM cell line. The titre of the virus preparation is $2 \times 10^7$ IU/ml according to measurement by the test for reverse transcriptase (see below).

In order to measure the infection-inhibiting activity of the test compounds, 50 μl of the respective test compound in culture medium and 100 μl of HIV-1 in culture medium (800 TCID50/ml, TCID50=Tissue Culture Infective Dose=the dose that infects 50% of the MT-2 cells) are added to $10 \times 10^4$ exponentially growing MT-2 cells in 50 μl of culture medium in 96-well microtitre plates. After 4 days' incubation, a sample of 10 μl of the supernatant is taken from each well in order to measure the activity of the reverse transcriptase. The titre of the retrovirus-specific enzyme reverse transcriptase is used as the measurable variable for the virus titre. For that purpose, the samples taken are transferred to a further 96-well microliter plate and stored at −20° C. until measurement is carried out.

When the measurement is carded out, 30 μl of reverse transcriptase cocktail per well are added. The reverse transcriptase cocktail comprises 50 mM Tris (α,α,α-tris (hydroxymethyl)methylamine, Ultra pur, Merck, Gemany) pH 7.8; 75 mM KCl, 2 mM dithiothreitol, 5 mM $MgCl_2$; 0.05% Nonidet P-40 (detergent; Sigma, Switzerland). The mixture is filtered through a 0.45μAcrodisc filter (Gelman Sciences Inc., Ann Arbor, USA) and stored at −20° C. 0.1% (v/v) [alpha-$^{32}$P]dTTP is added before the test to aliquots of the solution in order to obtain a final radioactivity of 10 μCi/ml.

After mixing, the plate is incubated for 2 hours at 37° C. 5 μl of the reaction mixture are transferred to DE81 paper (Whatman, one filter per well). The dried filters are washed three times for 5 minutes with 300 mM NaCl/25 mM trisodium citrate and then once with ethanol and are again dried in the air. The radioactivity on the filters is measured in a Matrix Packard 96-well counter (Packard, Zurich, Switzerland). The ED90 values are calculated and are defined as the concentration of the test compound that reduces the RT activity by 90% in comparison with a control without a test compound.

The compounds of formula I wherein $R_1$ is hydrogen preferably exhibit an inhibition of virus replication at concentrations of from $10^{-5}$ to $10^{-8}$ M.

It is also possible to measure the level in the blood of compounds of formula I and especially of the HIV-1-protease-inhibiting compounds of formula I wherein $R_1$ is hydrogen.

For that purpose, the compounds of formula I to be investigated are dissolved, for example, in dimethyl sulfoxide (DMSO) in a concentration of 240 mg/ml. The resulting solutions are diluted with 20% (w/v) hydroxypropyl-β-cyclodextrin (HPβCD) in order to obtain a concentration of test compound of 12 mg/ml. That solution is administered to mice orally by artificial special feeding in a dose of 120 mg/kg. 60, 90 and 120 minutes after administration the animals are sacrificed and blood is removed. Three or four animals are investigated per time point. The blood is heparinised and prepared for analysis as follows: an internal standard is added to the heparinised blood in a final concentration of 4 μM. The blood is centrifuged. 0.25 ml of plasma is removed and deproteinised with an equal volume of acetonitrile. After centrifugation, the supernatant is concentrated to dryness by evaporation in vacuo and the residue is suspended in 20 μl of 3M NaCl solution and 100 μl of 0.05M phthalate buffer having a pH of 3.0. The suspension is extracted first with 1 ml and then with 0.2 ml of diisopropyl ether. The diisopropyl ether solution is concentrated to dryness by evaporation and the residue is dissolved in 50% (v/v) aqueous acetonitrile. The solution is investigated by reversed phase HPLC.

The analysis by reversed-phase HPLC is carried out using a 125×4.6 mm Nucleosil® $C_{18}$-column (reversed-phase material supplied by Macherey-Nagel, Düren, Federal Republic of Germany, based on silica gel derivatised with hydrocarbon radicals having 18 carbon atoms) equilibrated with a mobile phase of 50% acetonitrile in water/0.1% trifluoroacetic acid. The flow rate is 1 ml/minute. Detection is effected at 215 nm. Standards for the compounds in blood are worked up analogously to the blood samples and used to establish standard curves on the basis of which the in vivo concentrations are determined.

The compounds of formula I can also be used in the prevention, control and treatment of infections caused by retroviruses, especially HIV, such as HIV-1 or HIV-2, in cell cultures of mammalian cells, which is of particular advantage in the case of very valuable cell cultures which produce, for example, specific antibodies, vaccines or messenger substances, such as interleukins etc., and are accordingly of great commercial value.

Finally, the compounds of formula I can be used as standards in tests, for example as HPLC standards or as standards for comparing animal models in respect of various aspartate protease inhibitors, for example with regard to the level that can be obtained in the blood.

In the groups of compounds of formula I mentioned hereinafter, it is advantageously possible, for example in order to replace more general definitions by more specific definitions, to use definitions of substituents from the above-mentioned general definitions.

Preference is given to compounds of formula I wherein $R_1$ is lower alkanoyl; octanoyl, nonanoyl, decanoyl, undecanoyl, dodecanoyl, palmitoyl; lower alkenoyl; lower alkynoyl; substituted lower alkanoyl wherein the substituents are selected from up to three radicals from the group consisting of hydroxy, lower alkoxy, lower alkoxy-lower alkoxy, lower alkoxy-lower alkoxy-lower alkoxy, phenyl-lower alkoxy, naphthyl-lower alkoxy, phenyloxy-lower alkoxy wherein the phenyl radical may be unsubstituted or substituted by halogen up to three times, phenoxy, naphthyloxy, lower alkanoyloxy, phenyl-lower alkanoyloxy, halogen, carboxy, lower alkoxycarbonyl, phenyl-lower alkoxycarbonyl, carbamoyl, lower alkylcarbamoyl, hydroxy-lower alkyl-carbamoyl, di-lower alkylcarbamoyl, bis(hydroxy-lower alkyl)carbamoyl, cyano, oxo, $C_3$–$C_8$cycloalkyl, phenyl, naphthyl, $C_6$–$C_{12}$bicycloalkyl, $C_{9–C14}$tricycloalkyl, $C_4$–$C_8$cycloalkenyl, heterocyclyl that is unsubstituted or substituted by lower alkyl, mono-, di- or triphenyl-lower alkyl wherein phenyl is unsubstituted or lower alkoxy-substituted, lower alkanoyl, hydroxy, lower alkoxy, phenyl-lower alkoxy, phenyl-lower alkoxycarbonyl, hydroxy-lower alkyl, halogen, cyano and/or by trifluoromethyl and that is selected from pyrrolyl, 2,5-dihydropyrrolyl, furyl, thienyl, tetrahydrofuryl, cyclohepta[b]pyrrolyl, pyrrolidinyl, imidazolyl, imidazolidinyl, pyrazolinyl, pyrazolidinyl, triazolyl, tetrazolyl, tetrahydro-oxazolyl, tetrahydro-isoxazolyl, tetrahydro-thiazolyl, tetrahydro-isothiazolyl, indolyl, isoindolyl, quinolyl, isoquinolyl, benzimidazolyl, benzofuranyl, pyridyl, pyrimidinyl, pyrazinyl, piperidinyl, piperazin-1-yl, morpholino, thiomorpholino, S,S-dioxothiomorpholino, 1,2-dihydro- or 1,2,3,4-tetrahydro-quinolyl, and 1,2-dihydro- or 1,2,3,4-tetrahydro-isoquinolyl, and aryl selected from phenyl, naphthyl and fluorenyl, aryl being unsubstituted or mono- or poly-substituted by lower alkyl, halo-lower alkyl, halogen, hydroxy, lower alkoxy, lower alkanoyloxy, carboxy, lower alkyloxycarbonyl, phenyl-lower alkoxycarbonyl, carbamoyl, mono- or di-lower alkylcarbamoyl, mono- or di-hydroxy-lower alkylcarbamoyl, heterocyclyl-lower alkyl wherein heterocyclyl is as defined above as substituent of lower alkanoyl $R_1$ and is bonded via a ring nitrogen atom, by cyano and/or by nitro; or $R_1$ is an obtainable residue, bonded via the carbonyl of its carboxy group to the bonding oxygen atom, of an amino acid selected from glycine, alanine, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid, valine, norvaline, leucine, isoleucine, norleucine, serine, homoserine, threonine, methionine, cysteine, trans-3- and trans-4-hydroxyproline, phenylalanine, tyrosine, 4-aminophenylalanine, 4-chlorophenylalanine, 4-carboxyphenylalanine, β-phenylserine, phenylglycine, α-naphthylalanine, cyclohexylalanine, cyclohexylglycine, tryptophan, aspartic acid, asparagine, aminomalonic acid, aminomalonic acid monoamide, glutamic acid, glutamine, histidine, arginine, lysine, δ-hydroxylysine, ornithine, 3-aminopropanoic acid, α,γ-diaminobutyric acid and α,β-diaminopropionic acid, wherein an amino group is unsubstituted or mono- or di-N-alkylated by lower alkyl, by imidazolyl-lower alkyl, by pyridyl-lower alkyl, and/or by phenyl-lower alkyl, and/or N-acylated by unsubstituted or substituted lower alkanoyl, as defined above for lower alkanoyloxy $R_1$;

$R_2$, $R_3$, $R_4$ and $R_5$ are each independently of the others lower alkyl that is unsubstituted or substituted by up to four substituents selected from cycloalkyl that has from 3 to 7 carbon atoms; cycloalkenyl that has from 3 to 7 carbon atoms; bicycloalkyl that contains from 5 to 10 carbon atoms; bicycloalkenyl having from 8 to 12 carbon atoms; tricycloalkyl wherein tricycloalkyl contains from 8 to 10 carbon atoms; aryl selected from phenyl, indenyl, indanyl, naphthyl, anthryl, phenanthryl, acenaphthyl and fluorenyl, wherein aryl may be unsubstituted or, especially, substituted by one or up to three radicals selected from lower alkyl, halo-lower alkyl, phenyl, 1- or 2-naphthyl, hydroxy, lower alkoxy, phenyl-lower alkoxy wherein the phenyl radical may itself be unsubstituted or substituted by halogen, hydroxy or by lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, halogen, carboxy, lower alkoxycarbonyl, phenyl-, naphthyl- or fluorenyl-lower alkoxycarbonyl, lower alkanoyl, sulfo, lower alkylsulfonyl, phosphono, hydroxy-lower alkoxy-phosphoryl or di-lower alkoxyphosphoryl, carbamoyl, mono- or di-lower alkylcarbamoyl, sulfamoyl, mono- or di-lower alkylaminosulfonyl, nitro and cyano, wherein phenyl may be present once or up to three times; heterocyclyl selected from thienyl, furyl, pyrrolyl, imidazolyl, pyrazolyl, oxazolyl, thiazolyl, tetrazolyl, pyridyl, pyrazinyl, pyrimidinyl, pyridazinyl, indolyl, benzimidazolyl, quinolyl, isoquinolyl, 3,1-benzofuranyl, cyclohexa[b]pyrrolyl, cyclohexa[b]pyridyl, cyclohexa[b]pyrazinyl, cyclohexa[b]pyrimidinyl, pyrrolidinyl, pyrrolinyl, imidazolidyl, piperidyl, piperazinyl, morpholinyl, thiomorpholinyl, S,S-dioxo-thiomorpholinyl, indolinyl, iso-indolinyl, 4,5,6,7-tetrahydroindolyl, 1,2,3,4-tetrahydroquinolyl and 1,2,3,4-tetrahydroisoquinolyl, wherein heterocyclyl is unsubstituted or substituted by up to three substituents selected independently of one another from lower alkyl, phenyl, 1- or 2-naphthyl, phenyl-lower alkyl, hydroxy-lower alkyl, lower alkoxy-lower alkyl, lower alkanoyloxy-lower alkyl, phenyl- or naphthyl-lower alkanoyloxy-lower alkyl, lower alkoxycarbonyloxy-lower alkyl, phenyl-lower alkoxycarbonyloxy-lower alkyl, amino-lower alkyl, aminomethyl, hydroxy, lower alkoxy, amino, lower alkylamino, di-lower alkylamino, carboxy, lower alkoxycarbonyl, phenyl- or naphthyl-lower alkoxycarbonyl, halogen, lower alkanoyl, carbamoyl, mono- or di-lower alkylcarbamoyl, hydroxy- or carboxy-lower alkylcarbamoyl, nitro, oxo and cyano; hydroxy; hydroxy-lower alkoxy; lower alkoxy; lower alkoxy-lower alkoxy; lower alkoxy-lower alkoxy-lower alkoxy; lower alkoxy-lower alkoxy-lower alkoxy-lower alkyl; lower alkanoyloxy; lower alkanoyloxy-lower alkyl; amino; lower alkanoylamino; lower alkoxycarbonylamino; phenyl-lower alkoxycarbonylamino; amino substituted at the amino nitrogen atom by heterocyclyl-lower alkanoyl wherein heterocyclyl is as defined above as substituent of substituted lower alkyl independently of the radicals mentioned there; up to three halogen atoms; carboxy; lower alkoxycarbonyl; sulfonyl; carbamoyl; lower alkylcarbamoyl; di-lower alkylcarbamoyl; carbamoyl substituted at the nitrogen atom by a radical selected from ethylene, trimethylene, tetramethylene and pentamethylene wherein a carbon atom may have been replaced by nitrogen, oxygen, sulfur or sulfur mono- or di-substituted by oxygen; N-heterocyclyl-lower alkylcarbamoyl or N-lower alkyl-N-heterocyclyl-lower alkylcarbamoyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, each of which may also be completely or partially saturated, and from morpholinyl and thiomorpholinyl; oxo that is not in the 1-position of the alkyl radical; and from cyano; or $R_2$, $R_3$, $R_4$ and $R_5$ are each independently of the others lower alkenyl, such as allyl;

X together with the two bonds shown in formula I forms a bivalent radical selected from the group consisting of —(C=O)—, —(C=S)—, —(S=O)—, —(S(=O)$_2$)— and

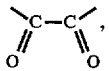

salts, especially pharmaceutically acceptable salts thereof.

Of the mentioned preferred compounds of formula I special preference is given to those wherein $R_1$ is hydrogen, X is a bivalent radical —(C=O)— and the remaining radicals are as defined, and pharmaceutically acceptable salts thereof.

Very preferred are compounds of formula I, especially of formula Ia or Ib, wherein $R_1$ is hydroxy, $R_2$, $R_3$, $R_4$ and $R_5$ are each independently of the others a radical selected from phenyl-lower alkyl, such as benzyl, naphthyl-lower alkyl, such as 1- or 2-naphthylmethyl, fluorophenyl-lower alkyl, such as 4-fluorobenzyl, cyclopropyl-lower alkyl, such as cyclopropylmethyl, cyclohexyl-lower alkyl, cyanophenyl-lower alkyl, such as 4-cyanobenzyl, lower alkoxyphenyl-lower alkyl, such as 4-isobutoxybenzyl or 4-methoxybenzyl, lower alkyl, such as n-propyl, isopropyl, isobutyl or n-butyl, and lower alkenyl, such as allyl, X together with the two bonds shown in formula I, preferably Ia, forms a bivalent radical —(C=O)—, —(C=S), —(S=O)— or —(S(=O)$_2$)—, especially —(C=O)—, and salts thereof.

Greatest preference is given to the compounds mentioned in the Examples, or pharmaceutically acceptable salts thereof.

PREPARATION PROCESSES

The compounds of formula I and salts of such compounds having at least one salt-forming group can be prepared in accordance with processes known per se, for example as follows:

a) for the preparation of compounds of formula I wherein $R_1$ is hydrogen and the remaining radicals are as defined, protecting groups present in a compound of formula II

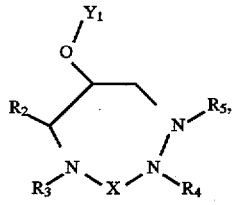

wherein $Y_1$ is a hydroxy-protecting group, other reactive groups are, if necessary, also in protected form and the remaining radicals are as defined for compounds of formula I, or in a salt thereof, are removed, or b) for the preparation of compounds of formula I wherein $R_1$ has one of the meanings mentioned for compounds of formula I with the exception of hydrogen, and $R_3$ and $R_4$ each have the same meaning, a compound of formula

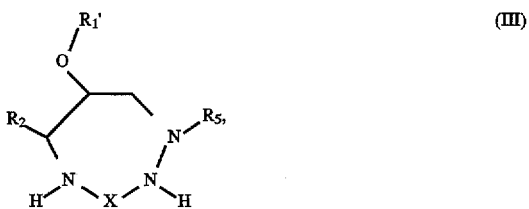 (III)

wherein $R_1'$ is as defined for $R_1$ in compounds of formula I with the exception of hydrogen, or a salt thereof, is alkylated with a compound of formula IV

R—L₁ (IV), wherein R is a radical as defined for $R_3$ and $R_4$ and $L_1$ is a nucleofugal leaving group, or c) for the preparation of compounds of formula I wherein $R_1$ has one of the mentioned meanings with the exception of hydrogen, and the remaining radicals are as defined, a compound of formula I wherein $R_1$ is hydrogen and the remaining radicals are as defined and, if necessary, other functional groups are in protected form is reacted with an acid of formula V $R_1'$—OH (V), wherein $R_1'$ is one of the radicals $R_1$ with the exception of hydrogen, or with a reactive acid derivative thereof, and, if necessary, protecting groups present are removed, and, if desired, a compound of formula I that is obtainable by one of the above processes a) to c) and has at least one salt-forming group is converted into its salt, or an obtainable salt is converted into the free compound or into a different salt and/or, if necessary, obtainable mixtures of isomers are separated and/or a compound of formula I according to the invention is converted into a different compound of formula I according to the invention.

The mentioned processes are described in more detail hereinafter. Unless otherwise indicated, hereinbefore and hereinafter the radicals $R_1, R_2, R_3, R_4, R_5, R_6, R_7$ and X are as defined for compounds of formula I.

Process a) (Removal Of Protecting Groups)

In starting materials of formula III, or salts thereof, other functional groups in addition to the hydroxy group protected by $Y_1$ may, independently of one another, be in protected form.

Those functional groups in starting materials the reaction of which is to be avoided, especially carboxy, amino, hydroxy, mercapto and sulfo groups, can be protected by suitable protecting groups (conventional protecting groups) which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis, etc.. In certain cases the protecting groups can additionally cause the reactions to proceed selectively, for example stereoselectively. It is characteristic of protecting groups that they can be removed easily, i.e. without undesired secondary reactions taking place, for example by solvolysis, reduction, photolysis, and also enzymatically, for example also under physiological conditions, and especially that they are not present in the end products.

The protection of functional groups by such protecting groups, the protecting groups themselves and the reactions for their introduction and removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie", Houben-Weyl, 4th edition, Volume 15/I, Georg Thieme Verlag, Stuttgart 1974, in H. -D. Jakubke and H. Jescheit, "Aminosäuren, Peptide, Proteine"("Amino acids, peptides, proteins"), Verlag Chemie, Weinheim, Deerfield Beach and Basle 1982, and in Jochen Lehmann, "Chemie der Kohlenhydrate: Monosaccharide und Derivate" ("The Chemistry of Carbohydrates: monosaccharides and derivatives"), Georg Thieme Verlag, Stuttgart 1974.

A carboxy group is protected, for example, in the form of an ester group which can be cleaved selectively under mild conditions. A carboxy group protected in esterified form is esterified especially by a lower alkyl group that is preferably branched in the 1-position of the lower alkyl group or substituted in the 1- or 2-position of the lower alkyl group by suitable substituents.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, for example tert-butoxycarbonyl.

A protected carboxy group esterified by a lower alkyl group that is substituted in the 1- or 2-position of the lower alkyl group by suitable substituents is, for example, arylmethoxycarbonyl having one or two aryl radicals, wherein aryl is phenyl that is unsubstituted or mono-, di- or trisubstituted, for example, by lower alkyl, for example tert-lower alkyl, such as tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di(4-methoxyphenyl)methoxycarbonyl, and also carboxy esterified by a lower alkyl group, the lower alkyl group being substituted in the 1- or 2-position by suitable substituents, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, as well as 2-(tri-substituted silyl)-lower alkoxycarbonyl wherein the substituents are each independently of the others an aliphatic, araliphatic, cycloaliphatic or aromatic hydrocarbon radical that is unsubstituted or substituted, for example, by lower aromatic, lower alkoxy, aryl, halogen and/or by nitro, for example lower alkyl, phenyl-lower alkyl, cycloalkyl or phenyl each of which is unsubstituted or substituted as above, for example 2-tri-lower alkylsilyl-lower alkoxycarbonyl, such as 2-tri-lower alkylsilylethoxycarbonyl, for example 2-trimethylsilylethoxycarbonyl or 2-(di-n-butyl-methyl-silyl)-ethoxycarbonyl, or 2-triarylsilylethoxycarbonyl, such as triphenylsilylethoxycarbonyl.

A carboxy group may also be protected in the form of an organic silyloxycarbonyl group. An organic silyloxycarbonyl group is, for example, a tri-lower alkylsilyloxycarbonyl group, for example trimethylsilyloxycarbonyl or tert-butyl-dimethylsilyloxycarbonyl. The silicon atom of the silyloxy-carbonyl group can also be substituted by two lower alkyl groups, for example methyl groups, and by an amino group or carboxy group of a second molecule of formula I. Compounds having such protecting groups can be prepared, for example, using dimethylchlorosilane as silylating agent.

A protected carboxy group is preferably tert-lower alkoxycarbonyl, for example tert-butoxycarbonyl, benzyloxycarbonyl, 4-nitrobenzyloxycarbonyl, 9-fluorenylmethoxycarbonyl or diphenylmethoxycarbonyl.

A protected amino group may be protected by an amino-protecting group, for example in the form of an acylamino, arylmethylamino, etherified mercaptoamino, 2-acyl-lower alk-1-enylamino or silylamino group or in the form of an azido group.

In a corresponding acylamino group, acyl is, for example, the acyl radical of an organic carboxylic acid having, for example, up to 18 carbon atoms, especially an unsubstituted or substituted, for example halo- or aryl-substituted, lower alkanecarboxylic acid or an unsubstituted or substituted, for example halo-, lower alkoxy- or nitro-substituted, benzoic acid, or, preferably, of a carbonic acid semiester. Such acyl groups are, for example, lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, unsubstituted or substituted, for example halo-, lower alkoxy- or nitro-substituted, benzoyl, such as benzoyl, 4-chlorobenzoyl, 4-methoxybenzoyl or 4-nitrobenzoyl, lower alkoxycarbonyl, preferably lower alkoxycarbonyl that is branched in the 1-position of the lower alkyl radical or suitably substituted in the 1- or 2-position, for example tert-lower alkoxycarbonyl, such as tert-butoxycarbonyl, arylmethoxycarbonyl having one, two or three aryl radicals which are phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl, 9-fluorenylmethoxycarbonyl or di(4-methoxyphenyl) methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(tri-substituted silyl)-lower alkoxycarbonyl, for example 2-tri-lower alkylsilyl-lower alkoxycarbonyl, such as 2-trimethylsilylethoxycarbonyl or 2-(di-n-butyl-methyl-silyl)-ethoxycarbonyl, or triarylsilyl-lower alkoxycarbonyl, for example 2-triphenylsilylethoxycarbonyl.

In an arylmethylamino group, for example a mono-, di- or especially tri-arylmethylamino group, the aryl radicals are especially unsubstituted or substituted phenyl radicals. Such groups are, for example, benzyl-, diphenylmethyl- or especially trityl-amino.

In an etherified mercaptoamino group the mercapto group is especially in the form of substituted arylthio or aryl-lower alkylthio, wherein aryl is, for example, phenyl that is unsubstituted or substituted, for example, by lower alkyl, such as methyl or tert-butyl, lower alkoxy, such as methoxy, halogen, such as chlorine, and/or by nitro, for example 4-nitrophenylthio.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoyl-prop-1-en-2-yl, such as 1-acetyl-prop-1-en-2-yl, or lower alkoxycarbonyl-lower alk-1-en-2-yl, for example lower alkoxycarbonyi-prop-1-en-2-yl, such as 1-ethoxycarbonyl-prop-1-en-2-yl.

A silylamino group is, for example, a tri-lower alkylsilylamino group, for example trimethylsilylamino or tert-butyl-dimethylsilylamino. The silicon atom of the silylamino group can also be substituted by only two lower alkyl groups, for example methyl groups, and by the amino group or carboxy group of a second molecule of formula I. Compounds having such protecting groups can be prepared, for example, using the corresponding chlorosilanes, such as dimethylchlorosilane, as silylating agents.

An amino group can also be protected by conversion into the protonated form; suitable corresponding anions are especially those of strong inorganic acids, such as sulfuric acid, phosphoric acid or hydrohalic acids, for example the chlorine or bromine anion, or of organic sulfonic acids, such as p-toluenesulfonic acid.

Preferred amino-protecting groups are lower alkoxycarbonyl, phenyl-lower alkoxycarbonyl, fluorenyl-lower alkoxycarbonyl, 2-lower alkanoyl-lower alk-1-en-2-yl and lower alkoxycarbonyl-lower alk-1-en-2-yl.

A hydroxy group, especially the OH-group in compounds of formula II which is protected by $Y_1$, can be protected, for example, by an acyl group, for example lower alkanoyl that is substituted by halogen, such as chlorine, such as 2,2-dichloroacetyl, or especially by an acyl radical of a carbonic acid semiester mentioned for protected amino groups. A preferred hydroxy-protecting group of that type is, for example, 2,2,2-trichloroethoxycarbonyl, 4-nitrobenzyloxycarbonyl, diphenylmethoxycarbonyl or triphenylmethoxycarbonyl. A hydroxy group may preferably be protected by tri-lower alkylsilyl, for example trimethylsilyl, triisopropylsilyl or tert-butyl-dimethylsilyl, a readily removable etherifying group, for example an alkyl group, such as left-lower alkyl, for example tert-butyl, an oxa- or a thia-aliphatic or -cycloaliphatic, especially 2-oxa- or 2-thia-aliphatic or -cycloaliphatic, hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, such as 2-tetrahydrofuryl or 2-tetrahydropyranyl, or a corresponding thia analogue, and also by 1-phenyl-lower alkyl, such as benzyl, diphenylmethyl or trityl, wherein the phenyl radicals can be substituted, for example, by halogen, for example chlorine, lower alkoxy, for example methoxy, and/or by nitro. The hydroxy-protecting group $Y_1$ is preferably one of the mentioned hydroxy-protecting groups with the exception of the acyl protecting groups, in order, if necessary, to avoid acyl migration, for example in intermediates having free amino or mercapto groups.

Two hydroxy groups, especially adjacent hydroxy groups, occurring in a molecule, or a hydroxy group and an amino group that are adjacent to one another, can be protected, for example, by bivalent protecting groups, such as a methylene group that is preferably substituted, for example, by one or two lower alkyl radicals or by oxo, for example unsubstituted or substituted alkylidene, for example lower alkylidene, such as isopropylidene, cycloalkylidene, such as cyclohexylidene, a carbonyl group or benzylidene.

A mercapto group, for example in cysteine, can be protected especially by S-alkylation with unsubstituted or substituted alkyl radicals, by silylation, by thioacetal formation, by S-acylation or by the formation of asymmetric disulfide groupings. Preferred mercapto-protecting groups are, for example, benzyl that is unsubstituted or substituted in the phenyl radical, for example by methoxy or by nitro, such as 4-methoxybenzyl, diphenylmethyl that is unsubstituted or substituted in the phenyl radical, for example by methoxy, such as di(4-methoxyphenyl)methyl, triphenylmethyl, pyridyldiphenylmethyl, trimethylsilyl, benzylthiomethyl, tetrahydropyranyl, acylaminomethyl, such as acetamidomethyl, isobutyrylacetamidomethyl or 2-chloroacetamidomethyl, benzoyl, benzyloxycarbonyl or alkyl-, especially lower alkyl-aminocarbonyl, such as ethylaminocarbonyl, and also lower alkylthio, such as S-ethylthio or S-tert-butylthio, or S-sulfo.

A sulfo group can be protected, for example, by lower alkyl, for example methyl or ethyl, by phenyl or in the form of a sulfonamide, for example in the form of an imidazolide.

In the context of this Application, a protecting group, for example a carboxy-protecting group, is to be understood as being expressly also a polymeric carrier that is bonded in a readily removable manner to the functional group, for example the carboxy group, to be protected, for example a carrier suitable for the Merrifield synthesis. Such a suitable polymeric carrier is especially a polystyrene resin that is weakly cross-linked by copolymerisation with divinylbenzene and that carries bridge members suitable for reversible bonding.

The removal of protecting groups that are not constituents of the desired end product of formula I, for example the carboxy-, amino-, hydroxy-, mercapto- and/or sulfo-protecting groups, is effected in a manner known per se, for example by means of solvolysis, especially hydrolysis, alcoholysis or acidolysis, or by means of reduction, especially hydrogenolysis or by chemical reduction, as well as photolysis, as appropriate in stages or simultaneously, it being possible also to use enzymatic methods. The removal of the protecting groups is described, for example, in the standard works mentioned hereinbefore in the section relating to protecting groups.

For example, protected carboxy, for example tert-lower alkoxycarbonyl, lower alkoxycarbonyl substituted in the 2-position by a trisubstituted silyl group or in the 1-position by lower alkoxy or by lower alkylthio, or unsubstituted or substituted diphenylmethoxycarbonyl can be converted into free carboxy by treatment with a suitable acid, such as formic acid, hydrogen chloride or trifluoroacetic acid, where appropriate with the addition of a nucleophilic compound, such as phenol or anisole. Carboxy can be freed from lower alkoxycarbonyl also by means of bases, such as hydroxides, for example alkali metal hydroxides, such as NaOH or KOH. Unsubstituted or substituted benzyloxycarbonyl can be converted to free carboxy, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. 2-(tri-substituted silyl)-lower alkoxycarbonyl, such as 2-tri-lower alkylsilyl-lower alkoxycarbonyl, can also be converted into free carboxy by treatment with a salt of hydrofluoric acid that yields the fluoride anion, such as an alkali metal fluoride, for example sodium or potassium fluoride, where appropriate in the presence of a macrocyclic polyether ("crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, for example a bis-lower alkane sulfine, such as dimethyl sulfoxide, or an N,N-di-lower alkyl-lower alkanoylamide, such as N,N-dimethylformamide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases, for example esterified arginine or lysine, such as lysine methyl ester, using trypsin.

A protected amino group is freed in a manner known per se and, according to the nature of the protecting groups, in various ways, preferably by solvolysis or reduction. Lower alkoxycarbonylamino, such as tert-butoxycarbonylamino, can be cleaved in the presence of acids, for example mineral acids, for example a hydrogen halide, such as hydrogen chloride or hydrogen bromide, or sulfuric or phosphoric acid, preferably hydrogen chloride, or strong organic acids, such as trihaloacetic acid, for example trifluoroacetic acid, or formic acid, in polar solvents, such as water, or ethers, preferably cyclic ethers, such as dioxane; 2-halo-lower alkoxycarbonylamino (where appropriate after conversion of a 2-bromo-lower alkoxycarbonylamino group into a 2-iodo-lower alkoxycarbonylamino group) or aroylmethoxycarbonylamino or 4-nitrobenzyloxycarbonylamino directly dissolved in a liquid organic carboxylic acid, such as formic acid, can be cleaved, for example, by treatment with a suitable reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-(tri-substituted silyl)-lower alkoxycarbonylamino, such as 2-tri-lower alkylsilyl-lower alkoxycarbonylamino, can be cleaved by treatment with a suitable acid, for example formic acid or trifluoroacetic acid; unsubstituted or substituted benzyloxycarbonylamino can be cleaved, for example, by means of hydrogenolysis, i.e. by treatment with hydrogen in the presence of a suitable hydrogenation catalyst, such as a platinum or palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water; and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting substitution product; amino is freed from trifluoroacetylamino, for example, by hydrogenolysis with bases, such as alkali metal hydroxides or carbonates, such as $Na_2CO_3$ or $K_2CO_3$, in polar solvents, for example alcohols, such as methanol, at temperatures of from 0° to 100° C., especially from 40° to 80° C. An amino group protected by 2-(tri-substituted silyl)-lower alkoxycarbonyl, such as 2-tri-lower alkylsilyl-lower alkoxycarbonyl, can be converted into the free amino group also by treatment with a salt of hydrofluoric acid that yields fluoride anions, as indicated above in connection with the freeing of a correspondingly protected carboxy group under conditions analogous to those mentioned there. Likewise, silyl, such as trimethylsilyl, bonded directly to a hetero atom, such as nitrogen, can be removed using fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carried out in an inert solvent, such as a halogenated hydrocarbon, for example methylene chloride, or in water or in a mixture of water and an organic solvent, such as an alcohol or dioxane, at approximately from 20° C. to 25° C., or with cooling or heating.

A hydroxy or mercapto group protected by a suitable acyl group, by a tri-lower alkylsilyl group or by unsubstituted or substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group protected by tert-lower alkyl or by a 2-oxa- or 2-thia-aliphatic or -cycloaliphatic hydrocarbon radical, is freed by acidolysis, for example by treatment with a mineral acid or a strong carboxylic acid, for example trifluoroacetic acid. Mercapto protected by pyridyl-diphenylmethyl can be freed, for example, using mercury(II) salts at pH 2–6 or by zinc/acetic acid or by electrolytic reduction; acetamidomethyl and isobutyrylamidomethyl can be freed, for example, by reaction with mercury(II) salts at pH 2–6; 2-chloroacetamidomethyl can be freed, for example, using 1-piperidinothiocarboxamide; and S-ethylthio, S-tert-butylthio and S-sulfo can be freed, for example, by thiolysis with thiophenol, thioglycolic acid, sodium thiophenolate or 1,4-dithiothreitol. Two hydroxy groups or an adjacent amino and hydroxy group which are protected together by means of a bivalent protecting group, preferably, for example, by a methylene group mono- or di-substituted by lower alkyl, such as lower alkylidene, for example isopropylidene, cycloalkylidene, for example cyclohexylidene, or benzylidene, can be freed by acid solvolysis, especially in the presence of a mineral acid or a strong organic acid. A tri-lower alkylsilyl group is likewise removed by acidolysis, for example by a mineral acid, preferably hydrofluoric acid, or a strong carboxylic acid, or by treatment with a salt of hydrofluoric acid that yields the fluoride anion, such as an alkali metal fluoride, for example sodium or potassium fluoride, where appropriate in the presence of a macrocyclic polyether (crown ether), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic polar solvent, for example a bis-lower alkane sulfine, such as dimethyl sulfoxide, or an N,N-di-lower alkyl-lower alkanoylamide, such as N,N-dimethylformamide or N,N-dimethylacetamide. 2-halo-lower alkoxycarbonyl is removed using the above-mentioned reducing agents, for example a reducing metal, such as zinc, reducing metal salts, such as chromium(II) salts, or using sulfur compounds, for example sodium dithionite or preferably sodium sulfide and carbon disulfide.

A sulfo group protected in the form of a sulfonic acid ester or sulfonamide is freed, for example, by acid hydrolysis, for example in the presence of a mineral acid, or preferably by basic hydrolysis, for example with an alkali metal hydroxide or an alkali metal carbonate, for example sodium carbonate.

When several protected functional groups are present, if desired the protecting groups can be so selected that more than one such group can be removed simultaneously, for example by acidolysis, such as by treatment with trifluoroacetic acid, or with hydrogen and a hydrogenation catalyst, such as a palladium-on-carbon catalyst. Conversely, the groups can also be so selected that they cannot all be removed simultaneously, but rather are removed in a desired sequence, the corresponding, partially protected intermediates being obtained.

In general, protecting groups are so chosen that acyl migration from acyl protecting groups does not take place to an unacceptable extent.

Generally, the removal of protecting groups is preferably carried out at temperatures of from approximately 0° C. to reflux temperature, especially from 10° to 40° C., for example at approximately room temperature, or also at reflux temperature.

Process b) (Alkylation)

In compounds of formulae III and IV, functional groups that are not intended to participate in the reaction, and also those which interfere under the reaction conditions, may, if necessary, be protected independently of one another by protecting groups mentioned under Process a).

Preferred as starting materials of formula III are those of formula IIIa or IIIb,

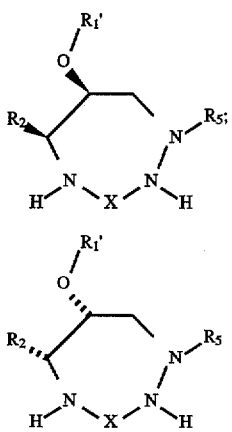

(IIIa)

(IIIb)

wherein the radicals are as defined for compounds of formula III.

A nucleofugal leaving group $L_1$ is, especially, selected from hydroxy esterified by a strong inorganic or organic acid, such as hydroxy esterified by a mineral acid, for example a hydrohalic acid, such as hydrochloric acid, hydrobromic acid or hydriodic acid, or by a strong organic sulfonic acid, such as an unsubstituted or substituted, for example halo-, such as fluoro-, substituted, lower alkanesulfonic acid, or an aromatic sulfonic acid, for example a benzenesulfonic acid that is unsubstituted or substituted by lower alkyl, such as methyl, halogen, such as bromine, and/or by nitro, for example a methanesulfonic acid, p-bromotoluenesulfonic acid or p-toluenesulfonic acid, or hydroxy esterified by hydrazoic acid.

Alkylation is effected in accordance with customary methods in the presence of a base, especially a suitable strong base, for example an alkali metal di-lower alkylamide, such as lithium diisopropylamide, an alkali metal hydride, such as lithium, sodium or potassium hydride, or an alkali metal amide, such as lithium or sodium amide, each of which may also be added in the form of a dispersion in oil or in an aliphatic hydrocarbon, such as hexane, at preferred temperatures of from $-10°$ C. to reflux temperature, especially from room temperature to reflux temperature, for example approximately at room temperature, in aprotic, especially polar, solvents, such as acid amides, for example dimethylformamide, a urea derivative, such as 1,3-dimethyl-3,4,5,6-tetrahydro-2(1H)-pyrimidinone (DMPU), or a hexa-lower alkylphosphoric acid triamide, such as hexamethylphosphoric acid triamide, or mixtures of such solvents, in the presence or absence of a protective gas, such as argon or nitrogen it being possible when alkali metal amides are used as bases to remove ammonia formed during the reaction by applying a vacuum of, for example, from 0.001 to $0.2 \times 10^5$, especially from 0.005 to $0.02 \times 10^{-5}$, Pascal.

The freeing of protected groups is effected, where appropriate, in accordance with the methods described under Process a) (removal of protecting groups).

Process c) Acylation:

In compounds of formula I wherein $R_1$ is hydrogen and the remaining radicals are as defined, and in acids of formula V, or the reactive derivatives thereof, functional groups that are not intended to participate in the reaction or that could interfere with the reaction, are protected independently of one another by protecting groups mentioned under Process a).

The acylation of the hydroxy group is effected, for example, in a manner known per se using a free acid of formula V as defined above or a salt thereof wherein $R_1'$ is as defined with the exception of unsubstituted or substituted aminocarbonyl, or a reactive derivative of a compound of formula V wherein $R_1'$ is as defined for $R_1$ in compounds of formula I with the exception of hydrogen. A suitable reactive derivative is, for example, a carboxylic acid of formula Va $$R_1'-Z_1 \quad \text{(Va)}$$

wherein $R_1'$ is one of the radicals $R_1$ mentioned above for compounds of formula I with the exception of hydrogen, preferably one of the radicals mentioned with the exception of unsubstituted or substituted aminocarbonyl, and wherein $Z_1$ is reactively activated hydroxy (the compound of formula Va therefore contains, instead of a hydroxy function bonded to the carbonyl group, reactively activated hydroxy, preferably as defined below). The free carboxylic acid of formula V can be activated, especially also in situ, for example, by strong acids, such as a hydrohalic, sulfuric, sulfonic or carboxylic acid, or acidic ion exchangers, for example by hydrochloric, hydrobromic or hydriodic acid, sulfuric acid, an unsubstituted or substituted, for example halosubstituted, alkanecarboxylic acid, or by an acid of formula V, preferably with an excess of the acid of formula V, if necessary with the binding of the resulting water of reaction by water-binding agents, with removal of the water of reaction by azeotropic distillation or with extractive esterification, by acid anhydrides, especially inorganic or more especially organic acid anhydrides, for example carboxylic acid anhydrides, such as lower alkanecarboxylic acid anhydrides (with the exception of formic acid anhydride), for example acetic anhydride, or by suitable activating or coupling reagents of the type mentioned below. $R_1'-Z_1$ may especially also be a carboxylic acid azide ($Z_1$=azido; obtainable, for example, by reaction of a corresponding acid ester via the corresponding hydrazide and treatment thereof with nitrous acid); a carboxylic acid halide ($Z_1$=halogen, especially chlorine or bromine), especially an acid chloride or bromide, obtainable, for example, by reaction with organic acid halides, especially with oxalyl dihalides, such as oxalyl dichloride, with inorganic acid halides, for example with acid halides of phosphorus or sulfur, such as phosphorus trichloride, phosphorus tribromide, phosphorus pentachloride, phosphorus pentabromide, phosphorus oxychloride, phosphorus oxybromide, thionyl chloride or thionyl bromide, or especially under mild conditions with tetra-lower alkyl-α-halo-enamines, for example tetramethyl-α-halo-enamines, especially 1-chloro-N,N,2-trimethyl-1-propeneamine (preferably by reaction under an inert gas, such as nitrogen, in inert solvents, especially chlorinated hydrocarbons, such as methylene chloride or chloroform, or ethers, such as diethyl ether, dioxane or tetrahydrofuran, or mixtures thereof, at preferred temperatures of from $-78°$ to $50°$ C., especially from $-60°$ to $30°$ C., for example from $-10°$ C. to room temperature (cf. Devos, A., et al., J. C. S. Chem. Commun. 1979, 1180–1181, and Haveaux, B., et al., Org. Synth. 59, 26 (1980))), it being possible for the resulting acid halide, for example the acid chloride of formula Va wherein $Z_1$ is chlorine, also to be used further directly in situ, for example by reaction with the compound of formula I wherein $R_1$ is hydrogen and the remaining radicals are as defined, in the presence of tertiary nitrogen bases, such as pyridine or 4-dimethylaminopyridine (DMAP, which is preferably added in catalytic amounts) or both of those bases, at preferred temperatures of from $-20°$ to $50°$ C., especially from $10°$ C. to $40°$ C.; an activated ester wherein $Z_1$ is the radical of an alcohol having electron-attracting substituents, especially cyanomethoxy or aryloxy wherein aryl is preferably phenyl or naphthyl that is mono- or poly-substituted by halogen, nitro and/or by cyano, for example nitrophenoxy, such as 4-nitrophenoxy or 2,4-dinitrophenoxy, or polyhalophenoxy, such as pentachlorophenoxy; or a symmetrical or, preferably, asymmetrical acid anhydride which can be obtained, for example, by the action of a salt, for example an alkali metal salt, of an acid of formula V or its reaction partner, preferably a lower alkanecarboxylic acid, such as acetic acid, such as the sodium or potassium salt, on a complementary acid halide, and especially, in the case of the reaction with a salt of a carboxylic acid of formula V, a carboxylic acid halide, for example chloride, such as acetyl chloride, and, in the case of the reaction of a carboxylic acid halide of formula Va wherein $Z_1$ is halogen, for example chlorine or bromine, with a salt of a lower alkanecarboxylic acid, especially sodium or potassium acetate. There may be used as activating and coupling reagents for activating carboxylic acids of formula V in situ also carbodiimides, for example N,N'-di-$C_1$–$C_4$alkyl- or N,N'-di-$C_5$–$C_7$cycloalkyl-carbodiimide, such as diisopropylcarbodiimide or N,N'-dicyclohexylcarbodiimide, advantageously with the addition of an activating catalyst, such as N-hydroxysuccinimide or unsubstituted or substituted, for example halo-, $C_1$–$C_7$alkyl- or $C_1$–$C_7$alkoxy-substituted, N-hydroxy-benzotriazole or N-hydroxy-5-norbornene-2,3-dicarboxamide, $C_1$–$C_4$alkyl haloformate, for example isobutyl chloroformate, suitable carbonyl compounds, for example N,N-carbonyldiimidazole, suitable 1,2-oxazolium compounds, for example 2-ethyl-5-phenyl-1,2-oxazolium 3'-sulfonate or 2-tert-butyl-5-methyl-isoxazolium perchlorate, suitable acylamino compounds, for example 2-ethoxy-1-ethoxycarbonyl-1,2-dihydroquinoline, or suitable phosphoryl cyanamides or azides, for example diethylphosphoryl cyanamide or diphenylphosphoryl azide, also triphenylphosphine disulfide or 1-$C_1$–$C_4$alkyl-2-halopyridinium halides, for example 1-methyl-2-chloropyridinium iodide. The compound of formula Va can also be a corresponding lower alkylthio ester ($Z_1$=lower alkylthio).

If two free carboxy groups are present in the compound of formula V it is also possible for an internal anhydride to be present as activated acid derivative.

$Z_1$ is preferably halogen, such as chlorine or bromine, and also acyloxy, for example lower alkanoyloxy, such as acetyloxy.

The reaction with an acid halide, such as an acid chloride, of formula Va ($Z_1$=Cl) is carried out especially in an ether, such as dioxane, tetrahydrofuran, or a nitrile, such as acetonitrile, or mixtures thereof, in the presence or absence of pyridine and in the absence or, preferably, in the presence of tertiary nitrogen bases, such as 4-dimethylaminopyridine, ethyl diisopropylamine, triethylamine or mixtures of two or more of those bases, with or without a protective gas, such as argon, at temperatures of from 0° to 80° C. or the reflux temperature, for example from room temperature to 50° C. or the reflux temperature if that is lower than 50° C.

For the specific case of the introduction of an acyl radical of a semiester of carbonic acid linked via its carbonyl group to the bonding oxygen atom, there are suitable especially the compounds of formula Va wherein $Z_1$ is halogen, such as chlorine, which can be prepared, for example, by reaction of the complementary alcohols, for example unsubstituted or substituted alkyl alcohols, aryl-lower alkyl alcohols or heterocyclyl-lower alkyl alcohols, which after removal of the hydroxy-hydrogen yield, together with the bonding carbonyl group, unsubstituted or substituted alkoxycarbonyl, aryl-lower alkyloxycarbonyl or heterocyclyl-lower alkyloxycarbonyl $R_1$, as defined above, with phosgene or analogues thereof that contain instead of chlorine other halogen atoms, especially bromine, preferably in the presence of tertiary nitrogen bases, such as pyridine or triethylamine, and in inert solvents, for example chlorinated hydrocarbons, such as methylene chloride or chloroform, ethers, such as diethyl ether, tetrahydrofuran or dioxane, or carboxylic acid amides, such as dimethylformamide. Also suitable are corresponding N-carbonylazolides of formula Va ($Z_1$=N-containing heterocycle, such as 1-imidazolido) instead of phosgene, which are obtained, for example, by reaction with the corresponding N,N'-carbonyldiazolides, such as N,N'-carbonyldiimidazole, under the conditions just described for phosgene and analogues having other halogen atoms. The reaction of compounds of formula II with the corresponding compounds of formula IX is then likewise carried out under those conditions (cf. Staab, H. A., Angew. Chemie 74, 407 (1962)).

For the specific case wherein $R_1$ in formula I is an unsubstituted or substituted aminocarbonyl group, there are suitable for the introduction of the corresponding radical $R_1$ in the reaction with compounds of formula I wherein $R_1$ is hydrogen, especially the compounds of formula Va wherein $Z_1$ is halogen, such as chlorine, and wherein $R_1'$ is unsubstituted or substituted aminocarbonyl, which can be prepared, for example, by reaction of the complementary amines, for example unsubstituted or substituted lower alkylamines, which, after removal of a hydrogen atom, yield a radical selected from unsubstituted and substituted lower alkyl as defined above as substituent of aminocarbonyl $R_1$, or arylamines, which yield an arylaminocarbonyl radical, as defined in the definition of unsubstituted or substituted aminocarbonyl $R_1$ with phosgene or analogues thereof that contain instead of chlorine other halogen atoms, especially bromine, preferably in the presence of tertiary nitrogen bases, such as pyridine or triethylamine, and in inert solvents, for example chlorinated hydrocarbons, such as methylene chloride or chloroform, ethers, such as diethyl ether, tetrahydrofuran or dioxane, or carboxylic acid amides, such as dimethylformamide. Also suitable are corresponding N-carbonylazolides of formula Va ($Z_1$=N-containing heterocycle, such as 1-imidazolido) which are obtained, for example, by reaction with the corresponding N,N'-carbonyldiazolides, such as N,N'-carbonyldiimidazole, under the conditions just described for phosgene and analogues having other halogen atoms. The reaction of compounds of formula I wherein $R_1$ is hydroxy with the corresponding compounds of formula Va is then likewise carried out under those conditions (cf. Staab, H. A., Angew. Chemie 74, 407 (1962)).

For the specific case of the introduction of aminocarbonyl $R_1$ or an N-monosubstituted aminocarbonyl group $R_1$ there is suitable as activated acid derivative especially the corresponding isocyanate of formula Vb

  (Vb)

wherein Q is an amino-protecting group, for example trihaloacetyl, such as trifluoro- or trichloro-acetyl, or one of the unsubstituted or substituted lower alkyl radicals or aryl radicals mentioned above in the definition of unsubstituted or substituted aminocarbonyl $R_1$, it being possible, when Q is an amino-protecting group, to obtain after the reaction with the compound of formula I wherein $R_1$ is hydrogen the corresponding compound of formula I wherein $R_1$ is free aminocarbonyloxy, by removal of the protecting group Q, as described for the freeing of amino protected by acyl under Process a), especially by acid hydrolysis, or, when Q is one of the mentioned substituted or unsubstituted lower alkyl radicals or aryl radicals, a corresponding compound of formula I containing amino-carbonyl $R_1$ monosubstituted at the nitrogen atom. Both aminocarbonyl and N-monosubstituted aminocarbonyl $R_1$ can be converted into N-disubstituted aminocarbonyl $R_1$ by alkylation with a further unsubstituted or substituted lower alkyl radical using suitable starting materials and conditions analogous to those described below under "Additional Process Steps".

The mentioned reactions can be carried out under reaction conditions known per se, at customary temperatures, in the presence or, especially when lower alkanoyl anhydrides are used to activate the carboxylic acid of formula V, in the absence of inert solvents or diluents, for example in acid amides, for example N,N-di-lower alkyl-lower alkanecarboxylic acid amides, such as dimethylformamide, dimethylacetamide or 1,3-dimethyl-3,4,5,6-tetrahydro-2(1H)-pyrimidinone (DMPU), or amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as ethyl acetate, bis-lower alkane sulfines, such as dimethyl sulfoxide, nitrogen heterocycles, such as pyridine, or mixtures of those solvents, especially in anhydrous solvents or solvent mixtures, it being possible to select for the above-mentioned reactions the particular solvents that are suitable in each case, there being used, as appropriate and expedient, salts of the compounds used, especially metal salts of carboxylic acids that are used, such as the alkali metal or alkaline earth metal salts, for example sodium or potassium salts, in the absence or the presence of catalysts, such as dimethylaminopyridine, condensation agents or neutralising agents, such as tertiary nitrogen bases, for example pyridine, triethylamine, N-methylmorpholine, 4-dimethylaminopyridine or ethyl diisopropylamine, and, depending on the nature of the reaction and/or the reactants, under atmospheric pressure or in a closed vessel, under normal pressure or under elevated pressure, for example at the pressure produced in the reaction mixture under the reaction conditions in a closed tube, and/or in an inert atmosphere, for example under an argon or nitrogen atmosphere. Preference is given to reaction conditions that are mentioned specifically in any particular case or, especially, that are analogous to those mentioned in the Examples. The course of the reaction is advantageously monitored using customary methods of analysis, especially using thin-layer chromatography. From those reaction conditions it is possible to select the reaction conditions that are suitable for each of the reactions described in this text, reaction conditions that are specifically mentioned being especially preferred.

The reaction according to the invention is preferably carried out under mild conditions, especially at temperatures of from −10° to 60° C., for example from 0° C. to room temperature or at slightly elevated temperatures up to about 50° C., for example approximately from 0° C. to 40° C., especially at room temperature. Both in the case of the reaction with a carboxylic acid halide of formula Va wherein $Z_1$ is halogen, such as chlorine or bromine, and in the case of the reaction with an anhydride, especially a symmetrical anhydride ($Z_1$=O—$R_1$'), the corresponding compound of formula Va (halide and $R_1$'—O—$R_1$', respectively) is used especially in an approximately equimolar amount in relation to the compound of formula I or in excess, for example from 0.95 to 10 times the molar amount, preferably from 1.05 to 5 times the molar amount.

ADDITIONAL PROCESS STEPS

In the additional process steps, which are optional, functional groups of the starting compounds that are not intended to participate in the reaction may be unprotected or may be in protected form, for example they may be protected by one or more of the protecting groups mentioned above under Process a). The protecting groups may be retained in the end products or some or all of them may be removed in accordance with one of the methods mentioned under Process a).

Salts of compounds of formula I having at least one salt-forming group may be prepared in a manner known per se. For example, salts of compounds of formula I having acidic groups may be formed, for example, by treatment with metal compounds, such as alkali metal salts of suitable organic carboxylic acids, for example the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, for example by treatment with an acid or a suitable anion exchange reagent. Internal salts of compounds of formula I containing acidic and basic salt-forming groups, for example a free carboxy group and a free amino group, may be formed, for example, by the neutralisation of salts, such as acid addition salts, to the isoelectric point, for example with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent. The free compounds of formula I can then for their part be converted into other salts by the methods just mentioned for the preparation of salts of compounds of formula I.

Mixtures of stereoisomers, i.e. mixtures of diastereoisomers and/or enantiomers, such as, for example, racemic mixtures, can be separated into the corresponding isomers in a manner known per se by suitable separating processes. For example, mixtures of diastereoisomers can be separated into the individual diastereoisomers by fractional crystallisation, chromatography, solvent partition etc.. Racemates can be separated from one another, after conversion of the optical antipodes into diastereoisomers, for example by reaction with optically active compounds, for example optically active acids or bases, by chromatography on column materials covered with optically active compounds or by enzymatic methods, for example by selective reaction of only one of the two enantiomers. This separation can be carried out either at the stage of one of the starting materials or intermediates or with the compounds of formula I themselves.

In a compound of formula I, an aryl radical, especially a phenyl radical, in $R_1$, $R_2$, $R_3$, $R_4$, $R_5$, $R_6$ and/or $R_7$ can be hydrogenated, for example by catalytic hydrogenation, especially in the presence of heavy metal oxides, such as rhodium/platinum mixed oxides, for example with the Nishimura catalyst, preferably in a polar solvent, such as an alcohol, for example methanol or ethanol, at temperatures of from 0° to 80° C., especially from 10 to 40° C., and at a hydrogen pressure of from 1 to 10 atm, preferably at approximately normal pressure.

In compounds of formula I wherein at least one of the radicals $R_2$, $R_3$, $R_4$ and $R_5$ is alkenyl, the double bond can be reduced, especially by selective hydrogenation in the presence of catalyst, for example noble metal catalysts, such as platinum or especially palladium, which are present in free form or preferably bonded to a carrier, such as aluminium oxide or, especially, carbon, such as activated carbon. The hydrogenation is carried out preferably in a polar organic solvent, such as an alcohol, for example methanol or ethanol, at temperatures of from −10° to 60° C., especially at approximately room temperature.

In an obtainable compound of formula I wherein X is the radical —(C=O)— and the remaining radicals are as defined, the radical X, which has the meaning —(C=O)—, (and/or one or more of any other carbonyl groups that may be present in the molecule) can be converted into the corresponding thiocarbonyl radical —(C=S)—. The reaction is effected, for example, by reacting the corresponding oxo compound of formula I with phosphorus pentasulfide or preferably phosphorus pentasulfide substitutes, such as Laweson's reagent (=2,4-bis(4-methoxyphenyl)-2,4-dithioxo-1,2,3,4-dithiaphosphetane), the reaction being carried out in inert organic solvents, for example in a halogenated hydrocarbon, such as carbon tetrachloride, chloroform or dichloromethane, at temperatures of from 30° C. to reflux temperature, especially under reflux.

In an obtainable compound of formula I, an unsubstituted or monosubstituted amino-carbonyl group, for example unsubstituted or monosubstituted aminocarbonyl $R_1$, can be alkylated.

The alkylation for the introduction of unsubstituted or substituted alkyl as defined for N-substituted aminocarbonyl $R_1$ is carried out, for example, by alkylation with suitable starting materials.

Suitable starting materials for the alkylation of a carboxamide group in a compound of formula I are, for example, diazo compounds, such as diazomethane. Diazomethane can be decomposed in an inert solvent, the free methylene formed reacting with the carboxamide group in the compound of formula I. The decomposition of diazomethane is effected preferably catalytically, for example in the presence of a noble metal in freely divided form, such as copper, or in the presence of a noble metal salt, for example copper(I) chloride or copper(II) sulfate.

Other alkylating agents are compounds of formula VI $$A—L_2 \qquad (VI)$$

wherein A is unsubstituted or substituted alkyl as defined as substituent in substituted aminocarbonyl $R_1$, and $L_2$ is a nucleofugal leaving group as defined for $L_1$ in compounds of formula IV. The reaction is carried out preferably in the presence of bases under conditions analogous to those mentioned for the reaction of compounds of formula III with those of formula IV (Process b)).

The acylation according to Process c) (introduction of acyl radicals $R_1$ in place of hydrogen $R_1$ in compounds of formula I) can also be regarded as a conversion.

A preferred conversion is that of a stereoisomer of a compound of formula I into a different stereoisomer. For example, it is possible to convert a compound of formula Ia wherein $R_1$ is hydrogen into a compound of formula Ib as defined above (but wherein $R_1$=hydrogen) and/or into a compound of formula Ic or Id

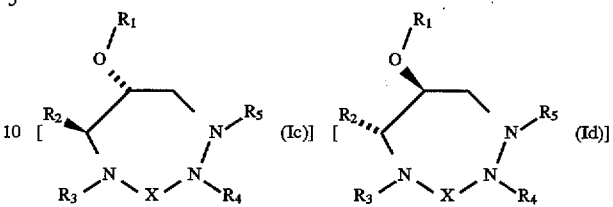

wherein $R_1$ is hydrogen and the remaining radicals are as defined in the definition of compounds of formula I, or analogously to convert a compound of formula Ib wherein $R_1$ is hydrogen into a compound of formula Ia as defined above (but wherein $R_1$=hydrogen) and/or into a compound of formula Ic or Id, as just described.

The conversion is effected preferably by oxidative conversion of the group $R_1$—O— (=H—O—) in the corresponding starting compound of formula Ia or Ib into the corresponding oxo group (O=) of formula Ie or If

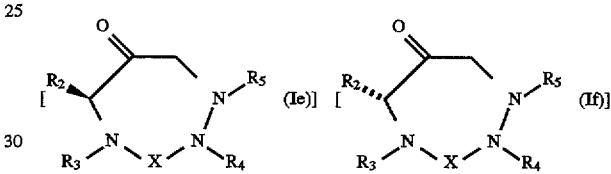

wherein the radicals are as defined, and subsequent racemisation of the $R_2$ carrying carbon atom and finally reduction of the oxo group (O=) to the group $R_1$—O— (=H—O—), and, if desired, separation of mixtures of diastereoisomers formed into the individual diastereoisomers (cis- and trans-isomer, each of which may also be in the form of a racemate which can be further separated into the individual enantiomers).

The oxidative conversion is effected by suitable oxidising agents, especially by Swern Oxidation (use of a combination of oxalyl chloride and dimethyl sulfoxide as oxidising agent in suitable solvents, such as halogenated hydrocarbons, for example methylene chloride, chloroform or tetrachloromethane, at preferred temperatures of from −30° to −78° C., especially approximately −60° C., preferably under a protective gas.

The subsequent racemisation of the oxo compound formed is effected preferably with a suitable strong base, such as 1,5,7-triazabicyclo[4.4.0]dec-5-ene or also a metal alcoholate, such as an alkali metal alcoholate, for example sodium methoxide or ethoxide, in suitable inert solvents, such as ethers, for example diethyl ether or cyclic ethers, such as dioxane or especially tetrahydrofurnn, at preferred temperatures of from 0° to 50° C., especially at approximately room temperature, preferably under a protective gas and in the presence of only catalytic amounts of the suitable strong base (for example in the range of from 1/10 to 1/50 of the molar mount of the oxo compound).

The final reduction of the oxo compound to the corresponding hydroxy compound of formula I (which is obtained in the form of a mixture of isomers) is effected with a suitable hydrogenation agent, especially a suitable complex hydride, for example $LiAlH[OC(CH_3)_3]_3$ or also bis (3-methyl-but-2-yl)borane in an ether, such as tetrahydrofuran, or preferably sodium borohydride in an alcohol, such as a lower alkanol, for example methanol or ethanol, at preferred temperatures of from 0° to 50° C., for example at approximately room temperature.

The separation of the isomers can be effected as described above; for example, mixtures of diastereoisomers can be separated into the corresponding diastereoisomers by column chromatography on $SiO_2$.

GENERAL PROCESS CONDITIONS

Owing to the close relationship between the compounds of formula I and their salts and starting materials (starting compounds and intermediates) in free form and in the form of their salts, hereinbefore and hereinafter any reference to the free compounds or their salts is to be understood as including also the corresponding salts or free compounds, respectively, as appropriate and expedient.

All the process steps hereinbefore and hereinafter can be carried out under reaction conditions known per se, preferably the reaction conditions specifically mentioned, in the absence or, usually, in the presence of solvents or diluents, preferably those solvents or diluents which are inert towards the reagents used and are solvents therefor, in the absence or presence of catalysts, condensation agents or neutralising agents, for example ion exchangers, such as cation exchangers, for example in the $H^+$ form, and depending upon the nature of the reaction and/or the reactants, at reduced, normal or elevated temperature, for example in a temperature range of from approximately −100° C. to approximately 190° C., preferably from approximately −80° C. to approximately 150° C., for example at from −80° to −60° C., at room temperature, at from −20° to 40° C. or at reflux temperature, under atmospheric pressure, or in a closed vessel, optionally under pressure and/or in an inert atmosphere, for example under an argon or nitrogen atmosphere.

At all stages of the reaction it is possible for any mixtures of isomers which may occur to be separated into the individual isomers, for example diastereoisomers or enantiomers, or into any desired mixtures of isomers, for example racemates or mixtures of diastereoisomers, for example analogously to the methods described under "Additional Process Steps".

In certain cases, for example in the case of hydrogenation, it is possible to obtain stereo-selective reactions, so that, for example, individual isomers can be obtained more easily.

The solvents from which the solvents suitable for any particular reaction can be selected include, for example, water, esters, such as lower alkyl-lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, bis-lower alkane sulfines, such as dimethyl sulfoxide, acid amides, such as N,N-di-lower alkyl-lower alkanoylamides, for example dimethylformamide or dimethylacetamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless indicated to the contrary in the description of the processes. Other solvents specifically mentioned in individual process steps also belong to this list. Such solvents and solvent mixtures can also be used in working-up, for example by chromatography or partitioning.

The compounds, including their salts, may also be obtained in the form of hydrates, or their crystals may include, for example, the solvent used for crystallisation.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable in accordance with the process of the invention is produced under the process conditions and is processed further in situ. In the process of the present invention it is preferable to use those starting materials which result in the compounds described at the beginning as being especially valuable. Reaction conditions analogous to those mentioned in the Examples are especially preferred.

Where necessary, protected starting compounds can be used at any stage of the process and the protecting groups can be removed at suitable stages of the reaction.

STARTING COMPOUNDS

The present invention relates also to novel starting materials and intermediates and to processes for their preparation. The starting materials and the reaction conditions selected are preferably those which result in the compounds described as being preferred.

In the preparation of all starting materials and in the starting materials themselves, free functional groups that are not intended to participate in the reaction concerned or that may interfere with the reaction, may, if necessary, be in protected form, for example they may be protected by the protecting groups mentioned hereinbefore under Process a). Those protecting groups can be freed at suitable times by the reactions described under Process a). The introduction of the protecting groups is effected as described under Process a), especially in accordance with methods described in the standard works mentioned there.

The compounds of formula I used as starting compounds for Process c), especially of formula Ia or Ib, wherein $R_1$ is hydrogen, are obtained, for example, by, in a compound of formula II, especially IIa or IIb,

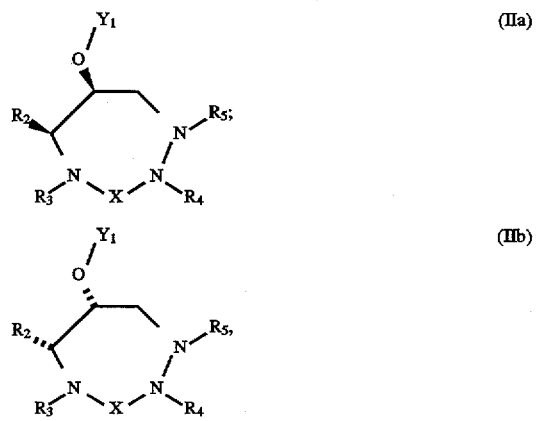

wherein $Y_1$ is a protecting group and also the remaining radicals are as defined, removing the protecting group $Y_1$, especially tri-lower alkylsilyl, such as tert-butyl-dimethylsilyl, under the conditions mentioned in the description of Process a) for the removal of protecting groups.

Compounds of formulae II, IIa and IIb are prepared preferably by reacting a compound of formula VII

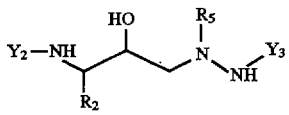

(especially of formula VIIa or VIIb,

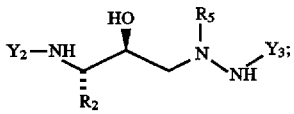

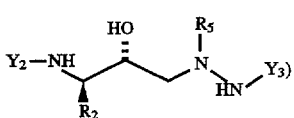

wherein $Y_2$ and $Y_3$ are each independently of the other one of the amino-protecting groups mentioned under Process a), especially tert-lower alkoxycarbonyl, such as tert-butoxcarbonyl, and wherein the remaining radicals are as defined for compounds of formula I, with the introduction of a protecting group $Y_1$ (preferably not of the acyl type, in order to avoid acyl migrations), as described in the standard works mentioned under Process a), for example with a tri-lower alkylsilyl halide, such as a tri-lower alkylsilyl chloride, for example with tert-butyl-dimethyl-chlorosilane, in the presence of a nitrogen base with a hindered, for example tertiary amino group, such as a tri-lower alkylamine, for example ethyldiisopropylamine or triethylamine, or a cyclic tertiary amine, such as dimethylaminopyridine or especially imidazole, in aprotic organic solvents, especially carboxylic acid amides, for example N,N-di-lower alkyl-lower alkanoylamides, such as dimethylformamide or dimethylacetamide, or ethers, especially cyclic ethers, such as dioxane or tetrahydrofuran, or mixtures thereof, at temperatures of from 0° C. to reflux temperature, especially from 10° to 40° C., for example at room temperature, if necessary under a protective gas, such as nitrogen or argon, to yield the corresponding compound of formula VIII

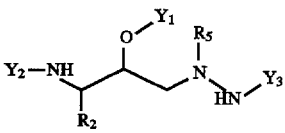

(especially of formula VIIIa or VIIIb,

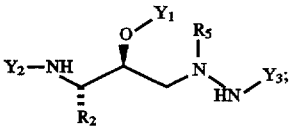

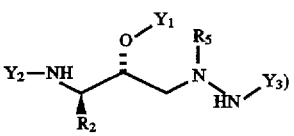

wherein $Y_2$ and $Y_3$ are as defined for compounds of formula VII, $Y_1$ is as defined for compounds of formula II, especially tri-lower alkylsilyl, and the remaining radicals are as defined.

The compounds of formula VIII are then converted, with selective removal of the protecting groups $Y_2$ and $Y_3$ (preferably tert-lower alkoxy caxbonyl), as described under Process a), in known manner, for example with removal under acidic conditions, for example with a lower alkanecarboxylic acid or a halo-lower alkanecarboxylic acid, such as formic acid or trifluoroacetic acid, in the presence or absence of solvents, preferably in polar solvents, such as water, or ethers, preferably cyclic ethers, such as dioxane, or directly dissolved in a liquid organic carboxylic acid, such as formic acid, into compounds of formula IX.

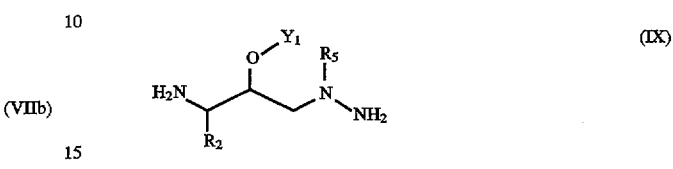

(preferably IXa or IXb,

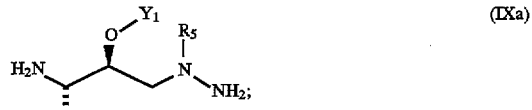

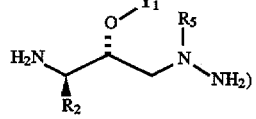

wherein the radicals are as last defined.

The compounds of formula II, or IIa or IIb, can be obtained from the compounds of formula IX, or IXa or IXb, respectively, preferably by two methods.

The first method leads, by way of the reaction of the compound of formula IX (or IXa or IXb) with an acid of formula X

with the exception of free (thio)-carbonic acid itself (X=(C=O) or (C=S)), wherein X is as defined for compounds of formula I (except that it is preferably not —(C=S)—), or with a reactive derivative thereof, to compounds of formula XI

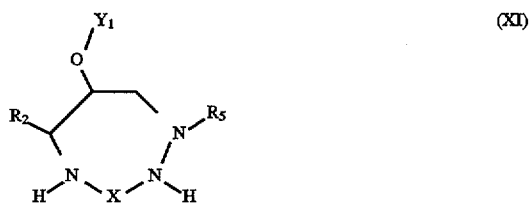

(preferably XIa or XIb,

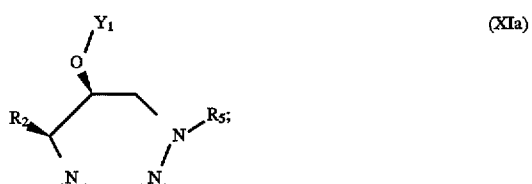

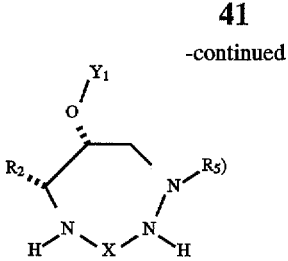
(XIb)

wherein $Y_1$ is a protecting group as defined above and also the remaining radicals are as defined for compounds of formula II. The introduction of the radical —X— can also be carried out in stages by way of the radical —X—OH, or a reactive derivative thereof, which is singly bonded (to only one of the two nitrogen atoms of the compounds of formula IX) and then by again reacting the intermediate to form the compound of formula X. A radical X having the meaning —(C=O)— in compounds of formula XI, especially XIa or XIb, can then be converted into a radical —(C=S)—, as described hereinbefore in the conversions, for example using Lawesons's reagent. Reactive derivatives of compounds of formula X are preferably those of formula Xa, $$Z_1'—X—Z_1'' \quad (Xa)$$

wherein $Z_1'$ and $Z_a''$ are each independently of the other one of the radicals $Z_1$ mentioned for compounds of formula V or Va under Process c) ($Z_1'$ and $Z_1''$ are preferably identical). The compounds of formula Xa can be formed in situ analogously to compounds of formula Va.

The reaction conditions for the acylation are analogous to those described under Process c). Preferably, compounds of formula Xa wherein $Z_1'$ and $Z_1''$ are both the same radical selected from halogen, such as chlorine or bromine, lower alkanoyloxy, such as acetyloxy, or 1-imidazolyl are reacted, the reaction being carried out especially in an inert organic solvent, for example a suitable hydrocarbon, such as a liquid aromatic hydrocarbon, for example toluene or xylene, an ether, for example a cyclic ether, such as tetrahydrofuran or dioxane, or a halogenated, such as chlorinated, hydrocarbon, such as chloroform, methylene chloride or carbon tetrachloride, or mixtures of such solvents, in the absence or presence of an organic nitrogen base, especially a tertiary amine, for example tri-lower alkylamine, such as triethylamine, ethyldiisopropylamine, 4-dimethylaminopyridine or pyridine, at temperatures of from −80° to 30° C., especially from −80° to −50° C. or from 10° to 30° C. (for $Z_1'=Z_1''=$1-imidazolyl), for example at approximately −70° C. or (in the case of imidazolyl $Z_1'$ and $Z_1''$) at approximately room temperature, preferably in the presence of a protective gas, such as argon or nitrogen. Where X is a radical

as defined above, especially with cyano as $R_7$, $Z_1'$ and $Z_1''$ in compounds of formula Xa are preferably lower alkylthio, such as methylthio. The reaction is then carried out preferably in tertiary nitrogen bases, such as a tri-lower alkylamine, for example triethylamine or ethyldiisopropylamine, or a corresponding cyclic nitrogen base, such as pyridine, at temperatures of from 50° C. to reflux temperature, especially at approximately reflux temperature, with the formation of the lower alkylmercaptan corresponding to the radicals $Z_1'/Z_1''$, it also being possible for other solvents to be present.

Compounds of formula II, especially IIa or IIb, are then obtained by reacting compounds of formula XI, especially XIa or XIb, under conditions analogous to those described under Process b) for the reaction of compounds of formula III, especially IIIa or IIIb, with compounds of formula IV wherein the radicals are as defined.

Alternatively, compounds of formula II, especially IIa or IIb, can be obtained first by alkylating a compound of formula IX (especially IXa or IXb), with the introduction of a radical $R_3$ or $R_4$ (using a compound of formula IV, as described above), especially under conditions analogous to those described for the reaction of compounds of formula III with those of formula IV under Process b). The reaction can, however, also be carried out in the absence of bases or in the presence of weaker bases, such as alkali metal alcoholates, for example sodium or potassium methanolate or ethanolate, tertiary nitrogen bases, such as tri-lower alkylamines, for example triethylamine or ethyldiisopropylamine, or 4-dimethylaminopyridine, pyridine or imidazole, under conditions of a first- or second-order nucleophilic substitution, for example in the solvents and at the temperatures as described for Process b). It is also possible to react in succession first one and then the other secondary amino group in compounds of formula IX, especially IXa or IXb, for example for the introduction of different radicals $R_3$ and $R_4$, by reacting them in succession with two different compounds of formula IV, if necessary the amino group that is not to be reacted being protected by one of the amino-protecting groups described under Process a), which is subsequently removed again in accordance with one of the methods mentioned under Process a) for the removal of protecting groups.

It is also possible to use reductive amination for alkylation. For that purpose, a compound of formula IX, especially IXa or IXb, is reductively aminated with an aldehyde or ketone of formula XII $$D=O \quad (XII),$$

wherein D is a radical that is analogous to the unsubstituted or substituted alkyl radicals defined for $R_3$ or $R_4$ in formula I and that carries at the carbon atom bonding the oxygen atom one hydrogen atom fewer than does the corresponding radical $R_3$ or $R_4$ (which can accordingly contain only one bonding carbon atom carrying at least one further hydrogen atom), with hydrogenation in the presence of a catalyst, such as Raney nickel, at normal pressure or at pressures of from 0.1 to 10 MegaPascal (MPa), preferably approximately 10 MPa, or with reduction by means of complex hydrides, such as borohydrides, for example sodium cyanoborohydride. In this case too, gradual reaction of compounds of formula IX (if necessary protected at the second amino nitrogen atom) with compounds of formula XII is possible.

It is also possible to combine the reductive amination and the other type of alkylation described above.

Compounds of formula XIII

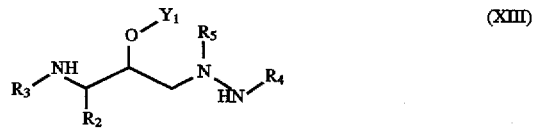
(XIII)

(especially XIIIa or XIIIb,

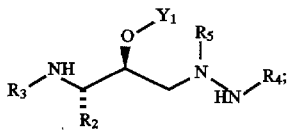

(XIIIa)

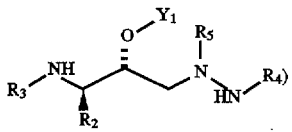

(XIIIb)

are obtained wherein the radicals are as defined for compounds of formula I and $Y_1$ is as defined for compounds of formula IX.

Compounds of formula II, especially IIa or IIb, are obtained from the compounds of formula XIII, especially XIIIa or XIIIb, by reacting the latter with a compound of formula X, especially with a reactive derivative thereof of formula Xa, as described in the reaction of compounds of formula X with those of formula IX.

Finally, it is also possible to introduce first one of the two radicals $R_3$ and $R_4$ at the stage of a compound of formula IX and then the other at the stage of a compound of formula XI.

A person skilled in the art will immediately appreciate that, in the case of the reaction sequences that proceed by way of the compounds of formulae VII, VIII, IX and XI or XIII, the synthesis of preferred compounds labelled "a", on the one hand, and the synthesis of preferred compounds labelled "b", on the other, proceed separately from one another.

Compounds of formula III, especially of formula IIIa or IIIb, are prepared, for example, by removing the hydroxy-protecting group $Y_1$ from compounds of formula XI, especially XIa or XIb, for example by one of the processes mentioned under Process a), to yield compounds of formula XIV

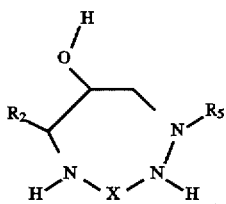

(XIV)

(especially XIVa or XIVb,

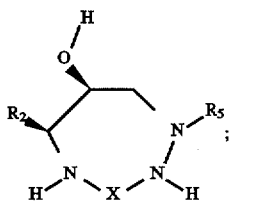 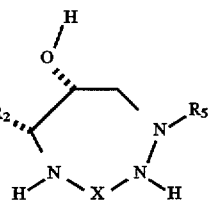

(XIVa) (XIVb))

wherein the radicals are as defined for compounds of formula I, which compounds are then reacted analogously to the conditions mentioned for Process c) with an acid of formula V, or with a reactive derivative thereof, compounds of formula III then being obtained from compounds of formula XIV, in particular compounds of formula IIIa being obtained from those of formula XIVa and compounds of formula IIIb being obtained from those of formula XIVb.

The remaining starting materials and intermediates are known, are commercially available or can be prepared in accordance with processes known per se.

In particular, compounds of formula VII, preferably of formula VIIa or VIIb, can be prepared in accordance with the processes described in European Patent Application EP 0 521 827 (Application number 92810490.0-2103), which was published on 7th Jan. 1993. Under conditions analogous to the reaction conditions mentioned under Process a) of that Application it is possible to react (instead of the compounds shown there of formula

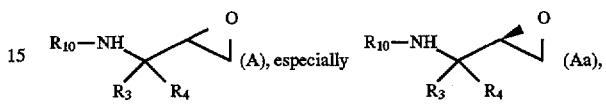

which are reacted under the conditions mentioned there with the compounds of formula

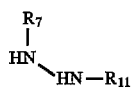

(B) mentioned there, the radicals in the mentioned compounds being as defined in EP 0 521 827) compounds of formula XV

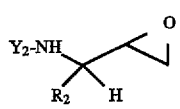

(XV)

(especially XVa or XVb,

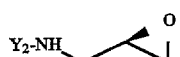 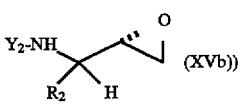

which can be prepared in an analogous manner and wherein the radicals are as defined for compounds of formula V (and which correspond to the compounds of formula A) with compounds of formula XVI

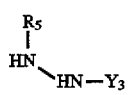

(XVI)

wherein the radicals are as defined for compounds of formula VII (and which correspond to the compounds of formula B), to yield compounds of formula VII (from XV), especially VIIa (from XVa) or VIIb (from XVb). The reaction is carried out preferably at elevated temperature, for example at from 40° C. to reflux temperature, especially at reflux temperature, in a polar organic solvent, especially an alcohol, such as a lower alkanol, for example methanol or ethanol, in the presence or absence of a protective gas, such as nitrogen or argon.

It should be noted that compounds of formula XVb can be obtained by methods analogous to those used for obtaining compounds of formula XVa if (analogously to the multistage reaction in EP 0 521 827, where a compound of formula Aa shown above is obtained from the N-protected amino acids of formula

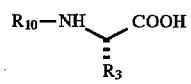
(C)

shown in that Application, wherein the radicals are as defined them) instead of an N-protected amino acid of formula (C) a corresponding N-protected amino acid of formula XVIIb,

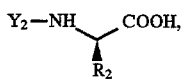
(XVII)

wherein the radicals are as defined above for compounds of formula VII, is reacted to form the epoxide of formula XVb.

PHARMACEUTICAL COMPOSITIONS

The invention relates also to pharmaceutical compositions comprising compounds of formula I or II".

The pharmacologically acceptable compounds of the present invention may be used, for example, in the preparation of pharmaceutical compositions that comprise an effective mount of the active ingredient together or in admixture with a significant amount of inorganic or organic, solid or liquid, pharmaceutically acceptable carriers.

The invention relates also to a pharmaceutical composition suitable for administration to a warm-blooded animal, especially a human being, for the treatment or prevention of a disease responsive to the inhibition of a retroviral protease, especially a retroviral aspartate protease, such as HIV-I- or HIV-II-gag-protease, for example for the treatment or prevention of a retoviral disease, such as AIDS, comprising an amount of a compound of formula I or II", or of a pharmaceutically acceptable salt thereof, that is effective in the inhibition of the retroviral protease, together with at least one pharmaceutically acceptable carrier.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmocokinetic data, the disease to be treated and the mode of administration.

The invention relates also to a method of treating diseases caused by viruses, especially retroviruses, for example AIDS, wherein a therapeutically effective amount of a compound of formula I or II" according to the invention is administered especially to a warm-blooded animal, for example a human being, who on account of one of the mentioned diseases, especially AIDS, requires such treatment. The dose to be administered to warm-blooded animals, for example human beings of approximately 70 kg body weight, is from approximately 3 mg to approximately 3 g, preferably from approximately 10 mg to approximately 1.5 g, for example approximately from 100 mg to 1000 mg per person per day, divided preferably into 1 to 3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are preferably used, it being possible, for example in the case of lyophilised compositions that comprise the active ingredient alone or together with a carrier, for example mannitol, for such solutions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, such as, for example, lauric acid, tridecylic acid, myristic acid, pentadecylic acid, palmitic acid, margaric acid, stearic acid, arachidic acid, behenic acid or corresponding unsaturated acids, such as, for example, oleic acid, elaidic acid, erucic acid, brassidic acid or linoleic acid, where appropriate with the addition of antioxidants, such as, for example, vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for the active ingredients to be incorporated into plastics carriers that allow the active ingredients to diffuse or be released in measured mounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and also soft, sealed capsules made of gelatin and a plasticiser, such as glycerol or sorbitol. The dry-filled capsules may comprise the active ingredient in the form of granules, for example with fillers, such as lactose, binders, such as starches, and/or gildants, such as talc or magnesium stearate, and if desired with stabilisers. In soft capsules the active ingredient is preferably dissolved or suspended in suitable oily excipients, such as fatty oils, paraffin oil or liquid polyethylene glycols, it likewise being possible for stabilisers and/or antibacterial agents to be added. Dyes or pigments may be added to the tablets or dragée coatings or to the capsule casings, for example for identification purposes or to indicate different doses of active ingredient.

The following Examples serve to illustrate the invention but do not limit the scope thereof in any way.

Temperatures are given in degrees Celsius (°C.). Where no temperature is specified, the reaction takes place at room temperature. The $R_f$ values, which indicate the ratio of the seepage propagation of the substance in question to the seepage propagation of the eluant front, are determined on thin-layer silica gel plates by thin-layer chromatography (TLC) in the following solvent systems:

TLC eluant systems:

| A | chloroform/methanol | 95:5 |
| B | toluene/ethyl acetate | 2:1 |
| C | methylene chloride/diethyl ether | 5:1 |
| D | hexane/ethyl acetate | 4:1 |
| E | chloroform/methanol/water/acetic acid | 85:13:1.5:0.5 |
| F | hexane/ethyl acetate | 5:1 |
| G | hexane/ethyl acetate | 1:1 |
| H | methylene chloride/diethyl ether | 20:1 |
| I | hexane/ethyl acetate | 2:1 |
| J | hexane/ethyl acetate | 3:1 |
| K | toluene/ethyl acetate | 4:1 |
| L | methylene chloride/diethyl ether/hexane | 1:1:3 |
| M | chloroform/methanol | 5:1 |
| N | methylene chloride/diethyl ether | 20:1 |
| O | methylene chloride/diethyl ether | 10:1 |
| P | methylene chloride/diethyl ether | 100:1 |
| Q | hexane/ethyl acetate | 3:2 |
| R | hexane/ethyl acetate | 10:1 |
| S | ethyl acetate/ethanol | 10:1 |
| T | hexane/ethyl acetate | 8:1 |

The abbreviation "$R_f(A)$" indicates, for example, that the $R_f$ value was determined in solvent system A. The quantitative ratio of solvents to one another is always indicated in parts by volume.

HPLC gradients:

| I | 20% → 100% a) in b) for 35 min. |
| II | 20% → 100% a) in b) for 20 min. |

Eluant a): acetonitrile+0.05% TFA; eluant b): water+ 0.05% TFA. Column (250×4.6 mm) filed with "reversed-phase" material $C_{18}$-Nucleosil® (5 μm mean particle size, silica gel covalently derivatised with octadecylsilanes, Macherey & Nagel, Düren, Federal Republic of Germany). Detection by UV absorption at 215 nm. The retention times ($t_{Ret}$) are given in minutes. Flow rate 1 ml/min.

The same abbreviations are used in flash chromatography and medium pressure chromatography to indicate the eluant systems.

The other shortened names and abbreviations used have the following meanings:

| abs. | absolute (indicates solvent is anhydrous) |
| atm | physical atmospheres (unit of pressure) - 1 atm corresponds to 1.013 bar |
| Boc | tert-butoxycarbonyl |
| DIPE | diisopropyl ether |
| DMAP | 4-dimethylaminopyridine |
| DMF | dimethylformamide |
| DMSO | dimethyl sulfoxide |
| ether | diethyl ether |
| sat. | saturated |
| h | hour(s) |
| HV | high vacuum |
| min | minute(s) |
| MS | mass spectroscopy |
| Ref. Ex. | Reference Example |
| RT | room temperature |
| RE | rotary evaporator |
| brine | saturated sodium chloride solution |
| TBAF | tetrabutylammonium fluoride trihydrate |
| TBF | tetrahydrofuran |

Mass spectroscopic data are obtained either by conventional MS or in accordance with the "Fast Atom Bombardment" (FAB-MS) method. The mass data relate in the first instance to the unprotonated molecule ion $(M)^+$ or, in the second case, the protonated molecule ion $(M+H)^+$.

The values for proton nuclear resonance spectroscopy ($^1$H-NMR) are indicated in ppm (parts per million) based on tetramethylsilane as the internal standard. s=singlet, d=doublet, t=triplet, q=quartet, m=multiplet, dd=double doublet, br=broad.

The values for IR spectra are indicated in $cm^{-1}$, and the respective solvent is in round brackets. If indicated, s denotes a strong, m denotes a moderate and w denotes a weak intensity of the band concerned.

The residue with the abbreviation -[Phe$^{NN}$Phe] denotes the bivalent residue of (S)-amino-4-phenyl-1-(N-benzylhydrazino)-butan-2(S)-ol and has the formula

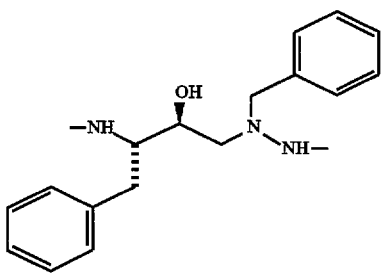

The residue with the abbreviation -[Phe$^{NN}$Cha] denotes the bivalent residue of 3(S)-amino-4-phenyl-1-(N-cyclohexylmethylhydrazino)-butan-2(S)-ol and has the formula The residue with the abbreviation -[Phe$^{NN}$Leu] denotes the bivalent residue of 3(S)-amino-4-phenyl-1-(N-isobutylhydrazino)-butan-2(S)-ol and has the formula

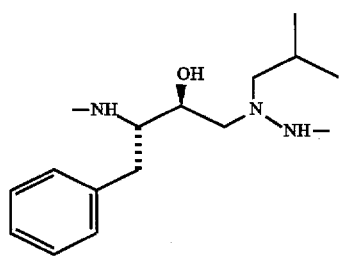

The residue with the abbreviation -[Phe$^{NN}$Nle] denotes the residue of 3(S)-amino-4-phenyl-1-(N-n-butylhydrazino)-butan-2(S)-ol and has the formula

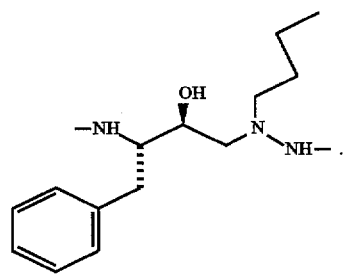

The residue with the abbreviation -[Phe$^{NN}$(p-F)Phe] denotes the bivalent residue of 3(S)-amino-4-phenyl-1-(N-(p-fluorophenylmethyl)-hydrazino)-butan-2(S)-ol and has the formula

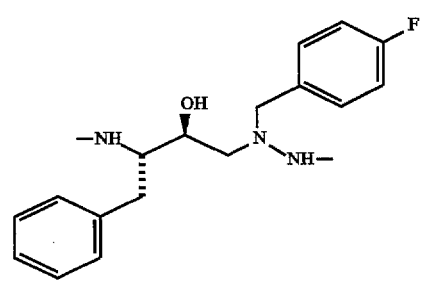

The residue with the abbreviation -[(p-F)Phe$^{NN}$(p-F)Phe] denotes the bivalent residue of (S)-amino-4-(p-fluorophenyl)-1-(N-(p-fluorophenylmethyl)-hydrazino)-butan-2(S)-ol and has the formula

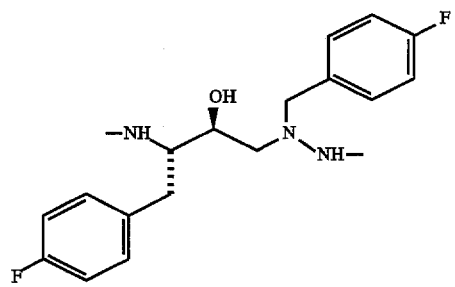

The residue with the abbreviation -[Phe$^{NN}$(p-CN)Phe] denotes the bivalent residue of 3(S)-amino-4-phenyl-1-(N-(p-cyanophenylmethyl)-hydrazino)-butan-2(S)-ol and has the formula

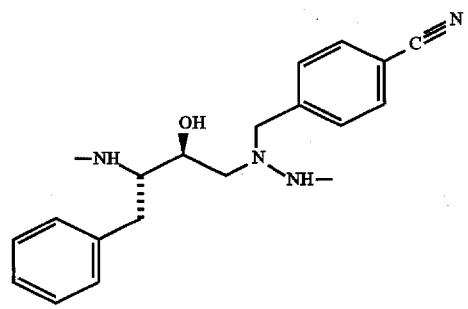

The residue with the abbreviation -[Cha$^{NN}$Leu] denotes the bivalent residue of 3(S)-amino-4-cyclohexyl-1-(N-isobutyl-hydrazino)-butan-2(S)-ol and has the formula

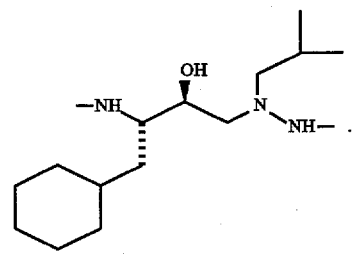

The bivalent residue of 1-[2(S)-acetoxy-3(S)-amino-4-phenylbutyl]-[1-cyclohexylmethyl]-hydrazine has the formula

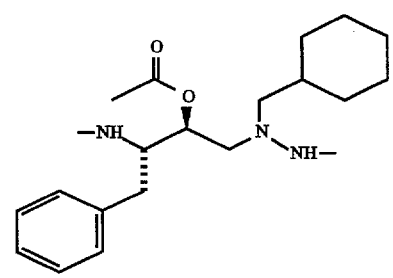

The abbreviations customarily employed in peptide chemistry are used to denote bivalent residues of natural α-amino acids. However, amino acids located in the compound names on the fight of the residues -[Phe$^{NN}$Phe], -[Phe$^{NN}$Cha], -[Phe$^{NN}$Leu], -[Phe$^{NN}$Nle], -[Phe$^{NN}$(p-F)Phe], -[(p-F)Phe$^{NN}$(p-F)Phe], -[Phe$^{NN}$(p-CN)Phe] and -[Cha$^{NN}$Leu], unlike customary peptide nomenclature where the amino terminus is on the left and the carboxy terminus is on the right, have the bonding carboxy group on the left, which is shown by an arrow (←) symbolising the reversal of the direction of bonding (inversion). If known, the configuration at the α-carbon atom is indicated by prefixing (L) or (D). Tyrosine residues etherified by the radical R at the phenolic hydroxy group have the abbreviation Tyr(OR). Nle indicates the residue of norleucine.

REFERENCE EXAMPLE 1

Boc-[Phe$^{NN}$Phe]-Boc

A solution of 300 mg (1.14 mmol) of (2R)-[1'(S)-Boc-amino-2'-phenylethyl]oxirane (J. Org. Chem. 50, 4615 (1985)) and 253 mg (1.14 mmol) of tert-butyl-3-benzyl-carbazate (J. Chem. Soc., Perkin I, 1712 (1975)) in 4 ml of methanol is heated under reflux for 12 h. When the reaction mixture has cooled to 0° C., a large proportion of the title compound is precipitated. The mother liquor is concentrated by evaporation and the residue is dissolved in a small amount of methylene chloride. After the dropwise addition of hexane, more title compound is obtained in the form of a white precipitate. FAB-MS: (M+H)$^+$=486, $t_{Ref}$(I)=26.8 min, TLC R$_f$(A)=0.70.

REFERENCE EXAMPLE 2

Boc-[Phe$^{NN}$Cha]-Boc

Analogously to Ref. Ex. 1, the title compound is obtained in the form of a white precipitate from hexane starting from 231 mg (0.88 mmol) of (2R,3S)-1-[3-Boc-amino-2-phenylethyl]oxirane and 200 mg (0.88 mmol) of tert-butyl-3-cyclohexylmethyl-carbazate. FAB-MS: (M+H)$^+$=492, $t_{Ref}$ (I)=30.4 min, TLC R$_f$(A)=0.78.

The starting material is prepared as follows:
a) tert-butyl-3-cyclohexylmethyl-carbazate:

10.2 g (45.1 mmol) of cyclohexylcarbaldehyde-tert-butoxycarbonylhydrazone dissolved in 400 ml of methanol are hydrogenated in the presence of 5.1 g of 5% platinum-on-carbon at RT and 4 atm hydrogen pressure. When the reaction is complete, the catalyst is removed by filtration and the filtrate is concentrated by evaporation. The residue is dissolved in methylene chloride and washed with water. The organic phase is concentrated by evaporation to yield the title compound in the form of a colourless resin. $^1$H-NMR (200 MHz, CDCl$_3$): 6.1 (s, br, 1H), 3.9 (s, br, 1H), 2.65 (d, 2H), 1.8–0.75 (m, 11H), 1.45 (s, 9H), $t_{Ref}$(I)=32.0 min, TLC R$_f$(A)=0.75.

b) cyclohexylcarbaldehyde-tert-butoxycarbonylhydrazone:

A solution of 10.8 g (81.2 mmol) of tert-butylcarbazate and 10.1 g (90 mmol) of cyclohexylcarbaldehyde in 400 ml of ethanol is heated under reflux for 2 h. Half of the solvent is then distilled off and the title compound is precipitated by the addition of water. It is used further directly in a).

REFERENCE EXAMPLE 3

Boc-[Phe$^{NN}$Leu]-Boc

Analogously to Ref. Ex. 1, the title compound is obtained in the form of a precipitate from hexane starting from 1.0 g (3.8 mmol) of (2R)-[1'(S)-Boc-amino-2'-phenylethyl]oxirane and 715 mg (3.8 mmol) of tert-butyl-3-isobutyl-carbazate (preparation: J. Chem. Soc., Perkin I, 1712 (1975)). FAB-MS: (M+H)$^+$=452, $t_{Ref}$(I)=27.2 min, TLC R$_f$(B)=0.55.

REFERENCE EXAMPLE 4

N-Trifluoroacetyl-[Phe$^{NN}$(p-F)Phe]-Boc

A solution of 4.0 g (15.4 mmol) of 2(R)-[1'(S)-(trifluoroacetyl-amino)-2'-phenylethyl]-oxirane and 3.89 g (16.2 mmol)of tert-butyl-3-(p-fluorophenyl-methyl)-carbazate in 35 ml of methanol is heated in a bomb tube for approximately 20 h at 80° C. The reaction mixture is concentrated by evaporation, the residue is dissolved in a small amount of dichloromethane and the tide compound is precipitated therefrom using hexane (refrigerator). Further product is obtained by column chromatography (SiO$_2$, methylene chloride/ether 95:7). TLC R$_f$(C)=0.57; $t_{Ref}$(I)=24.3 min; FAB-MS (M+H)$^+$=500.

The starting materials are prepared as follows:
a) N-3(S)-(Boc-amino)-2(R,S)-hydroxy-4-phenyl-1-trimethylsily-butane Under a N$_2$ atmosphere, 24.7 g (1.02 mol) of magnesium are placed in 100 ml of abs. ether and, over a period of 35 min, a small amount of iodine and at the same time 132.5 ml (0.95 mol) of chloromethyltrimethylsilane and 300 ml of ether are added, the temperature being maintained at 38° C. by means of an ice bath. The resulting reaction mixture is then stirred for 1.5 h at RT. After cooling to −60° C., a suspension of 48.6 g (0.195 mol) of N-Boc-phenylalaninal (preparation: D. J. Kempf, J. Org. Chem. 51, 3921 (1986)) in 1.1 liter of ether is added over a period of 40 min. The reaction mixture is heated to RT over a period of 90 min and stirred for a further 90 min at that temperature. It is then poured into 2 liters of ice-water and 1.5 liters of 10% aqueous citric acid. The separated aqueous phase is extracted twice with 500 ml of ether. All of the ether extracts are washed with 500 ml of 10% citric acid and twice with brine. After drying over sodium sulfate, concentration is carried out in vacuo and the resulting title compound is used further without additional purification. TLC R$_f$(D)=0.6; FAB-MS (M+H)$^+$=338.

b) 1-phenyl-3-butene-2(S)-amine:

35.6 ml (0.28 mol) of an approximately 48% solution of boron trifluoride in ether are added over a period of 10 min at 5° C. to a solution of 18.8 g (0.055 mol) of 3(S)-(Boc-amino-2-(R,S)-hydroxy-4-phenyl-1-trimethylsilyl-butane in 420 ml of methylene chloride. The reaction mixture is then stirred for 16 h at RT, cooled to 10° C., and 276 ml of a 4N sodium hydroxide solution are added over a period of 20 min. The aqueous phase is separated off and extracted twice with 400 ml of methylene chloride each time. The combined organic extracts are washed with brine and dried over sodium sulfate. The title product is used further without additional purification. TLC R$_f$(E)=0.15; IR (methylene chloride) (cm$^{-1}$): 3370, 3020, 2920, 1640, 1605.

c) N-trifluoroacetyl-1-phenyl-3-butene-2(S)-amine:

At 0° C., 17.0 ml (121 mmol) of trifluoroacetic anhydride are added dropwise to 11.9 g (81 mmol) of 1-phenyl-3-butene-2(S)-amine dissolved in 210 ml of methylene chloride and 70 ml of pyridine. After stirring for 0.5 h at 0° C. the batch is extracted twice with dilute HCl, with water and with brine. The aqueous phases are washed twice with methylene chloride, dried with sodium sulfate and concentrated by evaporation: TLC-R$_f$(F)=0.4.

d) 2(R)-[1'(S)-(trifluoroacetyl-amino)-2'-phenylethyl]-oxirane:

54.28 g (314 mmol) of m-chloroperbenzoic acid are added to a solution of 14.5 g (60 mmol) of N-trifluoroacetyl-1-phenyl-3-butene-2(S)-amine in 600 ml of chloroform and the reaction mixture is stirred for 24 h at RT to complete the reaction. It is then washed twice with 10% sodium sulfite solution, twice with sat. sodium carbonate solution, with water and with brine. The aqueous phases are extracted twice with methylene chloride and the combined organic phases are dried with sodium sulfate and concentrated by evaporation to yield the title compound which is used in the next stage without further purification: TLC $R_f(I)$=0.41.

e) p-fluorophenylcarbaldehyde-tert-butoxycarbonylhydrazone:

32 g (242 mmol) of tert-butylcarbazate and 30 g (242 mmol) of p-fluorobenzaldehyde in 300 ml of ethanol are reacted for 3 h at 80° C. to form the title compound which crystallises out upon cooling and diluting with water: TLC $R_f(G)$=0.48; $t_{Ret}(I)$=19.4 min.

f) tert-butyl-3-(p-fluorophenyl-methyl)-carbazate:

55 g (231 mmol) of p-fluorophenylcarbaldehyde-tert-butoxycarbonylhydrazone in 500 ml of THF are hydrogenated at RT with 5.5 g of 5% palladium-on-carbon to form the title compound. When the reaction is complete, the catalyst is removed by filtration and the filtrate is concentrated by evaporation. The residue is dissolved in methylene chloride and washed with water. The organic phase is concentrated by evaporation to yield the title compound: $^1$H-NMR (200 MHz, CD$_3$OD): 7.35 (dd, 8 and 6 Hz, 2H), 7.05 (t, 8 Hz, 2H), 3.9 (s, 2H), 1.45 (s, 9H).

REFERENCE EXAMPLE 5

H-[Phe$^{NN}$(p-F)Phe]-Boc

At 70° C. and under a N$_2$ atmosphere, 15 ml of a 1M aqueous solution of potassium carbonate are added dropwise to a solution of 0.3 g (0.6 mmol) of N-trifluoroacetyl-[Phe$^{NN}$(p-F)Phe]-Boc (for preparation see Ref. Ex. 4) in 50 ml of methanol and then the reaction mixture is stirred for 25 h at that temperature. It is then concentrated by evaporation under HV, methylene chloride is added to the residue and the batch is washed twice with water and brine. The aqueous phases are extracted twice with methylene chloride and the organic phases are dried with sodium sulfate and concentrated by evaporation. The crude product is used in the next stage without further purification: $t_{Ret}(I)$=16.2 min.

REFERENCE EXAMPLE 6

N-Trifluoroacetyl-[Phe$^{NN}$(p-F)Phe]-H

At 0° C., 5 ml of trifluoroacetic acid are added to 0.20 g (0.40 mmol) of N-trifluoroacetyl-[Phe$^{NN}$(p-F)Phe]-Boc (for preparation see Ref. Ex. 4) in 5 ml of methylene chloride. After stirring for 4 h at 0° C. and for 2 h at RT, the reaction mixture is concentrated by evaporation. Lyophilisation of the residue from dioxane yields the title compound which is reacted further without purification: $t_{Ret}(I)$=14.7 min.

REFERENCE EXAMPLE 7

N-Trifluoroacetyl-[Phe$^{NN}$Phe]-Boc

Analogously to Ref. Ex. 4, 1.82 g (7.0 mmol) of 2(R)-[1'(S)-(trifluoroacetyl-amino)-2'-phenylethyl]-oxirane (Ref. Ex. 4 d)) and 1.58 g (7.1 mmol) of tert-butyl-3-benzyl-carbazate (J. Chem., Perkin I, 1712 (1975)) in 15 ml of methanol are reacted in a bomb tube to form the title compound which is isolated by column chromatography (SiO$_2$, methylene chloride/ether 50:1): TLC $R_f(C)$=0.38; $t_{Ret}(I)$=24.5 min.

REFERENCE EXAMPLE 8

H-[Phe$^{NN}$Phe]-Boc

Analogously to Ref. Ex. 5, 258 mg (0.53 mmol) of N-trifluoroacetyl-[Phe$^{NN}$Phe]-Boc in 60 ml of methanol are reacted with 10.7 ml of 1M potassium carbonate solution to form the title compound.

$^1$ H-NMR (CD$_3$OD, 200 MHz): 7.4–7.1 (m,10H), 3.87 (m,2H), 3.57 (dxt, 1H), 3.0–2.5 (m,5H), 1.29 (s,9H).

REFERENCE EXAMPLE 9

N-Trifluoroacetyl-[(p-F)Phe$^{NN}$(p-F)Phe]-Boc

Analogously to Ref. Ex. 4, 415 mg (1.49 mmol) of 2(R)-[1'(S)-(trifluoroacetyl-amino)-2'-(p-fluorophenyl)ethyl]-oxirane and 377 mg (1.57 mmol) of tert-butyl-3-(p-fluorophenyl-methyl)-carbazate in 9 ml of methanol are reacted to form the title compound: TLC $R_f(N)$=0.53; FAB-MS (M+H)$^+$=518; $^1$H-NMR (300 MHz, CD$_3$OD): 7.4–7.3 and 7.3–7.2 (2m, each 2H), 7.05–6.9 (m, 4H), 4.23 (m, 1H), 3.90–3.65 (m, 3H), 3.03–2.78 and 2.74–2.60 (2m, each 2H), 1.30 (s, 9H).

The starting material is prepared as follows:

a) N-Boc-(p-fluorophenylalanine):

In 0.4 liter of dioxane/water 1:1, 20 g (109 mmol) of p-fluorophenylalanine (Fluka, Buchs, Switzerland) are reacted with 35.5 g (163 mmol) of Boc-anhydride and 150 g (1.09 mol) of potassium carbonate. After 4 h, the reaction mixture is acidified with citric acid solution and extracted with 3 portions of ethyl acetate. The organic phases are washed with 10% citric acid, water and brine, dried with sodium sulfate and concentrated by evaporation. The residue is dissolved in a small amount of methylene chloride and crystallised by the addition of hexane to yield the tide compound: $t_{Ret}(I)$=16.9 min.

b) N-Boc-(p-fluorophenylalaninol):

At from −5° C. to −10° C., 9.66 ml (69 mmol) of triethylamine are added to a solution of 17.9 g (63 mmol) of N-Boc-(p-fluorophenylalanine) in 73 ml of abs. THF, and a solution of 9.05 ml (69 mmol) of chloroformic acid isobutyl ester in 44 ml of abs. THF is added dropwise. After stirring for 0.5 h at RT, the precipitate formed is filtered off with suction. The filtrate is added dropwise with cooling to 4.77 g (126 mmol) of sodium borohydride in 28 ml of water. After stirring for 4 h at RT, the batch is acidified with 10% citric acid, some of the THF is evaporated off using a RE and the residue is partitioned between 3 portions of ethyl acetate, 2 portions of 2N sodium hydroxide solution, water, sat. sodium hydrogen carbonate solution and brine. The organic phases are dried with sodium sulfate and concentrated by evaporation and the residue is dissolved in a small amount of methylene chloride and crystallised by the addition of hexane to yield the title compound: TLC $R_f(G)$=0.36; $t_{Ret}(I)$=16.8 min; $^1$H-NMR (200 MHz, CD$_3$OD): 7.24 (dd, 8 and 5 Hz, 2H), 6.98 (t, 8 Hz, 2H), 3.73 (m, 1H), 3.47 (d, 5 Hz, 2H), 2.88 (dd, 13 and 6 Hz, 1H), 2.62 (dd, 13 and 8 Hz, 1H), 1.36 (s, 9H).

c) N-Boc-(p-fluorophenylalaninal):

Under a N$_2$ atmosphere, 4.44 ml (62.4 mmol) of DMSO dissolved in 76 ml of methylene chloride are added dropwise to a solution, cooled to −60° C., of 4.0 ml (46.8 mmol) of oxalyl chloride in 44 ml of methylene chloride. After stirring for 15 min, 8.4 g (31.2 mmol) of N-Boc-(p-fluorophenylalaninol) in the form of a solution in 185 ml of methylene chloride/THF 1:1 are added to the clear reaction solution (→precipitation) and the batch is stirred for 25 min. 17.3 ml (124.8 mmol) of triethylamine dissolved in 38 ml of methylene chloride are then added. After stirring for 30 min, 278 ml of a 20% potassium hydrogen sulfate solution are added dropwise followed by 220 ml of hexane. The batch is allowed to warm to RT and the aqueous phase is separated off and extracted with 2 portions of ether. The organic phases are washed with sat. sodium hydrogen carbonate solution, water and brine, dried with sodium sulfate and concentrated by evaporation to yield the title compound which is used in the next stage without further purification: $^1$H-NMR (200 MHz, CDCl$_3$): 9.63 (s, 1H), 6.9–7.2 (2m, 4H), 5.04 (m, 1H), 4.42 (m, 1H), 3.10 (m, 2H), 1.43 (s, 9H).

d) N-3(S)-(Boc-amino)-2(R,S)-hydroxy-4-(p-fluorophenyl)-1-trimethylsilyl-butane:

Analogously to Ref. Ex. 4 a), 1.63 g (67 mmol) of magnesium in 33 ml of abs. ether are reacted with 8.3 ml (60 mmol) of chloromethyltrimethylsilane to form the Grignard compound which, after reaction with 13 mmol of N-Boc-(p-fluorophenylalaninal), extraction and column chromatography (SiO$_2$, hexane/ethyl acetate 5:1→4:1) yields a diastereoisomeric mixture of the title compound: TLC R$_f$(D)= 0.32; t$_{Ret}$(I)=24.9 min (22%)/25.5 min (78%); FAB-MS (M+H)$^+$=356.

e) 1-(p-fluorophenyl)-3-butene-2(S)-amine:

Analogously to Ref. Ex. 4 b), 1.1 g (3.1 mmol) of N-3(S)-(Boc-amino)-2(R,S)-hydroxy-4-(p-fluorophenyl)-1-trimethylsilyl-butane in 22 ml of methylene chloride are reacted with 1.9 ml (15.5 mmol) of an approximately 48% solution of boron trifluoride in ether to form the title compound: $^1$H-NMR (300 MHz, CDCl$_3$): 7.2–7.10 and 7.05–6.9 (2m, each 2H), 5.9–5.8 (m, 1H), 5.2–5.0 (m, 2H), 3.57 (m, 1H), 2.79 (dd, 12 and 6 Hz, 1H), 2.62 (dd, 12 and 8 Hz, 1H), 1.7 (sb, 2H).

f) N-trifluoroacetyl-1-(p-fluorophenyl)-3-butene-2(S)-amine:

Analogously to Ref. Ex. 4 c), 364 mg (2.2 mmol) of 1-(p-fluorophenyl)-3-butene-2(S)-amine in 1.8 ml of methylene chloride and 5.4 ml of pyridine are reacted with 460 μl (3.3 mmol) of trifluoroacetic anhydride to form the title compound which is obtained in pure form after digestion with hexane: TLC R$_f$(I)=0.58; MS (M)$^+$=261.

g) 2(R)-[1'(S)-(trifluoroacetyl-amino)-2'-(p-fluorophenyl)ethyl]-oxirane:

Analogously to Ref. Ex. 4 d), 359 mg (1.37 mmol) of N-trifluoroacetyl-1-(p-fluorophenyl)-3-butene-2(S)-amine in 9 ml of chloroform are oxidised with 1.18 g (6.87 mmol) of m-chloroperbenzoic acid to form the title compound: TLC R$_f$(J)=0.45.

REFERENCE EXAMPLE 10

H-[(p-F)Phe$^{NN}$(p-F)Phe]-Boc

Analogously to Ref. Ex. 5), 285 mg (0.55 mmol) of N-trifluoroacetyl-[(p-F)Phe$^{NN}$(p-F)Phe]-Boc in 45 ml of methanol are reacted with 14 ml of 1M potassium carbonate solution to form the rifle compound: t$_{Ret}$(I)=16.4 min.

REFERENCE EXAMPLE 11

Boc-[Phe$^{NN}$(p-F)Phe]-Boc

Analogously to Ref. Ex. 1, the title compound is obtained from 2.0 g (7.60 mmol) of (2R)-[1'(S)-Boc-amino-2'-phenylethyl]oxirane and 2.17 g (9.04 mmol) of tert-butyl-3-(4-fluorophenyl-methyl)-carbazate from Ref. Ex. 4 f) after chromatographic purification on silica gel using hexane/ethyl acetate (2:1). FAB-MS: (M+H)$^+$=504, t$_{Ret}$(I)=26.2 min, TLC R$_f$(I)=0.26.

REFERENCE EXAMPLE 12

Boc-[Phe$^{NN}$(p-CN)Phe]-Boc

Analogously to Ref. Ex. 1, the title compound is obtained from 2.0 g (7.60 mmol) of (2R)-[1'(S)-Boc-amino-2'-phenylethyl]oxirane and 1.87 g (7.6 mmol) of tert-butyl-3-(4-cyanophenyl-methyl)-carbazate after cristallisation from methanol/DIPE. FAB-MS: (M+H)$^+$=511, t$_{Ret}$(I)=25 min, TLC R$_f$(K)-0.19.

The starting material is prepared as follows:

a) tert-butyl-3-(4-cyanophenyl-methyl)-carbazate:

Analogously to Ref. Ex. 2 b), 10 g (76.3 mmol) of 4-cyanobenzaldehyde and 10 g (76.3 mmol) of tert-butylcarbazate in ethanol are reacted to form 4-cyanophenylcarbaldehyde-tert-butoxycarbonylhydrazone. 11.1 g thereof are hydrogenated in 150 ml of THF in the presence of 2 g of 10% palladium-on-carbon at 2 atm hydrogen pressure and yield the title compound: $^1$H-NMR (200 MHz, CDCl$_3$): 7.65 (d, J=8 Hz, 2H), 7.45 (d, J=8 Hz, 2H), 6.08 (s, br, 1H), 4.3 (s, br, 1H), 4.02 (s, 2H), 1.45 (s, 9H).

REFERENCE EXAMPLE 13

Boc-[Cha$^{NN}$Leu]-Boc

A solution of 200 mg (0.24 mmol) of Boc-[Phe$^{NN}$Leu]-Boc (Ref. Ex. 3) in 15 ml of methanol is hydrogenated for 4 h in the presence of 10 mg of Nishimura catalyst (Rh(III) and Pt(IV) oxide monohydrate, Degussa) at 1 atm hydrogen pressure. The catalyst is removed by filtration and the solvent is completely evaporated off to yield the title compound, after crystallisation from methylene chloride/hexane. t$_{Ret}$(I)=26.7 min, TLC R$_f$(L)=0.21.

REFERENCE EXAMPLE 14

H-[Phe$^{NN}$Leu]-Boc

Analogously to Ref. Ex. 5, the title compound is obtained from 1.27 g (2.84 mmol) of N-trifluoroacetyl-[Phe$^{NN}$Leu]-Boc (Ref. Ex. 15) and 24 ml of 1N aqueous sodium carbonate solution in 90 ml of methanol after precipitation from methylene chloride by the addition of DIPE: t$_{Ret}$(I)= 14.9 min, TLC R$_f$(M)=0.38.

REFERENCE EXAMPLE 15

N-Trifluoroacetyl-[Phe$^{NN}$Leu]-Boc

Analogously to Ref. Ex. 4, the title compound is obtained from 3 g (11.57 mmol) of 2(R)-[1'(S)-(trifluoroacetyl-amino)-2'-phenylethyl]-oxirane from Ref. Ex. 4 d) and 2.3 g (12.15 mmol) of tert-butyl-3-isobutyl-carbazate (preparation: J. Chem. Soc. Perkin I, 1712 (1975)) after chromatographic purification on silica gel using methylene chloride/ether (20:1). t$_{Ret}$(I)=24.7 min, TLC R$_f$(N)=0.36.

REFERENCE EXAMPLE 16

N-Trifluoroacetyl-[Phe$^{NN}$Leu]-H.2 HCl

By reacting 300 mg (0.67 mmol) of N-trifluoroacetyl-[Phe$^{NN}$Leu]-Boc from Ref. Ex. 15 with 4N hydrogen chloride in dioxane for 2 h at RT under a nitrogen atmosphere with stirring and subsequently lyophilising, and then by lyophilising again from dioxane/tert-butanol, the title compound is obtained in the form of a flocculent solid. R$_f$(N) <0.1.

REFERENCE EXAMPLE 17

H-[Phe$^{NN}$Nle]-Boc

Analogously to Ref. Ex. 5, the title compound is obtained from 830 mg (1.85 mmol) of N-trifluoroacetyl-[Phe$^{NN}$Nle]

-Boc (Ref. Ex. 18) after precipitation from methylene chloride/DIPE. $t_{Ref}(I)=15.4$ min, TLC $R_f(M)=0.54$.

REFERENCE EXAMPLE 18

N-Trifluoroacetyl-[Phe$^{NN}$Nle]-Boc

Analogously to Ref. Ex. 4, the title compound is obtained from 1 g (3.86 mmol) of 2(R)-[1'-(S)-(trifluoroacetylamino)-2'-phenylethyl]-oxirane from Ref. Ex. 4 d) and 720 mg (3.86 mmol) of tert-butyl-3-butyl-carbazate after chromatographic purification on silica gel with methylene chloride/ether (20:1). $t_{Ref}(I)=25.3$ min, TLC $R_f(O)=0.43$.

The starting material is prepared as follows:
a) tert-butyl-3-butyl-carbazate:

Analogously to Ref. Ex. 2 b), there is obtained from 18.0 g (136.2 mmol) of tert-butyl-carbazate and 12.3 ml (136.2 mmol) of n-butanal the corresponding tert-butoxycarbonylhydrazone (25 g, 99%) in the form of a crude product which is hydrogenated as described in Ref. Ex. 2a) in the presence of 10 g of 5% platinum-on-carbon and 4 atm hydrogen pressure. Chromatographic purification of the crude product on silica gel using hexane/ethyl acetate (1:1) yields the title compound. TLC $R_f(G)=0.44$, $^1$H-NMR (200 MHz, CD$_3$OD). 0.92 (t, J=7 Hz, 3H), 1.43 (s, 9H), 1.30 to 1.50 (m, 4H), 2.75 (t, J=7 Hz, 2H).

The above-mentioned title compounds of the Reference Examples serve as starting materials for the following Examples:

EXAMPLE 1

(5(S),6(S))-5-benzyl-2,4-bis(4-fluorophenylmethyl)-1-cyclohexylmethyl-6-hydroxy-1,2,4-triazepan-3-one 28.5 mg (0.090 mmol) of TBAF are added to a solution of 29.3 mg (0.045 mmol) of (5(S),6(S ))-5-benzyl-2,4-bis (4-fluorophenylmethyl)-6-(tert-butyldimethylsilyloxy)-1-cyclohexylmethyl-1,2,4-triazepan-3-one in 1 ml of DMF. After 18 h at RT the batch is poured into 50 ml of water and extracted with 3 portions of ethyl acetate. The organic phases are washed in succession with 2 portions of sat. sodium hydrogen carbonate solution, water and brine, dried with Na$_2$SO$_4$ and concentrated by evaporation. Digestion from hexane in an ultrasound bath yields the pure title compound: $[\alpha]^D=-52°$ (c=1; ethanol); $t_{Ref}(II)=20.2$ min; FAB-MS (M+H)$^+$=534.

The starting material is prepared as follows:
a) 3(S)-(Boc-amino)-4-phenyl-1-(2-Boc-1-cyclohexylmethylhydrazino)-2(S)-((tert-butoxydimethylsilyl)oxy)-butane:

8.29 g (121 mmol) of imidazole and 9.2 g (60.9 mmol) of tert-butyl-dimethyl-chlorosilane are added to a solution of 20 g (40.6 mmol) of 3(S)-(Boc-amino)-4-phenyl-1-(2-Boc-1-cyclohexylmethylhydrazine)-butan-2(S)-ol (Boc-[Phe$^{NN}$Cha]-Boc=Ref. Ex. 2) in 44 ml of dioxane and 6 ml of DMF. Because after 16 h at RT, HPLC indicates that the reaction mixture still contains educt, a total of 8.29 g of imidazole and 9.2 g of tert-butyldimethylchlorosilane is added again in portions and the batch is finally stirred for 50 h. The white suspension is poured into ice-water and extracted with 3 portions of ethyl acetate. The organic phases are washed in succession twice with water and then with brine, dried with Na$_2$SO$_4$ and concentrated by evaporation. Column chromatography (SiO$_2$, methylene chloride/ether 100:1) yields the pure title compound: TLC $R_f(P)=0.41$; $t_{ref}(II)=23.7$ min; FAB-MS (M+H)$^+$=606.

b) 3(S)-amino-4-phenyl-1-(1-cyclohexylmethylhydrazino)-2(S)-((tert-butoxydimethylsilyl)oxy)-butane;

22.79 g (37.6 mmol) of 3(S)-(Boc-amino)-4-phenyl-1-(2-Boc-1-cyclohexylmethylhydrazino)-2(S)-((tert-butoxydimethylsilyl)oxy)-butane in 0.4 liter of formic acid are stirred at room temperature under a protective gas. After 7 h, the reaction mixture is lyophilised and the residue is partitioned between 3 portions of ethyl acetate, sat. NaHCO$_3$ solution and brine. The organic phase is dried with Na$_2$SO$_4$ and concentrated by evaporation. The resulting foam is used directly in the next stage.

c) (5(S),6(S))-5-benzyl-1-cyclohexylmethyl-6-((tert-butyldimethylsilyl)oxy)-1,2,4-triazepan-3-one;

Under a N$_2$ atmosphere, 7.45 g (46 mmol) of carbonyldiimidazole are added in three portions to 15.08 g (37.1 mmol) of 3(S)-amino-4-phenyl-1-(1-cyclohexylmethylhydrazino)-2(S)-((tert-butoxydimethylsilyl)oxy)-butane dissolved in 465 ml of THF. After each portion, the reaction mixture is stirred for 8 h at RT. It is then concentrated by evaporation and the residue is partitioned between 3 portions of methylene chloride, 10% citric acid solution, water and brine. Drying with Na$_2$SO$_4$ and concentration of the methylene chloride phases by evaporation yields, after digestion with ethyl acetate/petroleum ether, the pure title compound: TLC $R_f(Q)=0.44$; $t_{Ref}(II)=22.8$ min; IR (CH$_2$Cl$_2$): inter alia 3410w, 2950s, 2930s, 2855s, 1675s, 1604w, 1105m.

Alternative synthesis to 1c): Under a N$_2$ atmosphere, 0.30 ml (2.97 mmol) of triethylamine is added to 0.192 mmol of 3(S)-amino-4-phenyl-1-(1-cyclohexylmethylhydrazino)-2 (S)-((tert-butoxydimethylsilyl)oxy)-butane dissolved in 12 ml of methylene chloride. The batch is cooled to −70° C. and 0.326 ml (0.66 mmol) of a 20% solution of phosgene in toluene is added. The batch is slowly heated and the reaction products are partitioned between 3 portions of methylene chloride, sat. NaHCO$_3$ solution and brine. Drying with Na$_2$SO$_4$ and concentration of the methylene chloride phases by evaporation yields the title compound: $t_{Ref}(II)=23.3$ min.

d) (5(S),6(S))-5-benzyl-2,4-bis(4-fluorophenylmethyl)-6-(tert-butyldimethylsilyloxy)-1-cyclohexylmethyl-1,2,4-triazepan-3-one:

Under a N$_2$ atmosphere, 50 mg (55% in oil; 1.16 mmol) of sodium hydride are washed with 3 portions of hexane and suspended in 0.6 ml of DMF. A solution of 50 mg (0.116 mmol) of (5(S),6(S))-5-benzyl-1-cyclohexylmethyl-6-((tert-butyldimethylsilyl)oxy)-1,2,4-triazepan-3-one in 4 ml of DMF is added and the batch is stirred for 5 min to complete the reaction. 36 μl (0.29 mmol) of p-fluoro-benzyl bromide are then added. After 30 min, HPLC indicates that all the components have reacted. The batch is hydrolysed with 0.4 ml of methanol and partitioned between 3 portions of ethyl acetate, water and brine, and the organic phases are dried with Na$_2$SO$_4$ and concentrated by evaporation. Column chromatography (SiO$_2$, petroleum ether/ethyl acetate 10:1) yields the pure title compound: TLC $R_f(R)=0.26$; $t_{Ref}(II)=26.4$ min; FAB-MS (M+H)$^+$=648.

EXAMPLE 2

(5(S),6(S))-5-benzyl-1-cyclohexylmethyl-2,4-bis(4-fluorophenylmethyl)-6-(pyridin-2-ylcarbonyl)oxy-1,2,4-triazepan-3-one At 0° C. and under a N$_2$ atmosphere, 32.2 mg (0.26 mmol) of 2-picolinic acid (=pyridine-2-carboxylic acid; Fluka, Buchs/Switzerland in 0.5 ml of methylene chloride are converted with 22 μl (0.157 mmol) of 1-chloro-N,N,2-trimethyl-1-propeneamine [B. Haveaux, A. Dekoker, M.

Rens, A. R. Sidani, J. Toye, L. Ghosez, M. Murakami, M. Yoshioka and W. Nagata, Organic Syntheses 59, 26 (1980)] into the acid chloride. After 45 min, 1 ml of dioxane, 0.26 ml of pyridine, 0.13 mmol of (5(S),6(S))-5-benzyl-6-(tert-butyldimethylsilyloxy)-1-cyclohexylmethyl-2,4-bis (fluorophenylmethyl)-1,2,4-triazepan-3-one (Example 1 d)) and 0.3 mg of DMAP are added. The reaction is monitored by HPLC and more acid chloride and pyridine are added if necessary. Once all the educt has reacted, the reaction mixture is diluted with methylene chloride and washed twice with sat. NaHCO$_3$ solution, water and brine. The aqueous phases are extracted with 2 portions of methylene chloride and the organic phases are dried with Na$_2$SO$_4$ and concentrated by evaporation to yield the title compound.

EXAMPLE 3

The following compounds are prepared in accordance with one of the above-mentioned processes or in accordance with the process specified:

A1) (5(S),6(S))-5-benzyl-1-cyclohexylmethyl-2,4-diallyl-6-hydroxy-1,2,4-triazepan-3-one:

Under a protective gas, 295 mg (0.572 mmol) of (5(S),6(S))-5-benzyl-2,4-diallyl-6-(tert-butyldimethylsilyloxy)-1-cyclohexylmethyl-1,2,4-triazepan-3-one in 12.6 ml of DMF are desilylated for 18 h at RT with 361 mg (1.144 mmol) of TBAF. The batch is poured into water and extracted three times with ethyl acetate. The organic phases are washed with 2 portions of sat. NaHCO$_3$ solution and brine, dried with Na$_2$SO$_4$, concentrated by evaporation and subjected to column chromatography (SiO$_2$, petroleum ether/ethyl acetate 3:2) to yield the pure title compound: TLC R$_f$(Q)=0.48; t$_{Ref}$(II)=19.1 min; FAB-MS (M+H)$^+$=398; $^1$H-NMR (500 MHz, CDCl$_3$): 0.85 (m, 2 HC$_{axial}$-cyclohex), 1.21 (m, 3 HC$_{axial}$-cyclohex), 1.4 (sb, H(1)-cyclohex), 1.52 (d, J=6 Hz, HO), 1.71 (m, 4 HC$_{equatorial}$-cyclohex), 1.85 (db, J=11 Hz, 1 HC$_{equatorial}$-cyclohex), 2.53 (m, H-CH-C$_6$H$_{11}$), 2.60 (m, H-CH$^{allyl}$), 2.81 (m, H-CH-C$_6$H$_{11}$), 3.00 (d, J=13 Hz, H-CH-phenyl), 3.13 (m, H-CH-phenyl, H$_2$C(7)), 3.46 (m, HC(5)), 3.57 (m, H-CH$^{allyl}$), 4.17 (m, HC(6), H-CH$^{allyl}$), 4.28 (m, H-CH$^{allyl}$), 4.94 (d, J=17 Hz, H-CH$^{olefin}$), 5.03 (d, J=10 Hz, H-CH$^{olefin}$), 5.18 (d, J=10 Hz, H-CH$^{olefin}$), 5.27 (dd, J$_1$=17 Hz, J$_2$=2 Hz, H-CH$^{olefin}$), 5.55 (m, HC$^{olefin}$), 6.04 (m, HC$^{olefin}$), 7.1–7.35 (m, 5 H$^{arom.}$).

The starting material is prepared as follows:

a) (5(S),6(S))-5-benzyl-2,4-diallyl-6-(tert-butyldimethylsilyloxy)-1-cyclohexylmethyl-1,2,4-triazepan-3-one Under a N$_2$ atmosphere, 278 mg (55% in oil; 11.6 mmol) of sodium hydride are washed with 3 portions of hexane and suspended in 6 ml of DMF. A solution of 500 mg (1.16 mmol) of (5(S),6(S))-5-benzyl-1-cyclohexylmethyl-6-((tert-butyldimethylsilyl)-oxy)-1,2,4-triazepan-3-one (Example 1c)) in 24 ml of DMF is added and the batch is stirred for 5 min and then 245 µl (2.895 mmol) of allyl bromide are added dropwise. After 25 min, the batch is hydrolysed with 4 ml of methanol while cooling with ice and partitioned between 3 portions of ethyl acetate, water and brine. The organic phase is dried with Na$_2$SO$_4$ and concentrated by evaporation. Column chromatography (SiO$_2$, petroleum ether/ethyl acetate 10:1) yields the pure title compound: TLC R$_f$(R)=0.35; t$_{Ref}$(II)=26.8 min; FAB-MS (M+H)$^+$=512; IR (CH$_2$Cl$_2$): inter alia 2933s, 2860m, 1636s, 1452m, 1095m, 1080m, 863m, 837m.

A2) (5(S),6(S))-5-benzyl-1-cyclohexylmethyl-2,4-diisobutyl-6-hydroxy-2,4-triazepan-3-one;

A3) (5(S),6(S))-5-benzyl-1-cyclohexylmethyl-2,4-diisopropyl-6-hydroxy-1,2,4-triazepan-3-one;

A4) (5(S),6(S))-5-benzyl-2,4-bis(cyclopropylmethyl)-1-cyclohexylmethyl-6-hydroxy-1,2,4-triazepan-3-one;

A5) (5(S),6(S))-5-benzyl-2,4-bis(phenylmethyl)-1-cyclohexylmethyl-6-hydroxy-1,2,4-triazepan-3-one;

A6) (5(S),6(S))-5-benzyl-2,4-bis(2-naphthyl-methyl)-1-cyclohexylmethyl-6-hydroxy-1,2,4-triazepan-3-one;

B1) (5(S),6(S))-2,4-diallyl-1,5-dibenzyl-6-hydroxy-1,2,4-triazepan-3-one;

B2) (5(S),6(S))-1,5-dibenzyl-2,4-diisobutyl-6-hydroxy-1,2,4-triazepan-3-one;

B3) (5(S),6(S))-1,5-dibenzyl-2,4-diisopropyl-6-hydroxy-1,2,4-triazepan-3-one;

B4) (5(S),6(S))-2,4-bis(cyclopropylmethyl)-1,5-dibenzyl-6-hydroxy-1,2,4-triazepan-3-one;

B5) (5(S),6(S))-1,2,4,5-tetrabenzyl-6-hydroxy-1,2,4-triazepan-3-one;

B6) (5(S),6(S))-2,4-bis(1-naphthylmethyl)-1,5-dibenzyl-6-hydroxy-1,2,4-triazepan-3-one;

C1) (5(S),6(S))-5-benzyl-2,4-diallyl-1-(4-fluorophenylmethyl)-6-hydroxy-1,2,4-triazepan-3-one;

C2) (5(S),6(S))-5-benzyl-2,4-diisobutyl-1-(4-fluorophenylmethyl)-6-hydroxy-1,2,4-triazepan-3-one;

C3) (5(S),6(S))-5-benzyl-2,4-diisopropyl-1-(4-fluorophenylmethyl)-6hydroxy-1,2,4-triazepan-3-one;

C4) (5(S),6(S))-5-benzyl-2,4-bis(cyclopropylmethl)-1-(4-fluorophenylmethyl)-6-hydroxy-1,2,4-triazepan-3-one;

C5) (5(S),6(S))-2,4,5-tribenzyl-1-(4-fluorophenylmethyl)-6-hydroxy-1,2,4-triazepan-3-one;

C6) (5(S),6(S))-5-benzyl-2,4-bis(2-naphthylmethyl)-1-(4-fluorophenylmethyl)-6-hydroxy-1,2,4-triazepan-3-one;

D1) (5(S),6(S))-5-benzyl-2,4-diallyl-6-hydroxy-1-(4-methoxyphenylmethyl)1,2,4-triazepan-3-one;

D2) (5(S),6(S))-5-benzyl-2,4-diisobutyl-6-hydroxy-1-(4-methoxyphenylmethyl)-1,2,4-triazepan-3-one;

D3) (5(S),6(S))-5-benzyl-2,4-diisopropyl-6-hydroxy-1-(4-methoxyphenylmethyl)-1,2,4-triazepan-3-one;

D4) (5(S),6(S))-5-benzyl-2,4-bis(cyclopropylmethyl)-6-hydroxy-1-(4-methoxyphenylmethyl)-1,2,4-triazepan-3-one;

D5) (5(S),6(S))-6-hydroxy-1-(4-methoxyphenylmethyl)-2,4,5-tribenzyl-1,2,4-triazepan-3-one;

D6) (5(S),6(S))-5-benzyl-2,4-bis(1-napthylmethyl)-6-hydroxy-1-(4-methoxyphenylmethyl)-1,2,4-triazepan-3-one;

E1) (5(S),6(S))-5-benzyl-1-(4-cyanophenylmethyl)-2,4-diallyl-6-hydroxy-1,2,4-triazepan-3-one;

E2) (5(S),6(S))-5-benzyl-1-(4-cyanophenylmethyl)-2,4-diisobutyl-6-hydroxy-1,2,4-triazepan-3-one;

E3) (5(S),6(S))-5benzyl-1-(4-cyanophenylmethyl)-2,4-diisopropyl-6-hydroxy-1,2,4triazepan-3-one;

E4) (5(S),6(S))-5-benzyl-2,4-bis(cyclopropylmethyl)-1-(4-cyanophenylmethyl)-6-hydroxy-1,2,4-triazepan-3-one;

E5) (5(S),6(S))-(4-cyanophenylmethyl)-6-hydroxy-2,4,5-tribenzyl-1,2,4-triazepan-3-one;

E6) (5(S),6(S))-5-benzyl-2,4-bis(2-naphthylmethyl)-1-(4-cyanophenylmethyl)-6-hydroxy-1,2,4-triazepan-3-one; F1) (5(S),6(S))-5-benzyl-2,4-diallyl-6-hydroxy-1-(4-isobutyoxyphenylmethyl)-1,2,4-triazepan-3-one;

F2) (5(S),6(S))-5-benzyl-2,4-diisobutyl-6-hydroxy-1-(4-isobutoxyphenylmethyl)-1,2,4-triazepan-3-one;

F3) (5(S),6(S))-5-benzyl-2,4-diisopropyl-6-hydroxy-1-(4-isobutoxyphenylmethyl)-1,2,4-triazepan-3-one;

F4) (5(S),6(S))-5-benzyl-2,4-bis(cyclopropylmethyl)-6-hydroxy-1-(4-isobutoxyphenylmethyl)-1,2,4-triazepan-3-one;

F5) (5(S),6(S))-6-hydroxy-1-(4-isobutoxyphenylmethyl)-2,4,5-tribenzyl-1,2,4-triazepan-3-one;

F6) (5(S),6(S))-5-benzyl-2,4-bis(1-napthylmethyl)-6-hydroxy-1-(4-isobutoxyphenylmethyl)-1,2,4-triazepan-3-one;

G) (5(S),6(S))-1-cyclohexylmethyl-2,4-diallyl-6-hydroxy-5-(4-methoxybenzyl)-1,2,4-triazepan)-3-one;

H) (5(S),6(S))-2,4-bis(cyclopropylmethyl)-1-cyclohexylmethyl-6-hydroxy-5-(4methoxybenzyl)-1,2,4-triazepan-3-one;

I) (5(S),6(S))-1-benzyl-2,4-diallyl-6-hydroxy-5-(4-methoxybenzyl)-1,2,4-triazepan-3-one;

J) (5(S),6(S))-1-benzyl-2,4-bis(cyclopropylmethyl)-6-hydroxy-5-(4-methoxybenzyl)1,2,4-triazepan-3-one;

K) (5(S),6(S))-2,4-diallyl-1-(4-fluorophenylmethyl)-6-hydroxy-5-(4-methoxybenzyl)-1,2,4-triazepan-3-one;

L) (5(S),6(S))-2,4-bis(cyclopropylmethyl)-1-(4-fluorophenylmethyl)-6-hydroxy-5-(4-methoxybenzyl)-1,2,4-triazepan-3-one.

EXAMPLE 4

(5(R),6(R))-5-benzyl-2,4-bis(4-fluorophenylmethyl)-1-cyclohexylmethyl-6-hydroxy-1,2,4-triazepan-3-one:

18.8 mg (0.06 mmol) of TBAF are added to a solution of 20 mg (0.03 mmol) of (5(R),6(R))-5-benzyl-2,4-bis(4-fluorophenylmethyl)-6-(tert-butyldimethylsilyloxy)-1-cyclohexylmethyl-1,2,4-triazepan-3-one in 0.3 ml of DMF. After 3 h at RT, the batch is poured into water and extracted with 3 portions of ethyl acetate. The organic phases are washed with water, sat. sodium hydrogen carbonate solution and brine, dried with $Na_2SO_4$ and concentrated by evaporation. Column chromatography ($SiO_2$, hexane/ethyl acetate 10:1→8:1) yields the title compound: TLC $R_f(D)$=0.25; FAB-MS (M+H)$^+$=534; $^1$H-NMR (200 MHz, $CDCl_3$): 0.75–1.0, 1.1–1.45, 1.55–1.85 (3m, cyclohexyl), 2.57 (m, 1H), 2.7–3.05 (m, 6H), 3.35 (m, 1H), 3.78 (m, 1H), 4.00 (d, J=13 Hz, 1H), 4.74 (d, J=15 Hz, 1H), 4.93 (d, J=13 Hz, 1H), 6.9–7.1 (m, 9H), 7.2–7.35 (m, 2H), 7.4–7.5 (m, 2H).

The starting material is prepared as follows:

a) 3(R)-(Boc-amino)-4-phenyl-1-(2-Boc-1-cyclohexylmethylhydrazino)-butan-2(R)-ol:

Under a protective gas, a solution of 3.75 g (14.2 mmol) of (2S)-[1'(R)-Boc-amino-2'-phenylethyl]oxirane [prepared analogously to (2R)-[1'(S)-Boc-amino-2'-phenylethyl]-oxirane (EP-532466-A2, page 42) from (D)-N-Boc-phenylalaninal instead of (L)-N-Boc-phenylalaninal] and 3.24 g (14.2 mmol) of tert-butyl-3-benzyl-carbazate (J. Chem. Soc., Perkin I, 1712 (1975)) in 47 ml of methanol is heated under reflux for 18 h. Concentration of the reaction mixture by evaporation and precipitation with hexane from a concentrated solution in methylene chloride yields the title compound: TLC $R_f(T)$=0.09; $t_{Ret}(II)$=19.2.

b) 3(R)-(Boc-amino)-4-phenyl-1-(2-Boc-1-cyclohexylmethylhydrazino)-2(R)-((tert-butoxydimethylsilyl)oxy)-butane:

Analogously to Example 1 a), 2.81 g (5.71 mmol) of 3(R)-(Boc-amino)-4-phenyl-1-(2-Boc-1-cyclohexylmethylhydrazino)-butan-2(R)-ol in 6.2 ml of dioxane and 0.84 ml of DMF are reacted with 2.8 g of imidazole and 3.1 g (20 mmol) of tert-butyl-dimethylchlorosilane. Column chromatography ($SiO_2$, hexane/ethyl acetate 8:1) yields the title compound: TLC $R_f(T)$=0.48; $t_{Ret}(II)$=24.1 min.

c) 3(R)-amino-4-phenyl-1-(1-cyclohexylmethylhydrazino)-2(R)-((tert-butoxydimethylsilyl)oxy)-butane:

1.95 g (3.2 mmol) of 3(R)-(Boc-amino)-4-phenyl-1-(2-Boc-1-cyclohexylmethylhydrazino)-2(R)-((tert-butoxydimethylsilyl)oxy)-butane in 34 ml of formic acid are stirred at RT under a protective gas. After 6 h, the reaction mixture is lyophilised and the residue is partitioned between 3 portions of ethyl acetate, sat. $NaHCO_3$ solution and brine. The organic phase is dried with $Na_2SO_4$ and concentrated by evaporation. The crude product is used immediately in the next stage.

d) (5(R),6(R))-5-benzyl-1-cyclohexylmethyl-6-((tert-butyldimethylsilyl)oxy)-1,2,4-triazepan-3-one:

Under a protective gas, 440 mg (2.7 mmol) of carbonyldiimidazole are added to 1.1 g (2.7 mmol) of 3(R)-amino-4-phenyl-1-(1-cyclohexylmethylhydrazino)-2(R)-((tert-butoxydimethylsilyl)oxy)-butane in 30 ml of THF and the batch is stirred for 24 h at RT. Because TLC indicates that 3(R)-(amino)-4-phenyl-1-(1-cyclohexylmethylhydrazino)-2(R)-((tert-butoxydimethylsilyl)oxy)-butane is still present in the reaction mixture, a further 200 mg and, after a further 12 h, a further 100 mg of carbonyldiimidazole are added. After stirring for another 24 h at RT, the reaction mixture is concentrated by evaporation and the residue is taken up in ethyl acetate and washed with sat. $NaHCO_3$ solution and brine. The aqueous phases are extracted twice with ethyl acetate and the organic phases are dried with $Na_2SO_4$ and concentrated by evaporation. Column chromatography ($SiO_2$, hexane/ethyl acetate 2:1) yields the title compound: FAB-MS (M+H)$^+$=432.

e) (5(R),6(R))-5-benzyl-2,4-bis(4-fluorophenylmethyl)-6-(tert-butyldimethylsilyloxy)-1-cyclohexylmethyl-1,2,4-triazepan-3-one:

Under a $N_2$ atmosphere, 45 mg (80% in white oil; 1.5 mmol) of sodium hydride are washed with 3×3 ml of hexane and suspended in 1 ml of DMF. A solution of 64.7 mg (0.15 mmol) of (5(R),6(R))-5-benzyl-1-cyclohexylmethyl-6-((tert-butyldimethylsilyl)-oxy)-1,2,4-triazepan-3-one in 3 ml of DMF is added and the batch is stirred for 5–10 min to complete the reaction. 48.5 µl (0.375 mmol) of p-fluorobenzyl bromide are then added by means of a syringe. After 1.5 h at RT, TLC indicates that all the components have reacted. The batch is hydrolysed with 0.5 ml of methanol, partitioned between 3 portions of ethyl acetate, water and brine, and the organic phases are dried with $Na_2SO_4$ and concentrated by evaporation. Column chromatography ($SiO_2$:, hexane/ethyl acetate 19:1→10:1) yields the pure title compound: TLC $R_f(D)$=0.61; FAB-MS (M+H)$^+$=648.

EXAMPLE 5

(5(S),6(S))-5-benzyl-1-cyclohexylmethyl-2,4-bis(n-propyl)-6-hydroxy-1,2,4-triazepan-3-one:

A solution of 70 mg (0.176 mmol) of (5(S),6(S))-5-benzyl-1-cyclohexylmethyl-2,4-diallyl-6-hydroxy-1,2,4-triazepan-3-one (Example 3A1) is hydrogenated in 3 ml of methanol in the presence of 15 mg of 10% Pd/C. The solution is filtered and concentrated by evaporation to yield the title compound: $t_{Ret}(II)$=19.7 min; FAB-MS (M+H)$^+$= 402.

EXAMPLE 6

(5(R),6(R))-5-benzyl-1-cyclohexylmethyl-2,4-diallyl-6-hydroxy-1,2,4-triazepan-3-one:

Under a protective gas, 18 mg (0.035 mmol) of (5(R),6(R))-5-benzyl-2,4-diallyl-6-(tert-butyldimethylsilyloxy)-1-cyclohexylmethyl-1,2,4-triazepan-3-one in 0.3 ml of DMF are desilylated for 3 h at RT with 18.8 mg (0.059 mmol) of TBAF. The reaction mixture is taken up in ethyl acetate and washed with water, sat. $NaHCO_3$ solution and brine. The aqueous phases are extracted twice with ethyl acetate and the organic phases are dried with $Na_2SO_4$ and concentrated by evaporation. Column chromatography ($SiO_2$, hexane/ ethyl acetate 10:1→8:1) yields the title compound: TLC $R_f(D)$=0.20; FAB-MS (M+H)$^+$=398.

The starting material is prepared as follows:

a) (5(R),6(R))-5-benzyl-2,4-diallyl-6-(tert-butyldimethylsilyloxy)-1-cyclohexylmethyl-1,2,4-triazepan-3-one Under a N$_2$ atmosphere, 51 mg (80% in white oil; 1.7 mmol) of sodium hydride are washed with 3 3-ml portions of hexane and suspended in 1 ml of DMF. A solution of 74 mg (0.17 mmol) of (5(R),6(R))-5-benzyl-1-cyclohexylmethyl-6-((tert-butyldimethylsilyl)oxy)-1,2,4-triazepan-3-one (Example 4 d)) in 3 ml of DMF is added, the batch is stirred for 5–10 min (→evolution of gas), and 36.4 µl (0.43 mmol) of allyl bromide are added. After 1.5 h, the batch is hydrolysed, while cooling with ice, with 0.5 ml of methanol (→foaming) and partitioned between 3 portions of ethyl acetate, water and brine. The organic phase is dried with Na$_2$SO$_4$ and concentrated by evaporation. Column chromatography (SiO$_2$, hexane/ethyl acetate 10:1) yields the pure title compound: TLC $R_f(D)$=0.73; FAB-MS (M+H)$^+$= 512.

EXAMPLE 7

(5(S),6(S))-5-benzyl-1-cyclohexylmethyl-2,4-bis(4-methoxy-phenylmethyl)-6-hydroxy-1,2,4-triazepan-3-one:

Under a protective gas, 2.16 g (approx. 60% strength; 1.92 mmol) of (5(S),6(S))-5-benzyl-2,4-bis(4-methoxy-phenylmethyl)-6-(tert-butyldimethylsilyloxy)-1-cyclohexylmethyl-1,2,4-triazepan-3-one in 42 ml of DMF are desilylated for 18 h at RT with 1.22 g (3.85 mmol) of TBAF. The batch is poured into water and extracted three times with ethyl acetate, and the organic phases are washed with 2 portions of sat. NaHCO$_3$ solution and brine, dried with Na$_2$SO$_4$, concentrated by evaporation and subjected to column chromatography (SiO$_2$, hexane/ethyl acetate 4:1) to yield the pure title compound: TLC $R_f(D)$=0.08; $t_{Ref}(II)$= 19.6 min; FAB-MS (M+H)$^+$=558; [α]$^D$=−34° (c=1; ethanol).

The starting material is prepared as follows:

a) (5(S),6(S))-5-benzyl-2,4-bis(4-methoxy-phenylmethyl)-6-(tert-butyldimethylsilyloxy)-1-cyclohexylmethyl-1,2,4-triazepan-3-one:

Under a N$_2$ atmosphere, 1.39 g (55% in oil; 57.9 mmol) of sodium hydride are washed with 3 portions of hexane and suspended in 30 ml of DMF. A solution of 2.5 g (5.79 mmol) of (5(S),6(S))-5-benzyl-1-cyclohexylmethyl-6-((tert-butyldimethylsilyl)oxy)-1,2,4-triazepan-3-one (Example 1 c)) in 50 ml of DMF is added and the batch is stirred for 5 min and 2.1 ml (14.5 mmol) of p-methoxy-benzyl chloride are added dropwise. After 50 min, the reaction mixture is poured into 200 ml of a 1% solution of NH$_4$Cl in ice-water and extracted with 3 portions of ethyl acetate. The organic phases are washed with water and brine, dried with Na$_2$SO$_4$ and concentrated by evaporation. Column chromatography (SiO$_2$, hexane/ethyl acetate 3:1) yields the title compound which, according to HPLC, still contains approximately 40% p-methoxy-benzyl chloride: TLC $R_f(J)$=0.4; $t_{Ref}(II)$= 26.6 min.

EXAMPLE 8 cis-[(5(R),6(R))/(5(S),6(S))]-5-benzyl-1-cyclohexylmethyl-2,4-bis(4-methoxy-phenylmethyl)-6-hydroxy-1,2,4-triazepan-3-one and trans-[(5(R),6(S))/(5(S),6(R))]-5-benzyl-1-cyclohexylmethyl-2,4-bis(4-methoxy-phenylmethyl)-6-hydroxy-1,2,4-triazepan-3-one (in racemate form):

Under a protective gas, 7.7 mg (0.206 mmol) of NaBH$_4$ are added to an ice-cooled solution of 104 mg (0.187 mmol) of (5(R/S))-5-benzyl-1-cyclohexylmethyl-2,4-bis(4-methoxy-phenylmethyl)-6-oxo-1,2,4-triazepan-3-one in 1.8 ml of methanol. After stirring for 35 min, the reaction mixture is adjusted to pH 6–7 with acetic acid and concentrated by evaporation using a RE. The residue is taken up in methylene chloride and the resulting solution is washed with water and brine, dried with Na$_2$SO$_4$ and concentrated by evaporation. Column chromatography (SiO$_2$, methylene chloride/ether 20:1) yields first racemic cis-5-benzyl-1-cyclohexylmethyl-2,4-bis(4-methoxy-phenylmethyl)-6-hydroxy-1,2,4-triazepan-3-one and then racemic trans-5-benzyl-1-cyclohexylmethyl-2,4-bis(4-methoxy-phenylmethyl)-6-hydroxy-1,2,4-triazepan-3-one: cis-isomer: TLC $R_f(H)$-0.25; $t_{Ref}(II)$=19.8 min; FAB-MS (M+H)$^+$=558; trans-isomer: TLC $R_f(H)$-0.13; $t_{Ref}(II)$=20.4 min; FAB-MS (M+H)$^+$=558.

The starting material is prepared as follows:

a) (5(S))-5-benzyl-1-cyclohexylmethyl-2,4-bis(4-methoxy-phenylmethyl)-6-oxo-1,2,4-triazepan-3-one:

Under a N$_2$ atmosphere, 160 µl (2.26 mmol) of DMSO in 2.8 ml of methylene chloride are added dropwise at −60° C. by means of a syringe to a solution of 145 µl (1.70 mmol) of oxalyl chloride in 1.5 ml of methylene chloride. After 15 min, 630 mg (1.13 mmol) of (5(S),6(S))-5-benzyl-1-cyclohexylmethyl-2,4-bis(4-methoxy-phenylmethyl)-6-hydroxy-1,2,4-triazepan-3-one (Example 7) in 6.3 ml of methylene chloride/THF 1:1 are added dropwise to the clear solution and the batch is stirred for 25 min at −60° C. 630 µl (4.52 mmol) of triethylamine in 1.3 ml of methylene chloride are then added and the batch is stirred for 30 min at −30° C. and cooled to −60° C. again. 10.1 ml of 20% KHSO$_4$ solution are then added, followed by 1.3 ml of hexane. The reaction mixture is heated to RT and the aqueous phase is separated off and extracted with 2 portions of ether. The organic phases are washed with sat. NaHCO$_3$ solution, water and brine, dried with Na$_2$SO$_4$, concentrated by evaporation and subjected to column chromatography (SiO$_2$, hexane/ethyl acetate 5:1) to yield the title compound: TLC $R_f(J)$=0.4; $t_{Ref}(II)$=20.8 min; FAB-MS (M+H)$^+$=556; [α]$^D$=−83° (c=1; ethanol).

b) (5(R/S))-5-benzyl-1-cyclohexylmethyl-2,4-bis(4-methoxy-phenylmethyl)-6-oxo-1,2,4-triazepan-3-one:

Under a protective gas, a solution of 360 mg (0.648 mmol) of (5(S))-5-benzyl-1-cyclohexylmethyl-2,4-bis(4-methoxy-phenylmethyl)-6-oxo-1,2,4-triazepan-3-one in 1.5 ml of THF is stirred for 18 h at RT with 4.5 mg (0.032 mmol) of 1,5,7-triazobicyclo[4.4.0]dec-5-ene. The batch is then concentrated by evaporation and the residue is partitioned between 3 portions of ethyl acetate and 10% citric acid solution, water and brine. The organic phases are dried with Na$_2$SO$_4$, concentrated by evaporation and subjected to column chromatography (SiO$_2$, hexane/ethyl acetate 5:1) to yield the title compound: TLC $R_f(J)$=0.38; $t_{Ref}(II)$=20.8 min; [α]$^D$=−0.7°±0.9° (c=1; ethanol).

EXAMPLE 9

Gelatin Solution

A sterile-filtered aqueous solution, with 20% cyclodextrins as solubilisers, of one of the compounds of formula I mentioned in the above Examples, as active ingredient, is so mixed under aseptic conditions, with heating, with a sterile gelatin solution containing phenol as preservative that 1.0 ml of solution has the following composition:

| active ingredient | 3 mg |
| --- | --- |
| gelatin | 150.0 mg |
| phenol | 4.7 mg |
| dist. water with 20% cyclodextrins as solubilisers | 1.0 ml |

EXAMPLE 10

Sterile Dry Substance For Injection 5 mg of one of the compounds of formula I mentioned in the above Examples are dissolved as active ingredient in 1 ml of an aqueous solution containing 20 mg of mannitol and 20% cyclodextrins as solubilisers. The solution is sterile-filtered and introduced into a 2 ml ampoule under aseptic conditions, deep-frozen and lyophilised. Before being used, the lyophilisate is dissolved in 1 ml of distilled water or 1 ml of physiological saline solution. The solution is administered intramuscularly or intravenously. The formulation can also be introduced into double-chamber disposable ampoules.

EXAMPLE 11

Nasal Spray 500 mg of finely ground (<5.0 μm) powder of one of the compounds of formula I mentioned in the above Examples are suspended as active ingredient in a mixture of 3.5 ml of Myglyol 812® and 0.08 g of benzyl alcohol. The suspension is introduced into a container having a metering valve. 5.0 g of Freon 12® are introduced into the container through the valve under pressure. The "Freon" is dissolved in the Myglyol-benzyl alcohol mixture by shaking. The spray container contains approximately 100 single doses which can be administered individually.

EXAMPLE 12

Film-Coated Tablets

The following constituents are processed for the preparation of 10 000 tablets each comprising 100 mg of active ingredient:

| active ingredient | 1000 g |
| --- | --- |
| corn starch | 680 g |
| colloidal silica | 200 g |
| magnesium stearate | 20 g |
| stearic acid | 50 g |
| sodium carboxymethyl starch | 250 g |
| water | quantum satis |

A mixture of one of the compounds of formula I mentioned in the above Examples, as active ingredient, 50 g of corn starch and the colloidal silica is processed with starch paste comprising 250 g of corn starch and 2.2 kg of demineralised water to form a moist mass which is forced through a sieve of 3 mm mesh size and dried at 45° for 30 min in a fluidised bed drier. The dried granules are pressed through a sieve of 1 mm mesh size, mixed with a previously sieved mixture (1 mm sieve) of 330 g of corn starch, the magnesium stearate, the stearic acid and the sodium carboxymethyl starch and compressed to form slightly biconvex tablets.

What is claimed is:

1. A compound of formula I

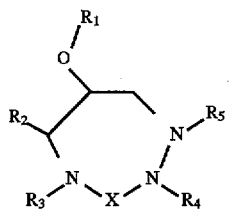

wherein $R_1$ is hydrogen or acyl, $R_2$, $R_3$, $R_4$ and $R_5$ are each independently of the others unsubstituted or substituted alkyl or alkenyl, and X together with the two bonds shown in the formula forms a bivalent radical selected from the group consisting of —(C=O)—, —(C=S)—, —(S=O)—, —(S(=O)$_2$)—, —(P=O)—,

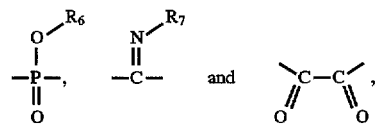

$R_6$ being unsubstituted or substituted alkyl and $R_7$ being hydrogen, unsubstituted or substituted alkyl, hydroxy, amino, alkyloxy, cyano or aryloxy, or a salt thereof.

2. A compound according to claim 1 of formula I, wherein $R_1$ is lower alkanoyl; octanoyl, nonanoyl, decanoyl, undecanoyl, dodecanoyl, palmitoyl; lower alkenoyl; lower alkynoyl; substituted lower alkanoyl wherein the substituents are selected from up to three radicals from the group consisting of hydroxy, lower alkoxy, lower alkoxy-lower alkoxy, lower alkoxy-lower alkoxy-lower alkoxy, phenyl-lower alkoxy, naphthyl-lower alkoxy, phenyloxy-lower alkoxy wherein the phenyl radical may be unsubstituted or substituted by halogen up to three times, phenoxy, naphthyloxy, lower alkanoyloxy, phenyl-lower alkanoyloxy, halogen, carboxy, lower alkoxycarbonyl, phenyl-lower alkoxycarbonyl, carbamoyl, lower alkylcarbamoyl, hydroxy-lower alkylcarbamoyl, di-lower alkylcarbamoyl, bis(hydroxy-lower alkyl)carbamoyl, cyano, oxo, $C_3$–$C_8$cycloalkyl, phenyl, naphthyl, $C_6$–$C_{12}$bicycloalkyl, $C_9$–$C_{14}$tricycloalkyl, $C_4$–$C_8$cycloalkenyl, heterocyclyl that is unsubstituted or substituted by lower alkyl, mono-, di- or triphenyl-lower alkyl wherein phenyl is unsubstituted or lower alkoxy-substituted, lower alkanoyl, hydroxy, lower alkoxy, phenyl-lower alkoxy, phenyl-lower alkoxycarbonyl, hydroxy-lower alkyl, halogen, cyano and/or by trifluoromethyl and that is selected from pyrrolyl, 2,5-dihydropyrrolyl, furyl, thienyl, tetrahydrofuryl, cyclohepta[b]pyrrolyl, pyrrolidinyl, imidazolyl, imidazolidinyl, pyrazolinyl, pyrazolidinyl, triazolyl, tetrazolyl, tetrahydro-oxazolyl, tetrahydro-isoxazolyl, tetrahydro-thiazolyl, tetrahydro-isothiazolyl, indolyl, isoindolyl, quinolyl, isoquinolyl, benzimidazolyl, benzofuranyl, pyridyl, pyrimidinyl, pyrazinyl, piperidinyl, piperazin-1-yl, morpholino, thiomorpholino, S,S-dioxothiomorpholino, 1,2-dihydro- or 1,2,3,4-tetrahydro-quinolyl, and 1,2-dihydro- or 1,2,3,4-tetrahydro-isoquinolyl, and aryl selected from phenyl, naphthyl and fluorenyl, aryl being unsubstituted or mono- or poly-substituted by lower alkyl, halo-lower alkyl, halogen, hydroxy, lower alkoxy, lower alkanoyloxy, carboxy, lower alkyloxycarbonyl, phenyl-lower alkoxycarbonyl, carbamoyl, mono- or di-lower alkylcarbamoyl, mono- or di-hydroxy-lower alkylcarbamoyl, heterocyclyl-lower alkyl wherein heterocyclyl is as defined above as substituent of lower alkanoyl $R_1$ and is bonded via a ring nitrogen atom, by cyano and/or by nitro; or $R_1$ is a residue, bonded via the carbonyl of its carboxy group to the bonding oxygen atom, of an amino acid selected from glycine, alanine, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid, valine, norvaline, leucine, isoleucine, norleucine, serine, homoserine, threonine, methionine, cysteine, trans-3- and trans-4-hydroxyproline, phenylalanine, tyrosine, 4-aminophenylalanine, 4-chlorophenylalanine, 4-carboxyphenylalanine, β-phenylserine, phenylglycine, α-naphthylalanine, cyclohexylalanine, cyclohexylglycine, tryptophan, aspartic acid, asparagine, aminomalonic acid, aminomalonic acid monoamide, glutamic acid, glutamine, histidine, arginine, lysine, δ-hydroxylysine, ornithine, 3-aminopropanoic acid, α,γ-diaminobutyric acid and α,β-diaminopropionic acid, wherein an amino group is unsubstituted or mono- or di-N-alkylated by lower alkyl, by imidazolyl-lower alkyl, by pyridyl-lower alkyl, and/or by phenyl-lower alkyl, and/or N-acylated by unsubstituted or substituted lower alkanoyl, as defined above for lower alkanoyloxy $R_1$;

the radicals $R_2$, $R_3$, $R_4$ and $R_5$ are each independently of the others lower alkyl that is unsubstituted or substituted by up to four substituents selected from cycloalkyl that has from 3 to 7 carbon atoms; cycloalkenyl that has from 3 to 7 carbon atoms; bicycloalkyl that contains from 5 to 10 carbon atoms; bicycloalkenyl having from 8 to 12 carbon atoms; tricycloalkyl wherein tricycloalkyl contains from 8 to 10 carbon atoms; aryl selected from phenyl, indenyl, indanyl, naphthyl, anthryl, phenanthryl, acenaphthyl and fluorenyl, wherein aryl may be unsubstituted or substituted by one or up to three radicals selected from lower alkyl, halo-lower alkyl, phenyl, 1- or 2-naphthyl, hydroxy, lower alkoxy, phenyl-lower alkoxy wherein the phenyl radical may itself be unsubstituted or substituted by halogen, hydroxy or by lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, halogen, carboxy, lower alkoxycarbonyl, phenyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and cyano, wherein phenyl may be present once or up to three times; heterocyclyl selected from thienyl, furyl, pyrrolyl, imidazolyl, pyrazolyl, oxazolyl, thiazolyl, tetrazolyl, pyridyl, pyrazinyl, pyrimidinyl, pyridazinyl, indolyl, benzimidazolyl, quinolyl, isoquinolyl, 3,1-benzofuranyl, cyclohexa[b]pyrrolyl, cyclohexa[b]pyridyl, cyclohexa[b]pyrazinyl, cyclohexa[b]pyrimidinyl, pyrrolidinyl, pyrrolinyl, imidazolidyl, piperidyl, piperazinyl, morpholinyl, thiomorpholinyl, S,S-dioxo-thiomorpholinyl, indolinyl, iso-indolinyl, 4,5,6,7-tetrahydroindolyl, 1,2,3,4-tetrahydroquinolyl and 1,2,3,4-tetrahydroisoquinolyl, wherein heterocyclyl is unsubstituted or substituted by up to three substituents selected independently of one another from lower alkyl, phenyl, 1- or 2-naphthyl, phenyl-lower alkyl, hydroxy-lower alkyl, lower alkoxy-lower alkyl, lower alkanoyloxy-lower alkyl, phenyl- or naphthyl-lower alkanoyloxy-lower alkyl, lower alkoxycarbonyloxy-lower alkyl, phenyl-lower alkoxycarbonyloxy-lower alkyl, amino-lower alkyl, aminomethyl, hydroxy, lower alkoxy, amino, lower alkylamino, di-lower alkylamino, carboxy, lower alkoxycarbonyl, phenyl- or naphthyl-lower alkoxycarbonyl, halogen, lower alkanoyl, carbamoyl, mono- or di-lower alkylcarbamoyl, hydroxy- or carboxy-lower alkyl-carbamoyl, nitro, oxo and cyano; hydroxy; hydroxy-lower alkoxy; lower alkoxy; lower alkoxy-lower alkoxy; lower alkoxy-lower alkoxy-lower alkoxy; lower alkoxy-lower alkoxy-lower alkoxy-lower alkyl; lower alkanoyloxy; lower alkanoyloxy-lower alkyl; amino; lower alkanoylamino; lower alkoxycarbonylamino; phenyl-lower alkoxycarbonylamino; amino substituted at the amino nitrogen atom by heterocyclyl-lower alkanoyl wherein heterocyclyl is as defined above as substituent of substituted lower alkyl independently of the radicals mentioned there; up to three halogen atoms; carboxy; lower alkoxycarbonyl; sulfonyl; carbamoyl; lower alkylcarbamoyl; di-lower alkylcarbamoyl; carbamoyl substituted at the nitrogen atom by a radical selected from ethylene, trimethylene, tetramethylene and pentamethylene wherein a carbon atom may have been replaced by nitrogen oxygen, sulfur or sulfur mono- or di-substituted by oxygen; N-heterocyclyl-lower alkylcarbamoyl or N-lower alkyl-N-heterocyclyl-lower alkylcarbamoyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, each of which may also be completely or partially saturated, and from morpholinyl and thiomorpholinyl; oxo that is not in the 1-position of the alkyl radical; and from cyano; or the radicals $R_2$, $R_3$, $R_4$ and $R_5$ are each independently of the others lower alkenyl;

X together with the two bonds shown in formula I forms a bivalent radical selected from the group consisting of —(C=O)—, —(C=S)—, —(S=O)—, —(S(=O)$_2$)— and

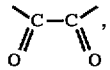

or a salt thereof.

3. A compound of formula I according to claim 1 wherein $R_1$ is hydrogen, X is a bivalent radical —(C=O)— and the remaining radicals are as defined, or a pharmaceutically acceptable salt thereof.

4. A compound of formula I according to claim 1 wherein $R_1$ is hydroxy, $R_2$, $R_3$, $R_4$ and $R_5$ are each independently of the others a radical selected from phenyl-lower alkyl, naphthyl-lower alkyl, fluorophenyl-lower alkyl, cyclopropyl-lower alkyl, cyclohexyl-lower alkyl, cyanophenyl-lower alkyl, lower alkoxyphenyl-lower alkyl, lower alkyl and lower alkenyl, and X together with the two bonds shown in formula I forms a bivalent radical —(C=O)—, —(C=S), —(S=O— or —(S(=O)₂)—, or a salt thereof.

5. A compound according to claim 1 formula Ia

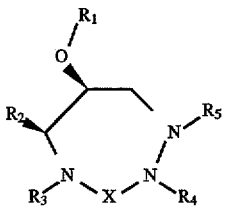

wherein the radicals are as defined, or a salt thereof.

6. A compound according to any one of claims 1 to 4 of formula Ib

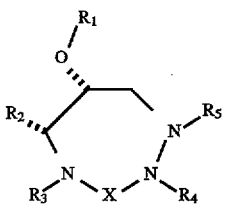

wherein the radicals are as defined, or a salt thereof.

7. A pharmaceutical composition comprising a compound or a pharmaceutically acceptable salt according to claim 1 and at least one pharmaceutically acceptable carrier.

8. A compound or a pharmaceutically acceptable salt according to claim 1 for use in a method for the diagnostic or therapeutic treatment of the human or animal body.

9. A compound or a pharmaceutically acceptable salt according to claim 1 for use in the preparation of a pharmaceutical composition for the treatment of retroviral disease.

10. A compound or a pharmaceutically acceptable salt according to claim 1 for use in the treatment of retroviral diseases.

11. A compound or a pharmaceutically acceptable salt according to claim 1 for use in the inhibition of HIV-1-protease.

12. A method of treating a warm-blooded animal suffering from a retroviral disease, comprising the administration of a dose, effective in the treatment of retroviral diseases, of a compound of formula I, or of a pharmaceutically acceptable salt thereof, according to claim 1 to a warm-blooded animal requiring such treatment.

13. A pharmaceutical composition suitable for administration to a warm-blooded animal for the treatment of a retroviral disease responsive to the inhibition of retroviral aspartate proteases, comprising an anti-retrovirally effective amount of a compound of formula I, or of a pharmaceutically acceptable salt thereof, according to claim 1 and a pharmaceutically acceptable carrier.

14. A process for the preparation of a compound of formula I according to claim 1, wherein a) for the preparation of a compound of formula I the remaining radicals are as defined, protecting groups present in a compound of formula II

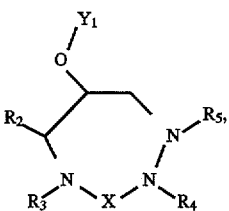

wherein $Y_1$ is a hydroxy-protecting group, other reactive groups are, if necessary, also in protected form and the remaining radicals are as defined for compounds of formula I, or in a salt thereof, are removed, or b) for the preparation of a compound of formula I wherein $R_1$ has one of the meanings mentioned for compounds of formula I with the exception of hydrogen, and $R_3$ and $R_4$ each have the same meaning, a compound of formula III

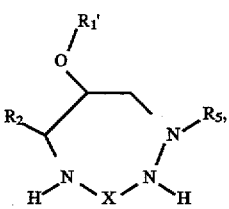

wherein $R_1'$ is as defined for $R_1$ in compounds of formula I with the exception of hydrogen, or a salt thereof, is alkylated with a compound of formula IV $$R—L_1 \quad (IV),$$

wherein R is a radical as defined for $R_3$ and $R_4$ and $L_1$ is a nucleofugal leaving group, or c) for the preparation of a compound of formula I wherein $R_1$ has one of the mentioned meanings with the exception of hydrogen, and the remaining radicals are as defined, a compound of formula I, wherein $R_1$ is hydrogen and the remaining radicals are as defined and, if necessary, other functional groups are in protected form, is reacted with an acid of formula V $$R_1'—OH \quad (V),$$

wherein $R_1'$ is one of the radicals $R_1$ with the exception of hydrogen, or with a reactive acid derivative thereof, and, if necessary, protecting groups present are removed, and, if desired, a compound of formula I that is obtainable by one of the above processes a) to c) and has at least one salt-forming group is converted into its salt, or an obtainable salt is converted into the free compound or into a different salt and/or, if necessary, obtainable mixtures of isomers are separated and/or a compound of formula I according to the invention is converted into a different compound of formula I according to the invention.

15. A compound of formula III

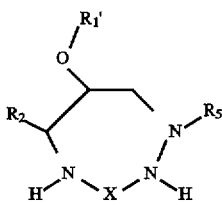

wherein $R_1'$ is as defined for $R_1$ in compounds of formula I in claim 1 with the exception of hydrogen, or a salt thereof.

16. A compound of formula Ie or If

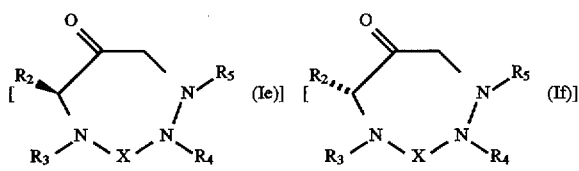

wherein the radicals $R_2$, $R_3$, $R_4$ and $R_5$ and also X are as defined in claim 1 for compounds of formula I, or a salt thereof.

17. A compound of formula I according to claim 1 selected from the group consisting of:

(5(S),6(S))-5-benzyl-2,4-bis(4-fluorphenylmethyl)-1-cyclohexylmethyl-6-hydroxy-1,2,4-triazepan-3-one, (5(S),6(S))-5-benzyl-1-cyclohexylmethyl-2,4-diallyl-6-hydroxy-1,2,4-triazepan-3-one, (5(R),6(R))-5-benzyl-2,4-bis(4-fluorophenylmethyl)-1-cyclohexylmethyl-6-hydroxy-1,2,4-triazepan-3-one, (5(S),6(S))-5-benzyl-1-cyclohexylmethyl-2,4-bis(n-propyl)-6-hydroxy-1,2,4-triazepan-3-one, (5(R),6(R))-5-benzyl-1-cyclohexylmethyl-2,4-diallyl-6-hydroxy-1,2,4-triazepan-3-one, (5(S),6(S))-5-benzyl-1-cyclohexylmethyl-2,4-bis(4-methoxy-phenylmethyl)-6-hydroxy-1,2,4-triazepan-3-one, cis-(5(R),6(R)/5(S),6(S))-5-benzyl-1-cyclohexylmethyl-2,4-bis(4-methoxy-phenylmethyl)-6-hydroxy-1,2,4-triazepan-3-one, (5(R),6(S)/5(S),6(R))-5-benzyl-1-cyclohexylmethyl-2,4-bis(4-methoxy-phenylmethyl)-6-hydroxy-1,2,4-triazepan-3-one, or a pharmaceutically acceptable salt thereof.

* * * * *